(12) United States Patent
Iwakuma et al.

(10) Patent No.: US 8,039,127 B2
(45) Date of Patent: *Oct. 18, 2011

(54) ORGANIC ELECTROLUMINESCENCE DEVICE AND MATERIAL FOR ORGANIC ELECTROLUMINESCENCE DEVICE

(75) Inventors: Toshihiro Iwakuma, Sodegaura (JP);
Yoriyuki Takashima, Sodegaura (JP);
Mitsunori Ito, Sodegaura (JP);
Toshinari Ogiwara, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 155 days.

This patent is subject to a terminal disclaimer.

(21) Appl. No.: 12/427,999

(22) Filed: Apr. 22, 2009

(65) Prior Publication Data

US 2010/0253211 A1    Oct. 7, 2010

(30) Foreign Application Priority Data

Apr. 6, 2009   (JP) ................ 2009-092523

(51) Int. Cl.
*H01L 51/54*   (2006.01)
(52) U.S. Cl. ......... 428/690; 313/504; 313/505; 313/506
(58) Field of Classification Search ............... 428/690; 313/504, 505, 506
See application file for complete search history.

(56) References Cited

U.S. PATENT DOCUMENTS

| | | | |
|---|---|---|---|
| 5,429,884 A | 7/1995 | Namiki et al. | |
| 6,734,457 B2 | 5/2004 | Yamizaki et al. | |
| 2002/0182441 A1 | 12/2002 | Lamansky et al. | |
| 2004/0142206 A1 | 7/2004 | Bazan et al. | |
| 2005/0175857 A1 | 8/2005 | Coggan et al. | |
| 2006/0035109 A1 | 2/2006 | Arakane et al. | |
| 2006/0134456 A1 | 6/2006 | Ikeda et al. | |
| 2006/0210828 A1 | 9/2006 | Nakayama et al. | |
| 2007/0052346 A1 | 3/2007 | Iwakuma et al. | |
| 2007/0054151 A1 | 3/2007 | Iwakuma et al. | |
| 2007/0069638 A1 | 3/2007 | Matsuura et al. | |
| 2007/0090753 A1 | 4/2007 | Arakane | |
| 2007/0108898 A1 | 5/2007 | Matsuura et al. | |
| 2007/0159083 A1 | 7/2007 | Matsuura et al. | |
| 2007/0172698 A1 | 7/2007 | Iwakuma et al. | |
| 2007/0188083 A1 | 8/2007 | Iwakuma et al. | |
| 2007/0243411 A1 | 10/2007 | Takashima et al. | |
| 2007/0257600 A1 | 11/2007 | Matsuura et al. | |
| 2007/0296328 A1 | 12/2007 | Matsuura et al. | |
| 2008/0224603 A1 | 9/2008 | Hashimoto et al. | |
| 2008/0246391 A1 | 10/2008 | Iwakuma et al. | |
| 2009/0009065 A1 | 1/2009 | Nishimura et al. | |
| 2009/0009066 A1 | 1/2009 | Nishimura et al. | |
| 2009/0009067 A1* | 1/2009 | Nishimura et al. ........... 313/504 |
| 2009/0045730 A1 | 2/2009 | Nishimura et al. | |
| 2009/0045731 A1 | 2/2009 | Nishimura et al. | |
| 2009/0128010 A1 | 5/2009 | Hyun et al. | |

FOREIGN PATENT DOCUMENTS

| | | |
|---|---|---|
| JP | 10-189248 | 7/1998 |
| JP | 11-012205 | 1/1999 |
| JP | 2001-244075 | 9/2001 |
| JP | 2001-250690 | 9/2001 |
| JP | 2001-257074 | 9/2001 |
| JP | 2001-332384 | 11/2001 |
| JP | 2003-27048 | 1/2003 |
| JP | 2003-142267 | 5/2003 |
| JP | 2003-317946 | 11/2003 |
| JP | 2004-14334 | 1/2004 |
| JP | 2004-75567 | 3/2004 |
| JP | 2004-281390 | 10/2004 |
| JP | 2005-8588 | 1/2005 |
| JP | 2005-19219 | 1/2005 |
| JP | 2005-63938 | 3/2005 |
| JP | 2005- 71983 | 3/2005 |
| JP | 2005-071983 | 3/2005 |
| JP | 2005-197262 | 7/2005 |
| JP | 2005-222948 | 8/2005 |
| JP | 2006-45503 | 2/2006 |
| JP | 2006-52323 | 2/2006 |
| JP | 2006-151966 | 6/2006 |
| JP | 2009-504730 | 2/2009 |
| WO | WO 02/20693 A1 | 3/2002 |
| WO | WO 2005/084083 A1 | 9/2005 |
| WO | WO 2005/112519 A1 | 11/2005 |
| WO | WO 2007/046658 A1 | 4/2007 |
| WO | WO 2007/069569 A1 | 6/2007 |
| WO | WO 2009/008199 A1 | 1/2009 |
| WO | WO 2009/008200 A1 | 1/2009 |

| | | | |
|---|---|---|---|
| WO | WO 2009/008205 A1 | 1/2009 | |
| WO | WO 2009/008215 A1 | 1/2009 | |
| WO | WO 2009/008356 A1 | 1/2009 | |

OTHER PUBLICATIONS

A. Salinas Castillo, et al., "Heavy Atom Induced Room Temperature Phosphorescence: a Tool for the Analytical Characterization of Polycyclic Aromatic Hydrocarbons", Analytica Chimica ACTA 516, 2004, pp. 213-220. International Search Report issued Jun. 29, 2010, in PCT/JP 2010/056166 with English translation of category of cited documents.
U.S. Office Action U.S. Appl. No. 12/108,066 dated Dec. 28, 2010.
U.S. Office Action U.S. Appl. No. 12/122,316 dated Feb. 2, 2011.
Applied Physics Letters, (1999), vol. 75, No. 1, pp. 4-6.
Bruno, et al., CRC Handbook of Fundamental Spectroscopic Correlation Charts, p. 2.
Office Action as received in U.S. Appl. No. 12/122,316 dated Jul. 1, 2011.

\* cited by examiner

*Primary Examiner* — D. Lawrence Tarazano
*Assistant Examiner* — Gregory Clark
(74) *Attorney, Agent, or Firm* — Oblon, Spivak, McClelland, Maier & Neustadt, L.L.P.

(57) ABSTRACT

An organic electroluminescence device includes: a cathode; an anode; and a single-layered or multilayered organic thin-film layer provided between the cathode and the anode. In the organic electroluminescence device, at least one layer of the organic thin-film layer includes: an organic-electroluminescence-device material represented by a general formula selected from the following formulae (1), (2) and (3); and at least one phosphorescent material. In the formula: A represents a group selected from a 3-fluoranthenyl group, 5-benzo[c]phenanthrenyl group, 6-benzo[c]phenanthrenyl group and 10-benzo[g]chrysenyl group; Ar represents a fused aromatic ring having 10 to 30 carbon atoms and having triplet energy of 2.10 eV or more; and A or Ar is allowed to be substituted by a phenyl group or a naphthyl group.

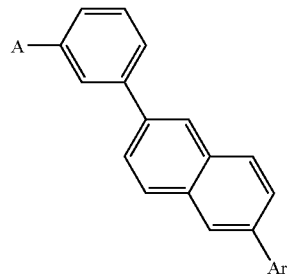

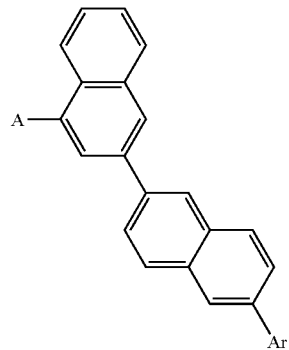

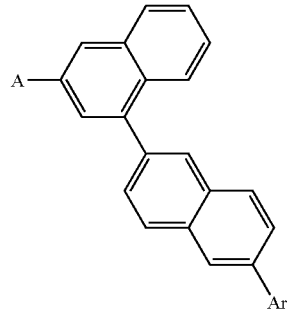

16 Claims, 1 Drawing Sheet

ORGANIC ELECTROLUMINESCENCE DEVICE AND MATERIAL FOR ORGANIC ELECTROLUMINESCENCE DEVICE

BACKGROUND OF THE INVENTION

1. Field of the Invention

The present invention relates to an organic electroluminescence device (hereinafter abbreviated as organic EL device as needed) and a material for the organic electroluminescence device. In particular, the present invention relates to an organic electroluminescence device including a red emitting layer and a material used for the organic electroluminescence device.

2. Description of Related Art

An organic EL device, which includes an organic thin-film layer (in which an emitting layer is included) between an anode and a cathode, has been known to emit light using exciton energy generated by a recombination of holes and electrons that have been injected into the emitting layer (e.g., see document 1: US2002/0182441, document 2: WO2005/112519, document 3: JP-A-2003-142267, document 4: WO2007/046658, document 5: JP-A-2006-151966, document 6: JP-A-2005-8588, document 7: JP-A-2005-19219, document 8: JP-A-2005-197262, document 9: JP-A-2004-75567, document 10: US2008/0224603, document 11: JP-A-2004-281390, document 12: JP-A-2006-045503, document 13: WO2009/008215, document 14: WO2009/008205, document 15: WO2002/20693, document 16: JP-A-2001-250690, document 17: JP-A-2001-244075, document 18: JP-A-2001-257074, and document 19: JP-A-10-189248).

Such an organic EL device, which has the advantages as a self-emitting device, is expected to serve as an emitting device excellent in luminous efficiency, image quality, power consumption and thin design.

An example of a further improvement to be made in an organic EL device is an improvement in luminous efficiency.

In this respect, in order to enhance internal quantum efficiency, developments have been made on an emitting material (phosphorescent material) that emits light using triplet excitons. In recent years, there has been a report on a phosphorescent organic EL device.

Since the internal quantum efficiency can be enhanced up to 75% or more (up to approximately 100% in theory) by forming the emitting layer (phosphorescent-emitting layer) from such a phosphorescent material, an organic EL device having high efficiency and consuming less power can be obtained.

In forming the emitting layer, a doping method, according to which an emitting material (dopant) is doped to a host material, has been known as a usable method.

The emitting layer formed by the doping method can efficiently generate excitons from electric charges injected into the host material. With the exciton energy generated by the excitons being transferred to the dopant, the dopant can emit light with high efficiency.

In order to intermolecularly transfer the energy from the host material to the phosphorescent dopant, triplet energy $Eg_H$ of the host material is required to be larger than triplet energy $Eg_D$ of the phosphorescent dopant.

A known representative example of a material having effectively-large triplet energy has been CBP (4,4'-bis(N-carbazolyl)biphenyl). See, for instance, the document 1.

By using such CBP as the host material, energy can be transferred to a phosphorescent dopant for emitting light of a predetermined emitting wavelength (e.g., green, red), by which an organic EL device of high efficiency can be obtained.

Alternatively, the document 2 discloses a technique according to which a fused-ring derivative containing a nitrogen-containing ring such as carbazole is used as the host material for a red-phosphorescent-emitting layer.

On the other hand, a variety of host materials (fluorescent hosts) for fluorescent dopants that generate fluorescent emission are known. Various proposals have been made on a host material capable of, with a combination of a fluorescent dopant, providing a fluorescent-emitting layer excellent in luminous efficiency and lifetime.

However, although a fluorescent host has larger excited singlet energy $Eg(S)$ than a fluorescent dopant, such a fluorescent host does not necessarily have larger triplet energy $Eg(T)$. Accordingly, it is not successful to simply apply the fluorescent host to the host material (phosphorescent host) for a phosphorescent-emitting layer.

A well-known example of such a fluorescent host is an anthracene derivative.

However, triplet energy $Eg(T)$ of an anthracene derivative is relatively small (approximately 1.9 eV). Thus, energy cannot be reliably transferred to a phosphorescent dopant for emitting light having a wavelength in a visible light range of 520 nm to 720 nm. In addition, excited triplet energy cannot be trapped within the emitting layer.

Accordingly, an anthracene derivative is not suitable for the phosphorescent host.

Further, derivatives such as a perylene derivative, a pyrene derivative and a naphthacene derivative are not preferable phosphorescent hosts for the same reason above.

Alternatively, an exemplary arrangement in which an aromatic hydrocarbon compound is used as the phosphorescent host has been known (the document 3). In the arrangement disclosed in the document 3, a compound in which two aromatic groups are bonded as substituents to a benzene central skeleton in meta positions is used as the phosphorescent host.

The documents 4 to 9 disclose organic EL devices in which various aromatic hydrocarbon compounds are used.

Further, the document 10 exemplifies compounds in which fused aromatic hydrocarbon rings are arranged at right and left substituent positions of 2,7-naphthalene rings.

The document 11 exemplifies compounds in which phenanthroline rings (nitrogen-containing heterocycles) are arranged at right and left substituent positions of 2,7-naphthalene rings.

The document 12 exemplifies compounds in which aromatic substituent groups of which essential skeletons are anthracene rings are arranged at right and left substituent positions of 2,7-naphthalene rings.

Moreover, the documents 13 and 14 disclose compounds having a structure in which four aromatic hydrocarbon rings are continuously coupled to one another and organic EL devices in which the compounds are used. Such an aromatic hydrocarbon compound is structured so that: the aromatic hydrocarbon ring at one terminal end is a fused polycyclic aromatic ring; the aromatic hydrocarbon ring adjoined and coupled to that aromatic hydrocarbon ring is a divalent benzene ring having a meta bonding; and the remaining two rings are fused aromatic rings. The documents further disclose that a device of which emitting layer uses both the aromatic hydrocarbon compound and a red-phosphorescent complex exhibits relatively high efficiency and relatively long device lifetime.

Further, fluoranthene compounds related to this invention and organic EL devices in which the fluoranthene compounds are used are also disclosed in the documents 15 to 19.

However, when applied with CBP as the host material, the organic EL device disclosed in the document 1 exhibits much higher luminous efficiency due to phosphorescent emission on one hand, but exhibits such a short lifetime as to be practically unusable on the other hand. Such a problem is considered to be attributed to considerable degradation of molecules by holes due to not-high oxidation stability that the molecular structure of CBP exhibits.

Although the organic EL device disclosed in the document 2 exhibits improvement in the luminous efficiency and lifetime, the improved luminous efficiency and lifetime may not be always sufficient for practical application.

The aromatic hydrocarbon compound disclosed in the document 3 is molecularly structured such that the molecules extend from the benzene central skeleton in a manner symmetrical relative to the benzene central skeleton. Therefore, an emitting layer applied with the aromatic hydrocarbon compound tends to be easily crystallized. Accordingly, an organic EL device in which the aromatic hydrocarbon compound disclosed in the document 3 is used may require higher driving voltage.

The documents 4 to 9 are totally silent on the effectivity of the aromatic hydrocarbon compounds used in organic EL devices as the phosphorescent hosts.

In the organic EL devices disclosed in the documents 10 to 14, which require relatively high driving voltage, lifetime of the devices may not be sufficiently prolonged.

Further, the documents 15 to 19 are totally silent on structures in which the fluoranthene compounds and phosphorescent materials are used together in organic EL devices.

SUMMARY OF THE INVENTION

An object of the invention is to provide a material for phosphorescent organic EL devices capable of reducing driving voltage and exhibiting high efficiency and long lifetime, and to provide an organic EL device in which the material is used.

After conducting concentrated studies in order to achieve such an object, the inventors have found that a phosphorescent organic EL device that requires less driving voltage and exhibits high efficiency and long lifetime can be provided by using a material for organic EL devices (hereinafter abbreviated as organic-EL-device material as needed) selected from structures respectively represented by the following formulae (1), (2) and (3), and reached the invention.

An organic EL device according to an aspect of the invention includes: a cathode; an anode; and a single-layered or multilayered organic thin-film layer provided between the cathode and the anode, in which at least one layer of the organic thin-film layer includes:

an organic-electroluminescence-device material represented by a general formula selected from following formulae (1), (2) and (3); and at least one phosphorescent material.

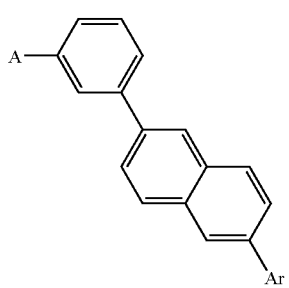

(1)

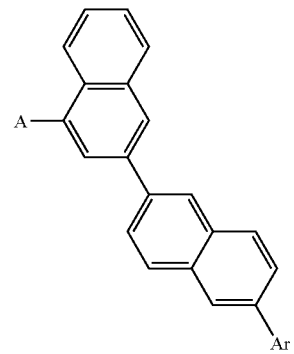

(2)

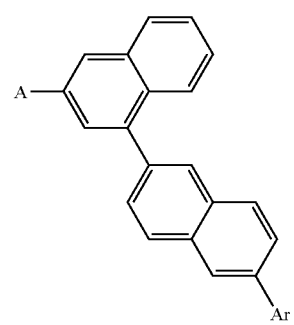

(3)

In the formula: A represents a group selected from a 3-fluoranthenyl group, 5-benzo[c]phenanthrenyl group, 6-benzo[c]phenanthrenyl group and 10-benzo[g]chrysenyl group;

Ar represents a fused aromatic ring having 10 to 30 carbon atoms and having triplet energy of 2.10 eV or more; and A or Ar is allowed to be substituted by a phenyl group or a naphthyl group.

In this respect, similarly to the invention, the documents 13 and 14 disclose general formulae for representing aromatic hydrocarbon compounds structured so that four aromatic hydrocarbon rings are continuously coupled to one another. However, the documents 13 and 14 are silent on specific compounds having such structures as represented by any one of the above formulae (1), (2) and (3) according to the aspect of the invention. The examples in the documents 13 and 14 show that the organic EL devices of the documents 13 and 14 require driving voltage of 4.1 to 4.7 V, based on which it can be said that there is still a room for improvement.

Among the various linkage structures of four rings linked in series disclosed in the documents 13 and 14, an organic-EL-device material according to another aspect of the invention has the specific linkage structure represented by any one of the general formulae (1) to (3). Specifically, the organic-EL-device material according to the aspect of the invention is structured such that: the middle divalent aromatic rings have a 2,6 naphthalene skeleton; and the fused aromatic ring at the terminal end is the specific aromatic ring. Accordingly, in an organic EL device containing the organic-EL-device material according to the aspect of the invention, considerable reduction in driving voltage of the organic EL device takes place, which is not disclosed in the document 13 or 14.

Since the conjugation length is elongated suitably for the molecular structure and the fused aromatic hydrocarbon ring contributing to reduction in voltage via the divalent aromatic hydrocarbon ring positioned in meta position is at the terminal end in the organic-EL-device material according to the aspect of the invention, an organic EL device exhibiting high luminous efficiency and excellent lifetime and requiring less driving voltage can be realized.

An organic-EL-device material according to another aspect of the invention is represented by a following formula (1), (2) or (3).

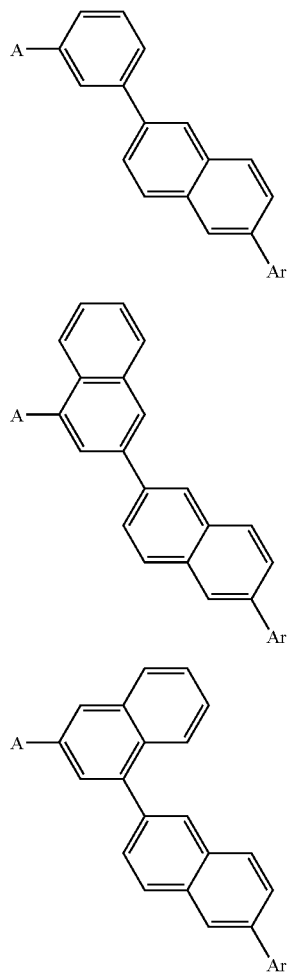

In the formula: A represents a group selected from a 3-fluoranthenyl group, 5-benzo[c]phenanthrenyl group, 6-benzo[c]phenanthrenyl group and 10-benzo[g]chrysenyl group;

Ar represents a fused aromatic ring having 10 to 30 carbon atoms and having triplet energy of 2.10 eV or more; and A or Ar is allowed to be substituted by a phenyl group or a naphthyl group.

The aspect of the invention can provide a phosphorescent organic EL device that requires less driving voltage and exhibits high efficiency and long lifetime because of its use of the organic-EL-device material represented by any one of the formulae (1), (2) and (3), and also can provide the organic-EL-device material capable of realizing such an organic EL device.

DETAILED DESCRIPTION OF PREFERRED EMBODIMENT(S)

Figure 1:
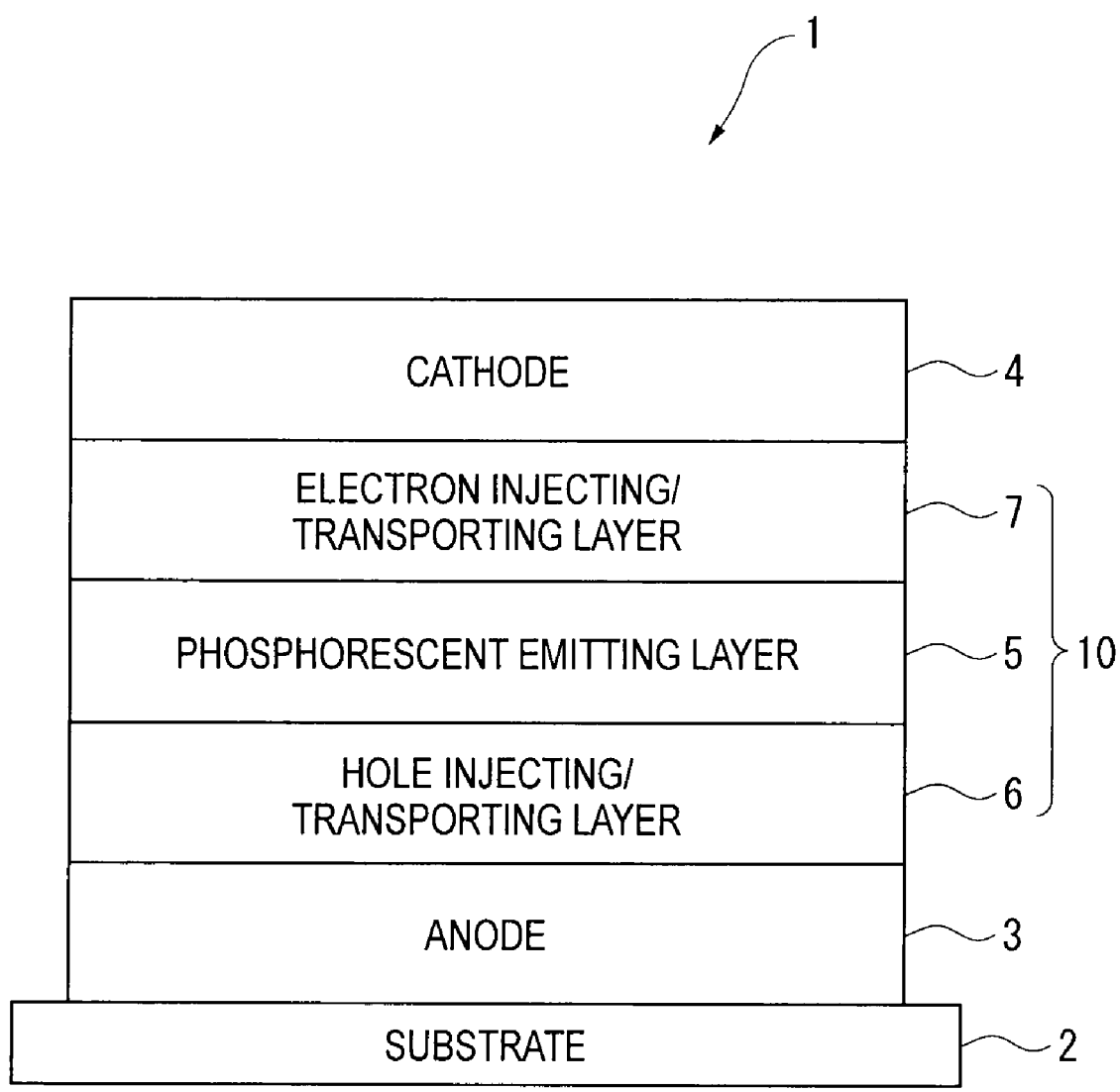
FIG. 1 schematically shows an exemplary arrangement of an organic electroluminescence device according to an exemplary embodiment of the invention.

Exemplary embodiment(s) of the invention will be described below.

(Arrangement of Organic EL Device)

Arrangement(s) of an organic EL device according to the aspect of the invention will be described below.

The followings are representative arrangement examples of an organic EL device:

(1) anode/emitting layer/cathode;
(2) anode/hole injecting layer/emitting layer/cathode;
(3) anode/emitting layer/electron injecting•transporting layer/cathode;
(4) anode/hole injecting layer/emitting layer/electron injecting•transporting layer/cathode;
(5) anode/organic semiconductor layer/emitting layer/cathode;
(6) anode/organic semiconductor layer/electron blocking layer/emitting layer/cathode;
(7) anode/organic semiconductor layer/emitting layer/adhesion improving layer/cathode;
(8) anode/hole injecting•transporting layer/emitting layer/electron injecting•transporting layer/cathode;
(9) anode/insulating layer/emitting layer/insulating layer/cathode;
(10) anode/inorganic semiconductor layer/insulating layer/emitting layer/insulating layer/cathode;
(11) anode/organic semiconductor layer/insulating layer/emitting layer/insulating layer/cathode;
(12) anode/insulating layer/hole injecting•transporting layer/emitting layer/insulating layer/cathode; and
(13) anode/insulating layer/hole injecting•transporting layer/emitting layer/electron injecting•transporting layer/cathode.

While the arrangement (8) is preferably used among the above, the arrangement of the invention is not limited to the above arrangements.

FIG. 1 schematically shows an exemplary arrangement of an organic EL device according to an exemplary embodiment of the invention.

An organic EL device 1 includes a transparent substrate 2, an anode 3, a cathode 4 and an organic thin-film layer 10 disposed between the anode 3 and the cathode 4.

The organic thin-film layer 10 includes a phosphorescent-emitting layer 5 containing a phosphorescent host and a phosphorescent dopant. A layer such as a hole injecting/transporting layer 6 may be provided between the phosphorescent-emitting layer 5 and the anode 3 while a layer such as an electron injecting/transporting layer 7 may be provided between the phosphorescent-emitting layer 5 and the cathode 4.

In addition, an electron blocking layer may be provided to the phosphorescent-emitting layer 5 adjacently to the anode 3 while a hole blocking layer may be provided to the phosphorescent-emitting layer 5 adjacently to the cathode 4.

With this arrangement, electrons and holes can be trapped in the phosphorescent-emitting layer 5, thereby enhancing probability of exciton generation in the phosphorescent-emitting layer 5.

It should be noted that a "fluorescent host" and a "phosphorescent host" herein respectively mean a host combined with a fluorescent dopant and a host combined with a phosphorescent dopant, and that a distinction between the fluorescent host and phosphorescent host is not unambiguously derived only from a molecular structure of the host in a limited manner.

In other words, the fluorescent host herein means a material for forming a fluorescent-emitting layer containing a fluorescent dopant, and does not mean a host that is only usable as a host of a fluorescent material.

Likewise, the phosphorescent host herein means a material for forming a phosphorescent-emitting layer containing a phosphorescent dopant, and does not mean a host that is only usable as a host of a phosphorescent material.

It should also be noted that the "hole injecting/transporting layer (or hole injecting•transporting layer)" herein means "at least one of hole injecting layer and hole transporting layer" while "electron injecting/transporting layer (or electron injecting•transporting layer)" herein means "at least one of electron injecting layer and electron transporting layer".

(Light-Transmissive Substrate)

The organic EL device according to the aspect of the invention is formed on a light-transmissive substrate. The light-transmissive plate, which supports the organic EL device, is preferably a smoothly-shaped substrate that transmits 50% or more of light in a visible region of 400 nm to 700 nm.

The light-transmissive plate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate resins, acryl resins, polyethylene terephthalate resins, polyether sulfide resins and polysulfone resins can be used.

(Anode and Cathode)

The anode of the organic EL device is used for injecting holes into the hole injecting layer, the hole transporting layer or the emitting layer. It is effective that the anode has a work function of 4.5 eV or more.

Exemplary materials for the anode are alloys of indium-tin oxide (ITO), tin oxide (NESA), indium zinc oxide, gold, silver, platinum and copper.

The anode may be made by forming a thin film from these electrode materials through a method such as vapor deposition or sputtering.

When light from the emitting layer is to be emitted through the anode as in this embodiment, the anode preferably transmits more than 10% of the light in the visible region. Sheet resistance of the anode is preferably several hundreds Ω/square or lower. Although depending on the material of the anode, thickness of the anode is typically in a range of 10 nm to 1 μm, and preferably in a range of 10 to 200 nm.

The cathode is preferably formed of a material with smaller work function in order to inject electrons into the electron injecting layer, the electron transporting layer or the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

Like the anode, the cathode may be made by forming a thin film from the above materials through a method such as vapor deposition or sputtering. In addition, the light may be emitted through the cathode.

(Emitting Layer)

The emitting layer of the organic EL device has functions as follows, namely:

(1) injecting function: a function for accepting, when an electrical field is applied, the holes injected by the anode or the hole injecting layer, or the electrons injected by the cathode or the electron injecting layer;

(2) transporting function: a function for transporting injected electric charges (the electrons and the holes) by the force of the electrical field; and (3) emitting function: a function for providing a condition for recombination of the electrons and the holes to emit light.

Injectability of the holes may differ from that of the electrons and transporting capabilities of the hole and the electrons (represented by mobilities of the holes and the electrons) may differ from each other.

As a method of forming the emitting layer, known methods such as vapor deposition, spin coating and an LB method may be employed.

The emitting layer is preferably a molecular deposit film.

The molecular deposit film means a thin film formed by depositing a material compound in gas phase or a film formed by solidifying a material compound in a solution state or in liquid phase. The molecular deposit film is typically distinguished from a thin film formed by the LB method (molecular accumulation film) by differences in aggregation structures, higher order structures and functional differences arising therefrom.

As disclosed in JP-A-57-51781, the emitting layer can be formed from a thin film formed by spin coating or the like, the thin film being formed from a solution prepared by dissolving a binder (e.g. a resin) and a material compound in a solvent.

The thickness of the emitting layer is preferably in a range of 5 to 50 nm, more preferably in a range of 7 to 50 nm and most preferably in a range of 10 to 50 nm. The thickness below 5 nm may cause difficulty in forming the emitting layer and in controlling chromaticity, while the thickness above 50 nm may increase driving voltage.

(Organic-EL-Device Material)

At least one layer of the organic thin-film layer according to the aspect of the invention contains: an organic-EL-device material represented by the following formula (1), (2) or (3); and at least one phosphorescent material.

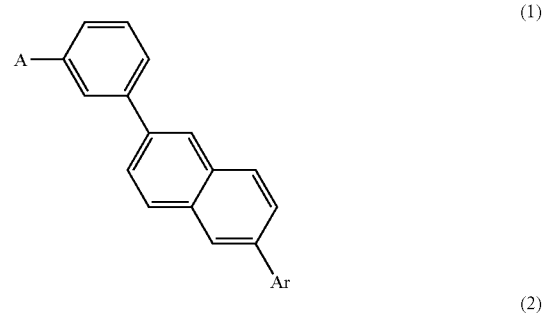

(1)

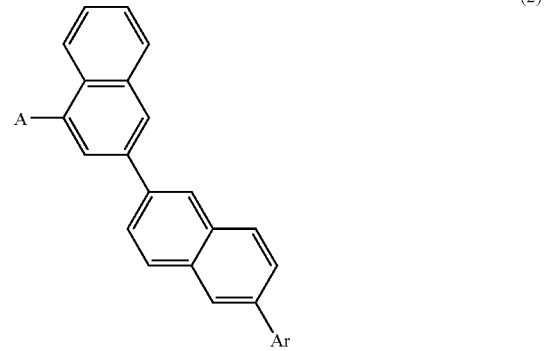

(2)

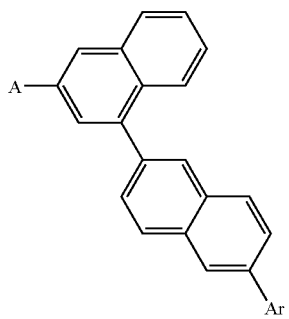

(3)

In the formula: A represents a group selected from 3-fluoranthenyl group, 5-benzo[c]phenanthrenyl group, 6-benzo[c]phenanthrenyl group and 10-benzo[g]chrysenyl group;

Ar represents a fused aromatic ring having 10 to 30 carbon atoms and having triplet energy of 2.10 eV or more;

A or Ar may have a phenyl group or a naphthyl group as substituent(s).

The fused aromatic ring having 10 to 30 carbon atoms and having triplet energy of 2.10 eV or more means that the triplet energy of the fused aromatic ring having 10 to 30 carbon atoms is 2.10 eV or more when the fused aromatic ring is structured in Ar—H structure. The level of the triplet energy is measurable in accordance with the later-described measuring method of triplet energy. The upper limit to the triplet energy of Ar may be suitably set within a range where the advantages of the invention are obtained. The triplet energy of Ar is preferably 2.8 eV or less.

Examples of the fused aromatic ring having 10 to 30 carbon atoms and having triplet energy of 2.1 eV or more are naphthalene, phenanthrene, fluoranthene, triphenylene, chrysene, picene, benzo[c]phenanthrene, dibenzo[c,g]phenanthrene, benzo[g]chrysene, and benzo[b]fluoranthene.

At least one layer of the organic thin-film layer of the organic EL device according to the aspect of the invention may be the emitting layer. The emitting layer may contain: the organic-EL-device material represented by the above formula (1), (2) or (3); and at least one phosphorescent material.

Since having great triplet energy, the organic-EL-device material represented by the formula (1), (2) or (3) according to the aspect of the invention is usable as a host for transferring energy to the phosphorescent dopant so that the phosphorescent dopant can emit light.

While an anthracene derivative, which is well-known as a fluorescent host, is not suitably applied as a host for red-emitting phosphorescent dopant, the organic-EL-device material according to the aspect of the invention, which has great triplet energy, is effectively applicable for the red-emitting phosphorescent dopant to emit light.

However, while CBP, which is a conventionally-known phosphorescent host, can serve as the host even for a phosphorescent dopant for emitting light of a shorter wavelength than green, the organic-EL-device material according to the aspect of the invention can be used for a green-emitting phosphorescent dopant but cannot be used for a phosphorescent dopant for emitting light of a shorter wavelength than green.

According to the aspect of the invention, since the skeleton of the organic-EL-device material has a polycyclic fused ring containing no nitrogen atom, molecular stability thereof can be enhanced and the lifetime of the device can be prolonged.

When the number of ring atoms (i.e., atoms for forming the ring) contained in the skeleton is too small, the molecular stability thereof is not sufficiently high. On the other hand, when the number of rings fused in the polycyclic fused ring for structuring the compound according to the aspect of the invention is too large, the conjugate is excessively lengthened and a HOMO-LUMO gap is so much narrowed that the triplet energy becomes insufficient for a useful emission wavelength. In this respect, since containing the suitable number of the ring atoms, the organic-EL-device material according to the aspect of the invention can be favorably applied as the phosphorescent host for a highly-stable phosphorescent-emitting layer that emits light of a useful wavelength.

Further, since the organic-EL-device material according to the aspect of the invention has the fused aromatic hydrocarbon having the specific structure for contributing to voltage reduction at its terminal end, the driving voltage of the organic EL device can be reduced.

Conventionally, a host material widely usable for phosphorescent dopants that emit light of wide wavelengths ranging from green to red has been selected for each phosphorescent dopant. Thus, a material having great triplet energy Eg(T) such as CBP has been used as the host material.

However, it is true that CBP has great triplet energy Eg(T), but lifetime is short.

In this respect, the organic-EL-device material according to the aspect of the invention is not applicable as a host for such a wide-gap phosphorescent dopant as to be comparable to a blue-emitting phosphorescent dopant, but is applicable as a host for a red-emitting or green-emitting phosphorescent dopant. Moreover, when the triplet energy Eg(T) is great as in CBP, a difference in energy gap between the material and the red-emitting phosphorescent dopant is so large that the energy is not efficiently transferred intermolecularly. However, since the host according to the aspect of the invention has an excited energy value suitable for a red-emitting or green-emitting phosphorescent dopant, energy can be efficiently transferred from the excitons of the host to the phosphorescent dopant, thereby providing a phosphorescent emitting layer of considerably high efficiency. Even when the phosphorescent dopant is directly excited, the organic-EL-device material according to the aspect of the invention, which has sufficiently greater triplet energy than the phosphorescent dopant, can efficiently trap the energy within the emitting layer.

As described above, according to the aspect of the invention, a phosphorescent emitting layer having high efficiency and long lifetime can be provided.

Triplet energy Eg(T) of a material for forming an organic EL device may be exemplarily defined based on the phosphorescence spectrum. For instance, in the invention, the triplet energy Eg(T) may be defined as follows.

Specifically, each material is dissolved in an EPA solvent (diethylether:isopentane:ethanol=5:5:2 in volume ratio) with a concentration of 10 μmol/L, thereby forming a sample for phosphorescence measurement.

Then, the sample for phosphorescence measurement is put into a quartz cell, cooled to 77 K and irradiated with exciting light, so that a wavelength of phosphorescence radiated therefrom is measured.

A tangent line is drawn to be tangent to a rising section adjacent to the short-wavelength side of the obtained phosphorescence spectrum, and a wavelength value at an intersection of the tangent line and a base line is converted into energy value. Then, the converted energy value is defined as the triplet energy gap Eg(T).

For the measurement, for instance, a commercially-available FLUOROLOG II (manufactured by SPEX Corporation) may be used.

However, the triplet energy gap does not need to be defined by the above method, but may be defined by any other suitable method as long as compatible with the invention.

The organic-EL-device material represented by the formula (1), (2) or (3) according to the aspect of the invention preferably has triplet energy of 2.0 eV to 2.5 eV.

When the triplet energy is 2.0 eV or more, energy can be transferred to a phosphorescent material that emits light in a range of 520 to 720 nm. When the triplet energy exceeds 2.5 eV, a difference in the triplet energy between the red dopant and the host material within the emitting layer may becomes so large that the driving voltage is increased.

The triplet energy of the organic-EL-device material according to the aspect of the invention is preferably in a range of 2.1 eV to 2.5 eV, more preferably in a range of 2.2 eV to 2.5 eV.

In the organic-EL-device material represented by the formula (1), (2) or (3) according to the aspect of the invention, A preferably represents a group selected from unsubstituted 3-fluoranthenyl group, 5-benzo[c]phenanthrenyl group, 6-benzo[c]phenanthrenyl and 10-benzo[g]chrysenyl group.

In addition, in the organic-EL-device material according to the aspect of the invention, Ar each preferably independently represent a group selected from a naphthyl group, fluoranthenyl group, phenanthrenyl group, benzophenanthrenyl group and benzo[g]chrysenyl group.

Further, in the organic-EL-device material according to the aspect of the invention, Ar preferably represents a group selected from a 2-naphthyl group, 3-fluoranthenyl group, 8-fluoranthenyl group, 9-phenanthrenyl group, 5-benzo[c]phenanthrenyl group, 6-benzo[c]phenanthrenyl group and 10-benzo[g]chrysenyl group.

By adopting the groups having the specific structures as the groups represented by A and Ar of the organic-EL-device material according to the aspect of the invention in the above-described manner, the level of the triplet energy can be made suitable and the driving voltage can be reduced.

Examples of the organic-EL-device material represented by the formula (1), (2) or (3) are compounds shown below.

(A1)

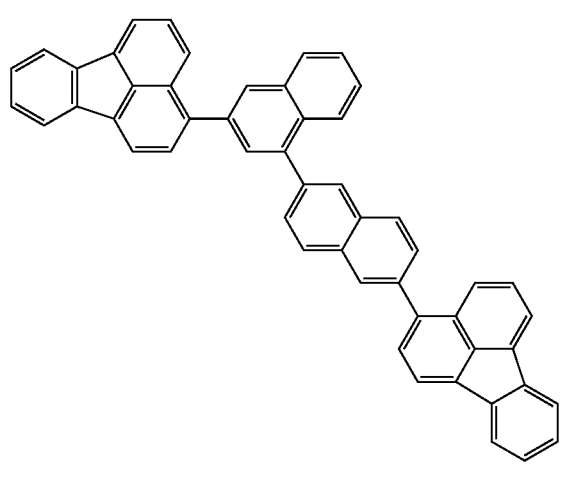

(A2)

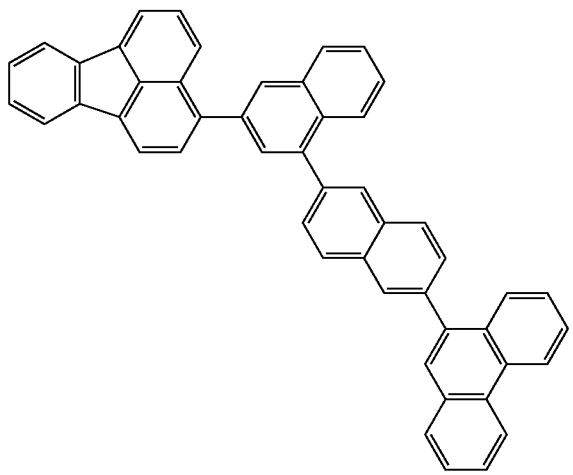

(A3)

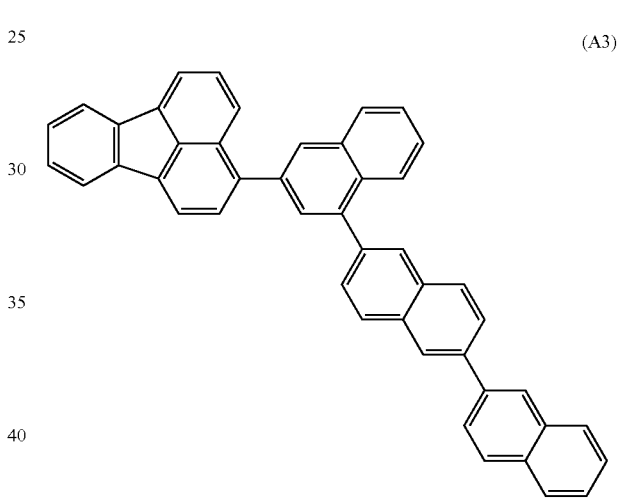

(A4)

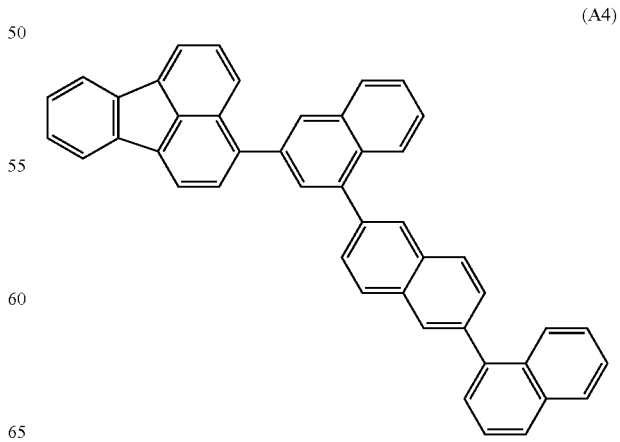

(A5)
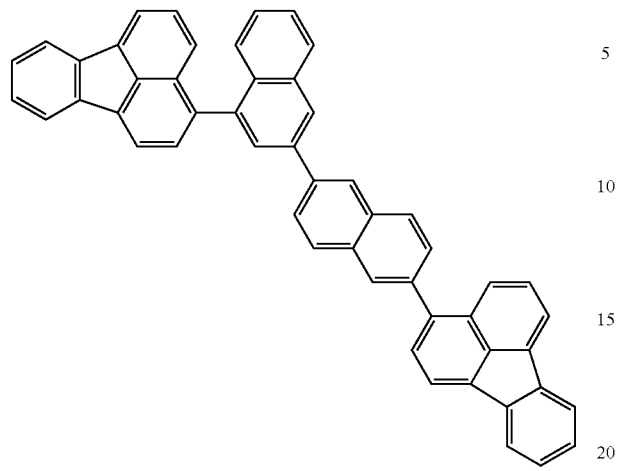
(A6)
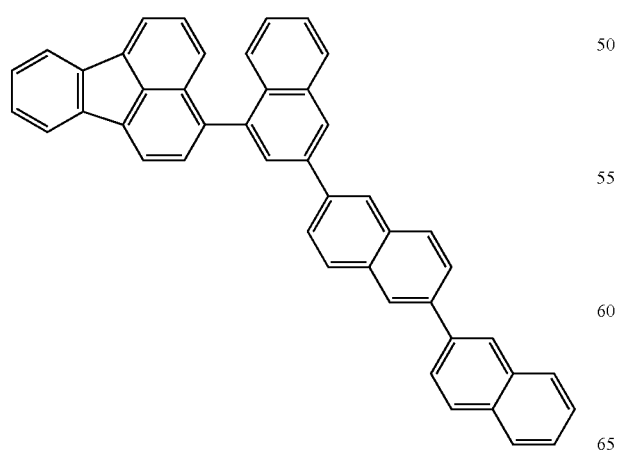
(A8)
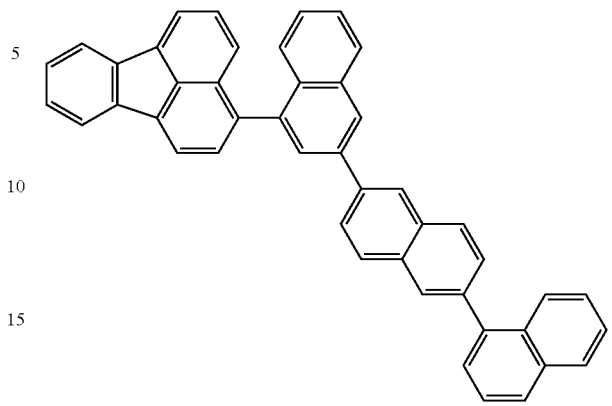
(A9)
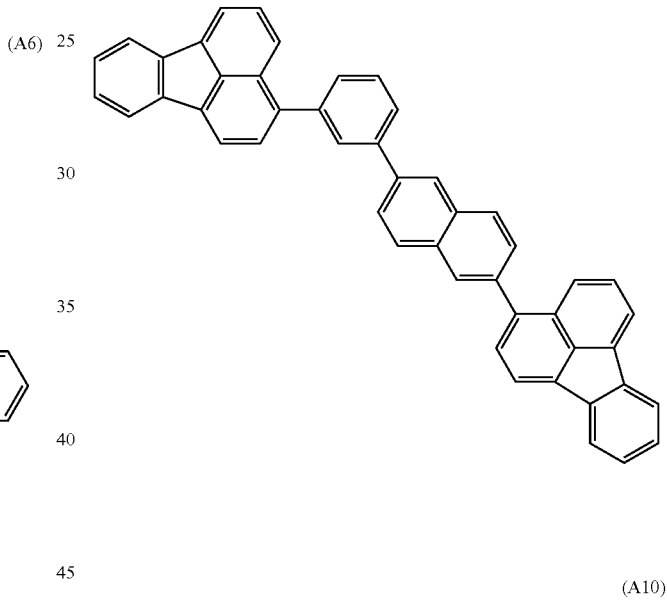

(A11)
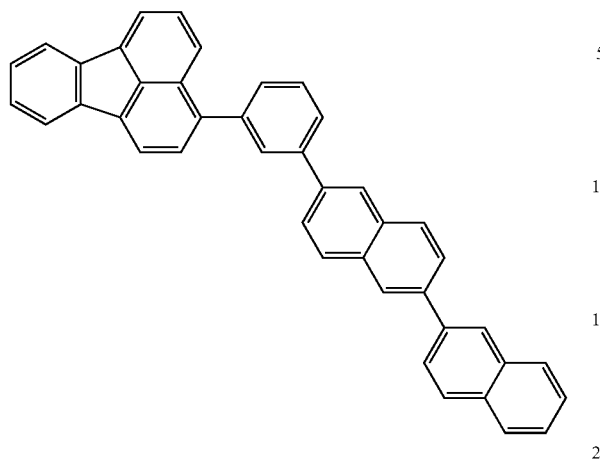
(A14)
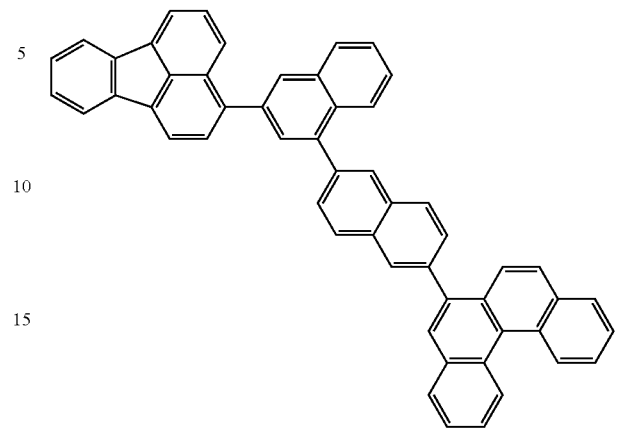
(A12)
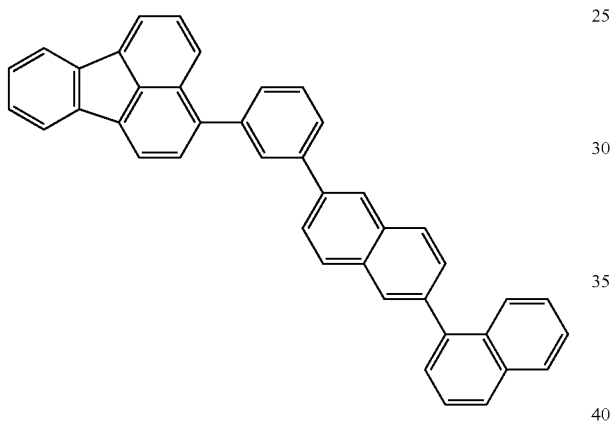
(A15)
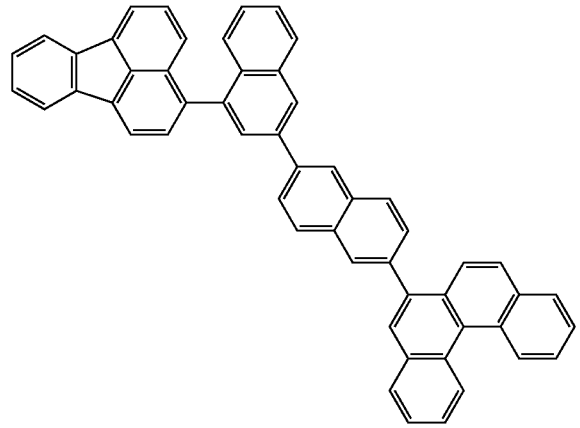
(A13)
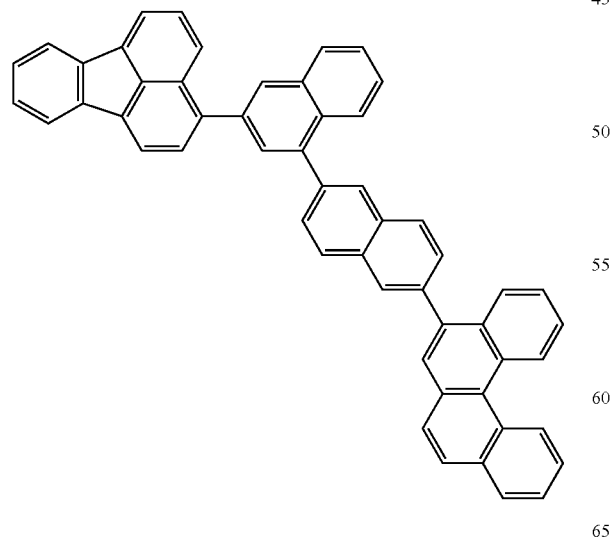
(A16)
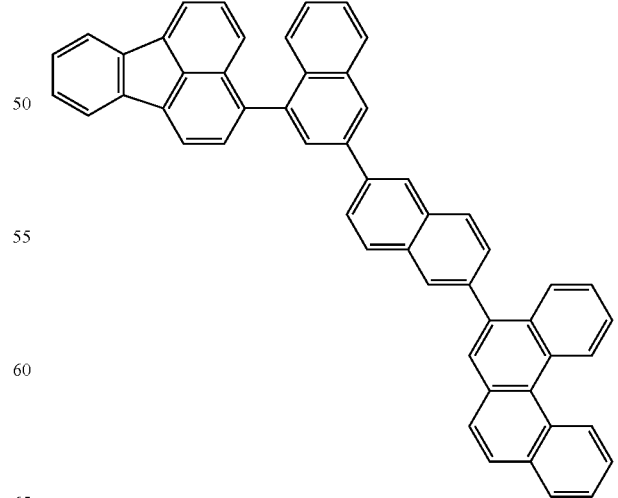

-continued
(A17)
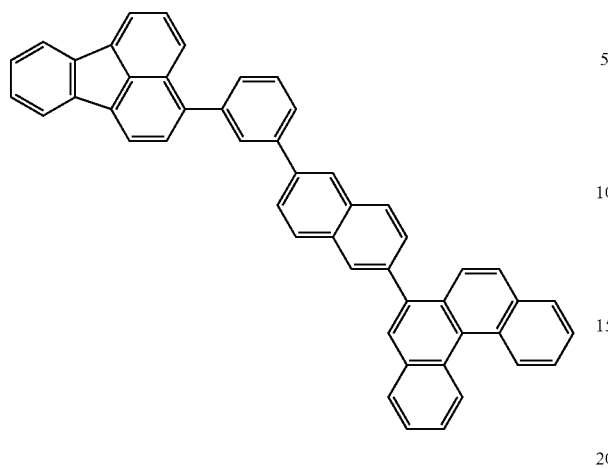
(A18)
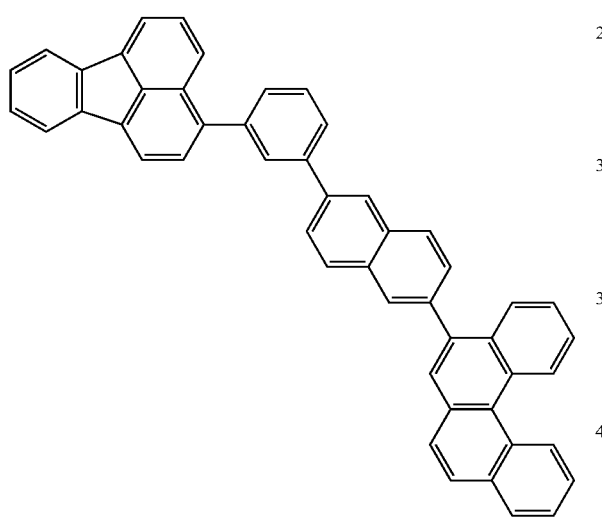
(A19)
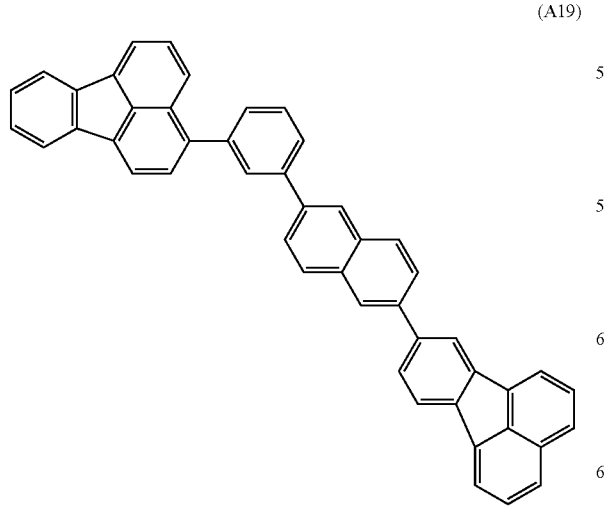
-continued
(A20)
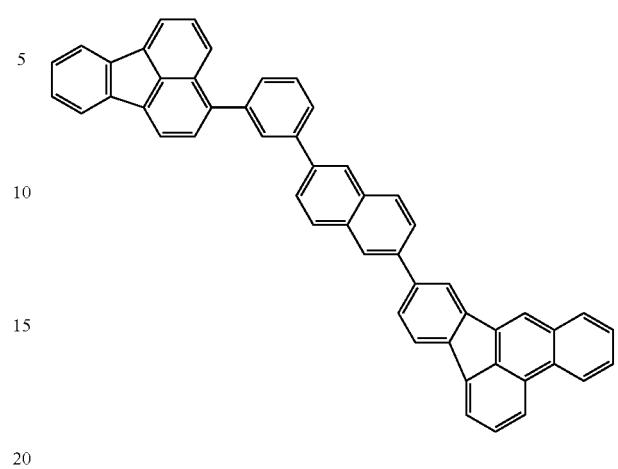
(A21)
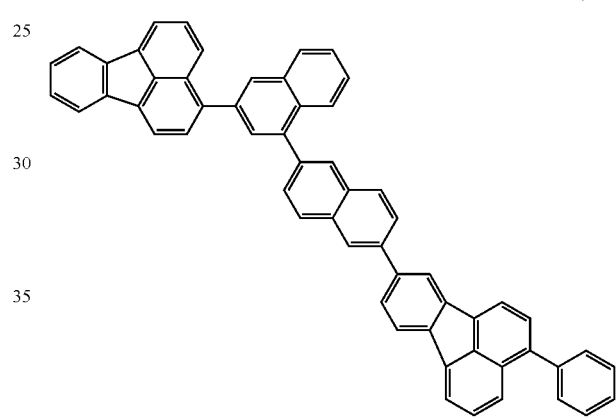
(A22)
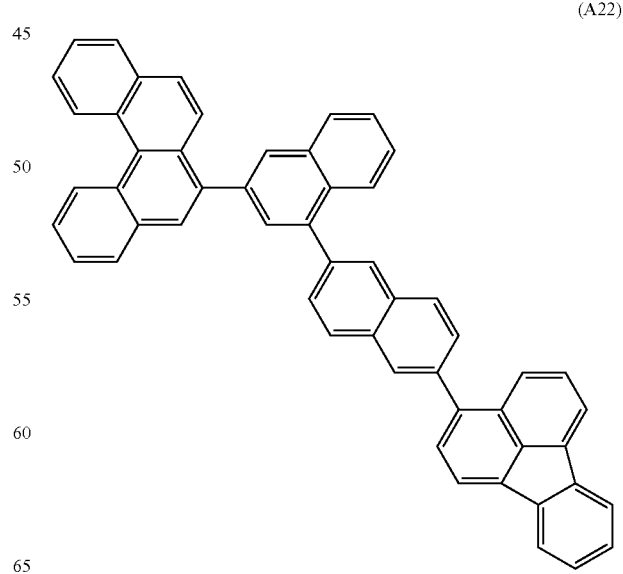

(A23)
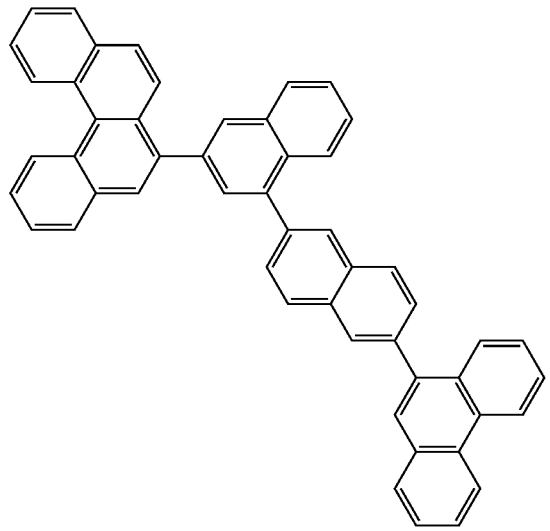
(A24)
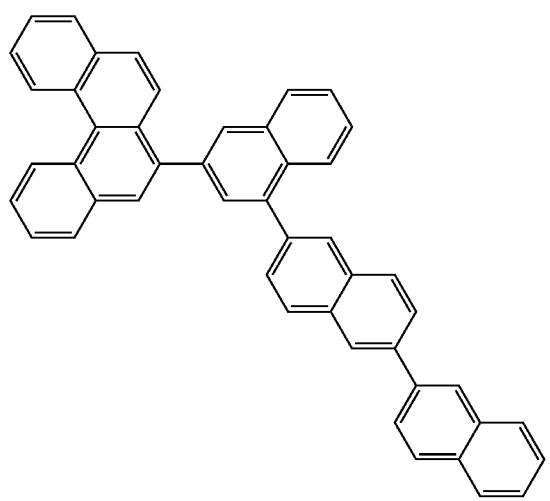
(A25)
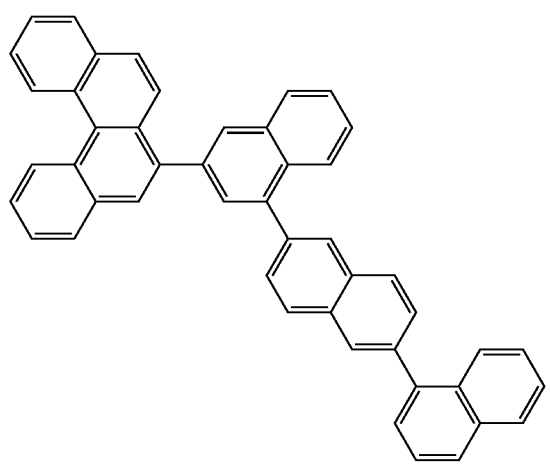
(A26)
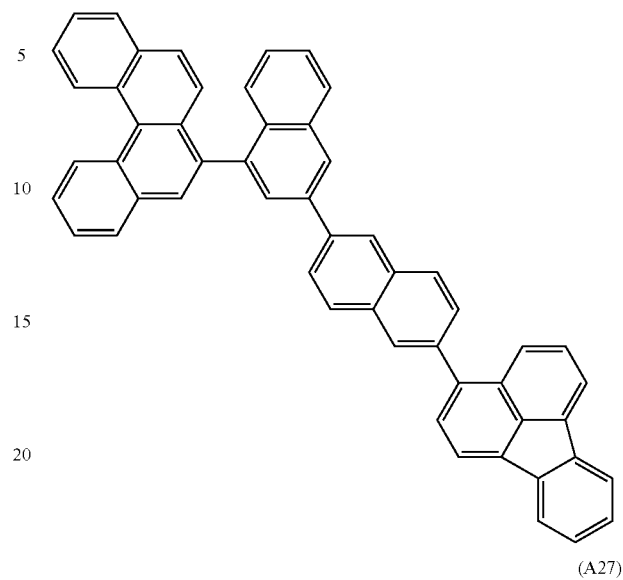
(A27)
(A28)
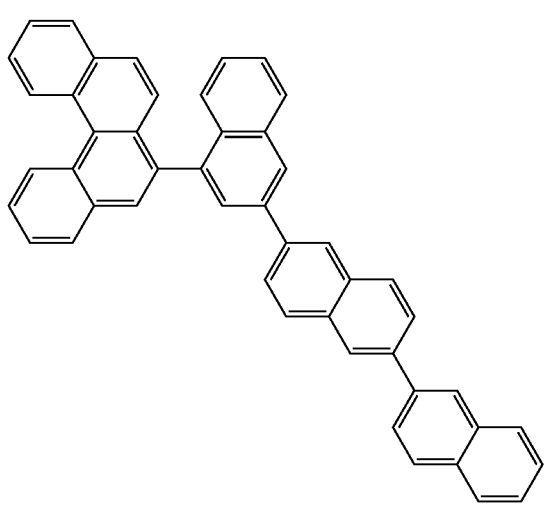

(A29)
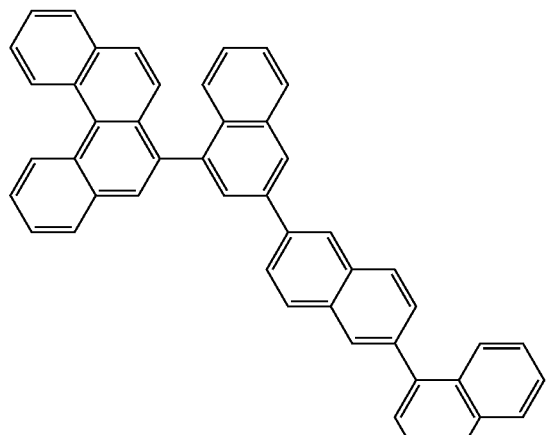
(A30)
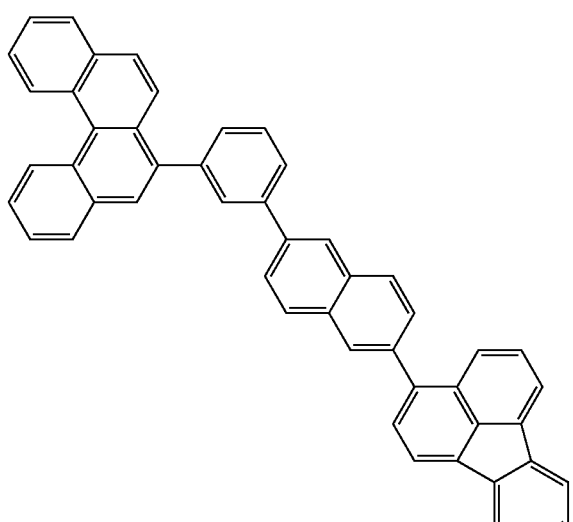
(A31)
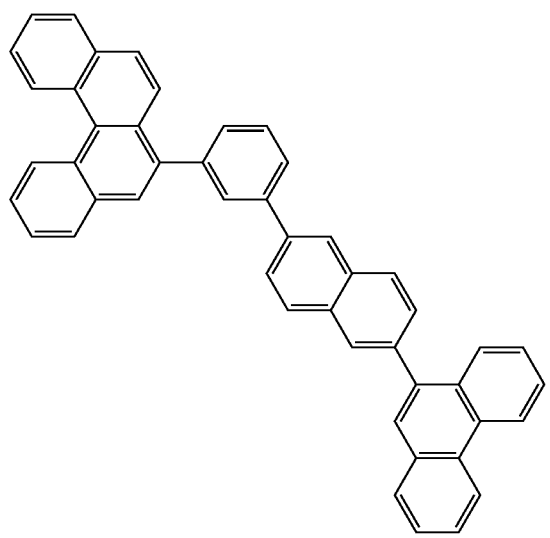
(A32)
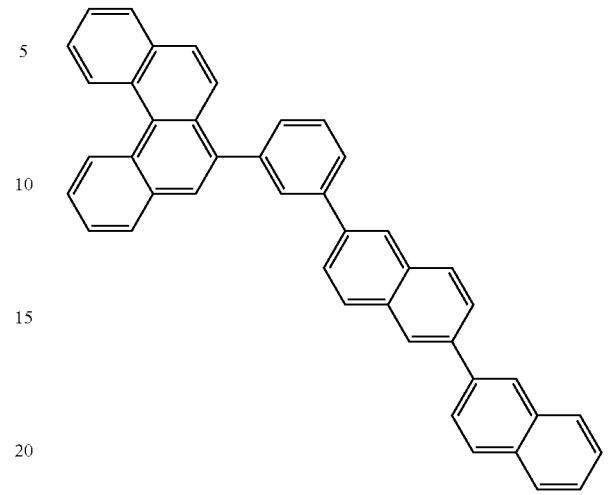
(A33)
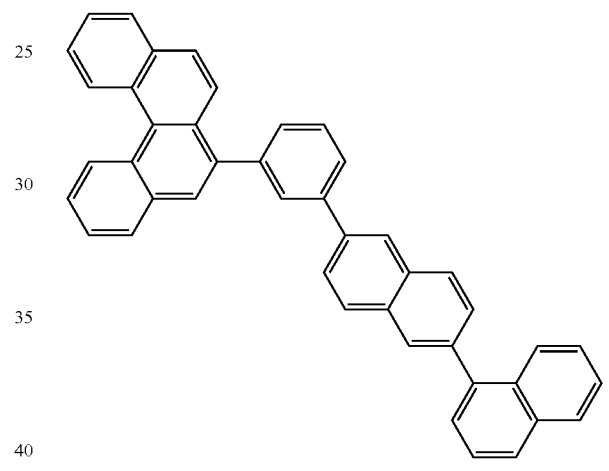
(34)
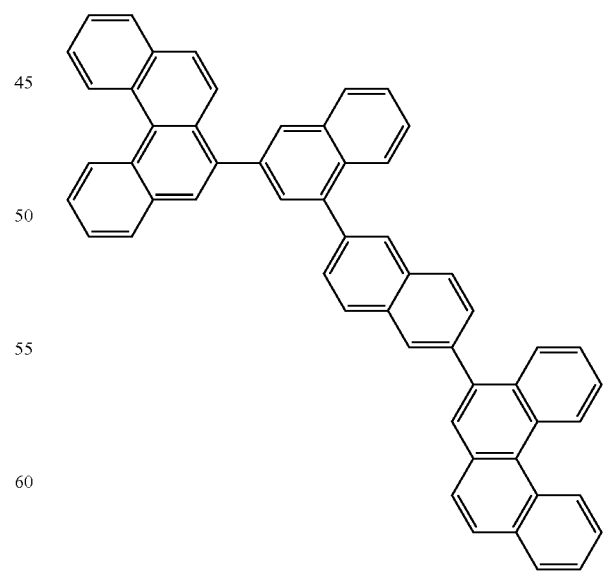

(A35)
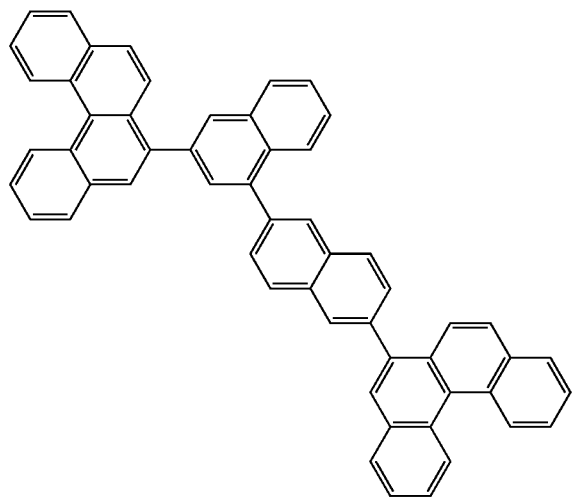
(A36)
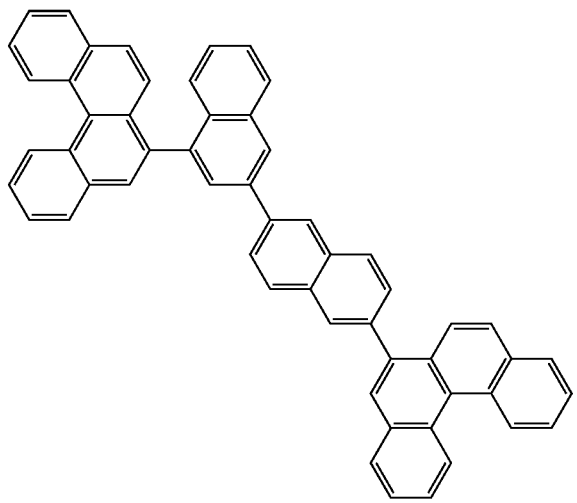
(A37)
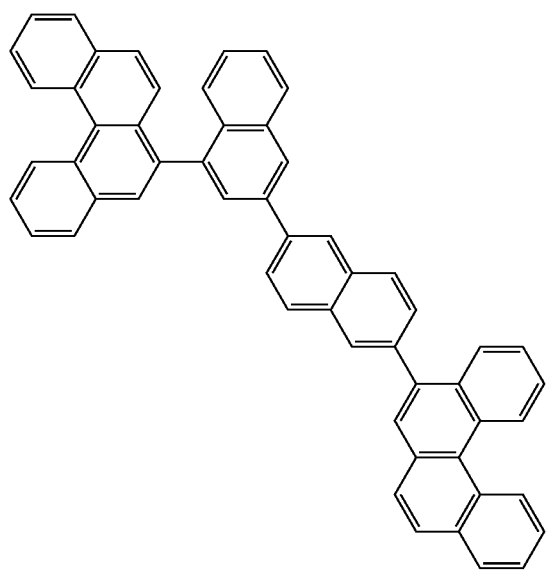
(A38)
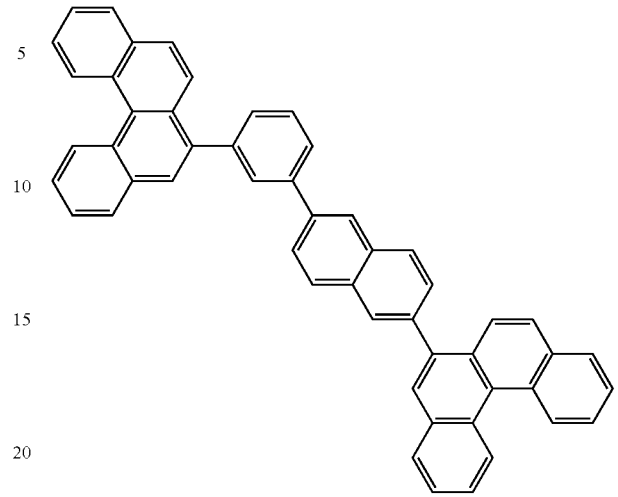
(A39)
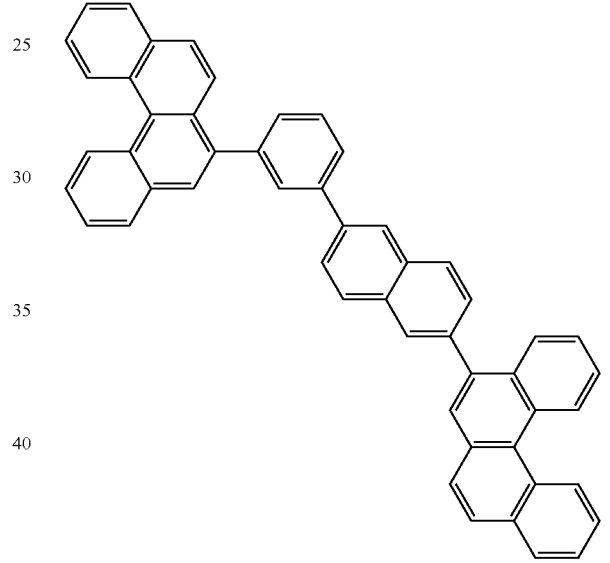
(A40)
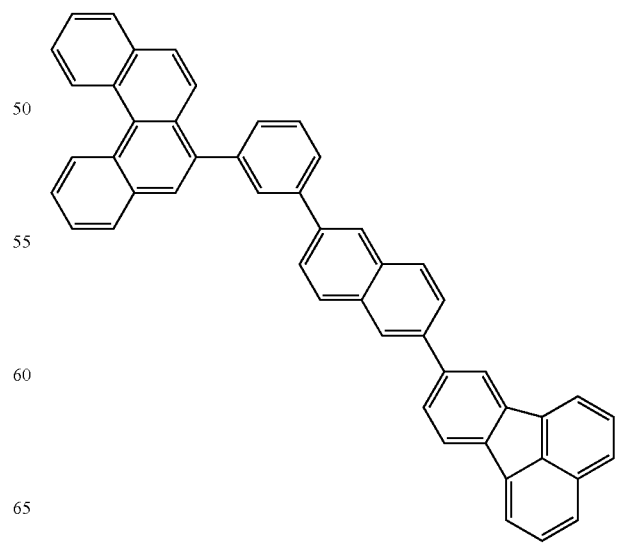

(A41)
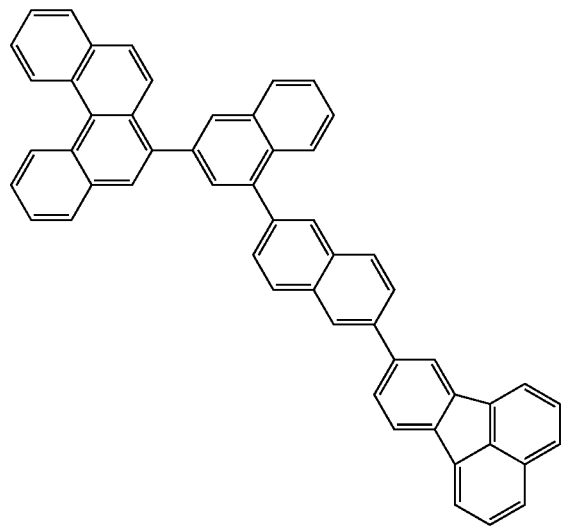
(A44)
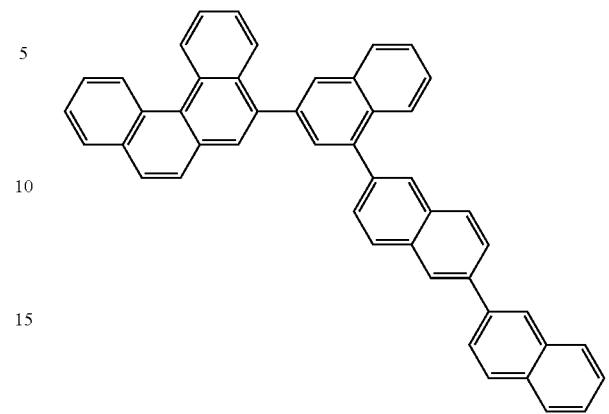
(A42)
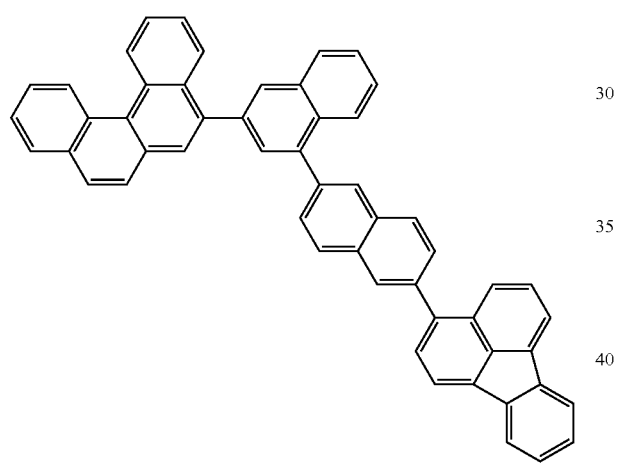
(A45)
(A43)
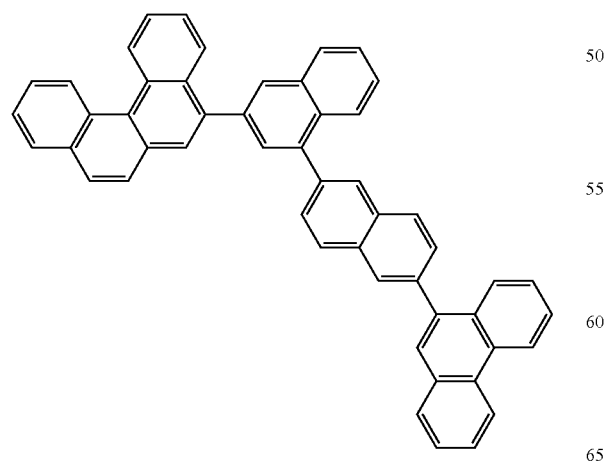
(A46)
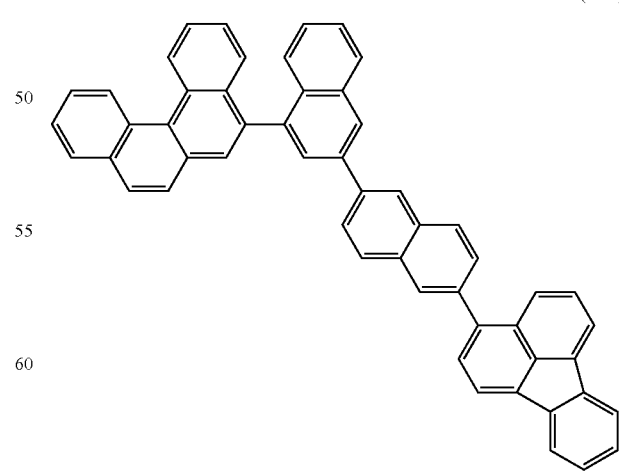

(A47)
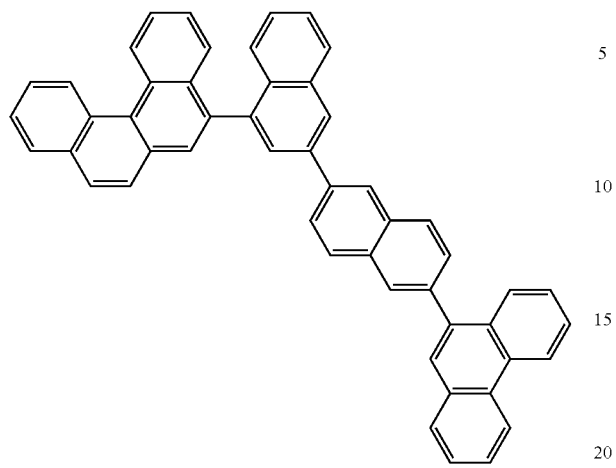
(A50)
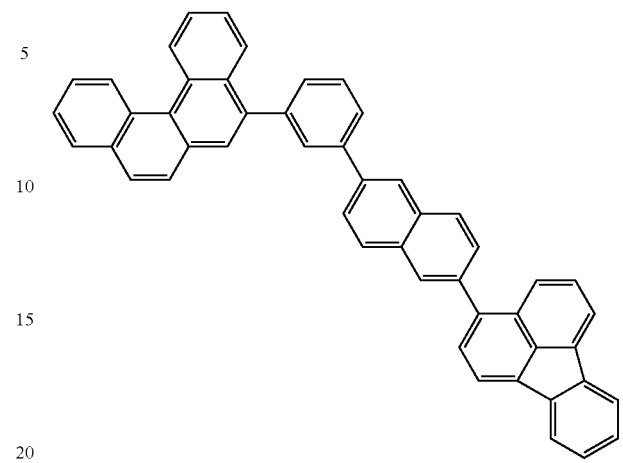
(A48)
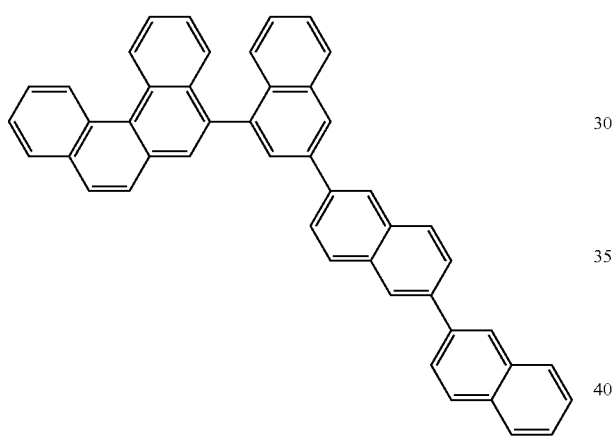
(A51)
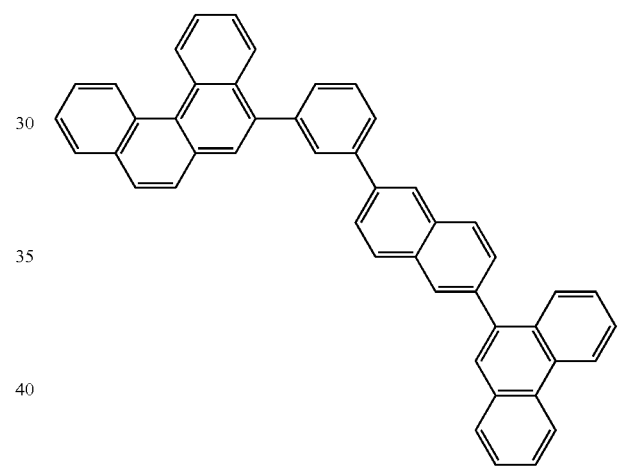
(A49)
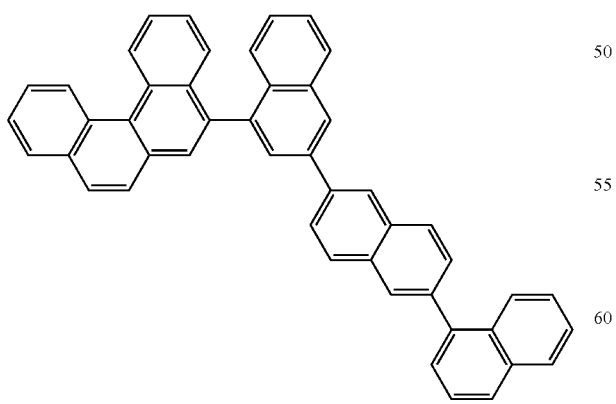
(A52)
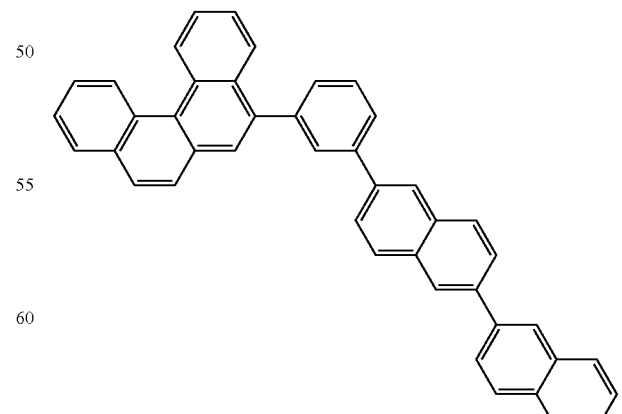

(A53)
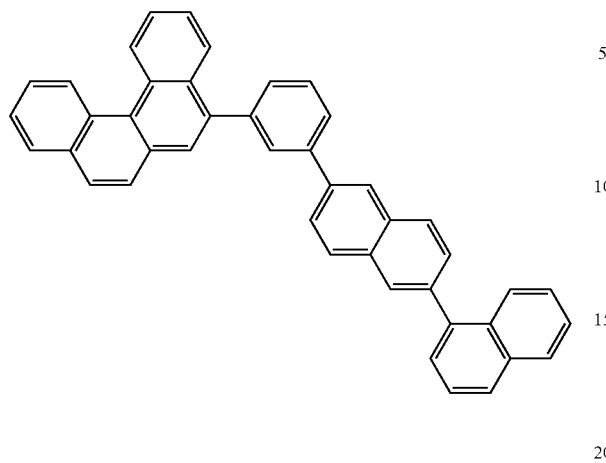
(A54)
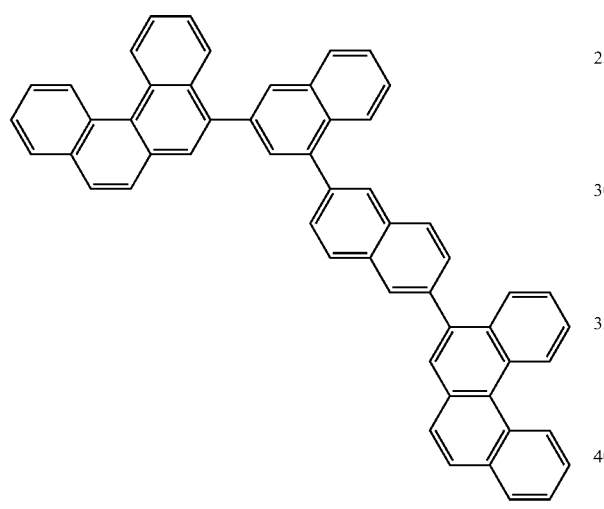
(A55)
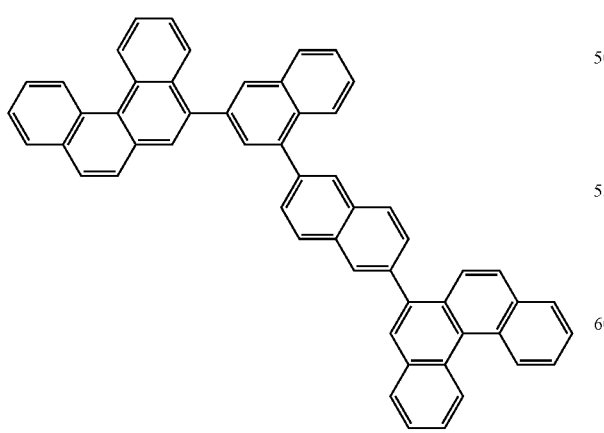
(A56)
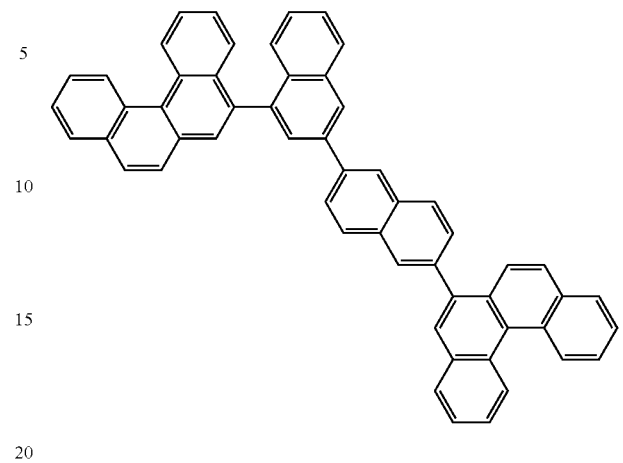
(A57)
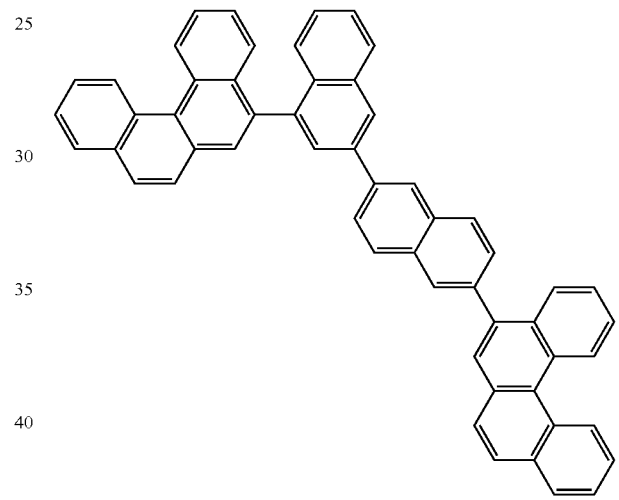
(A58)
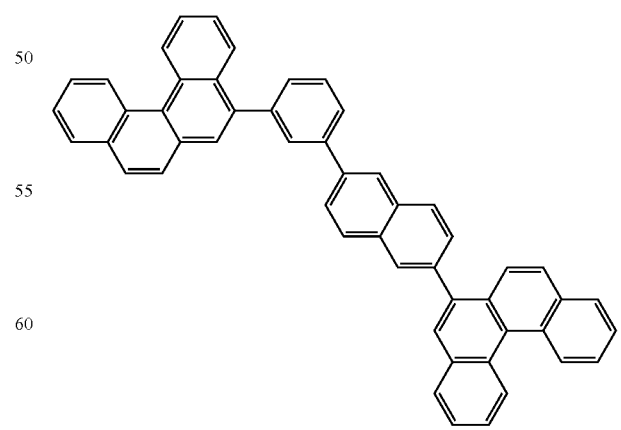

-continued
(A59)
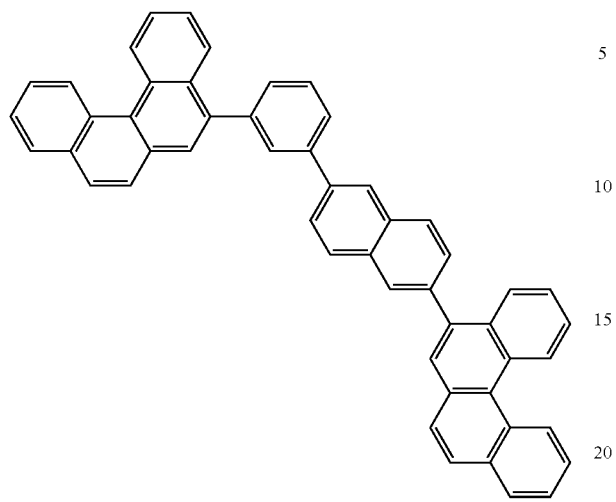
(A60)
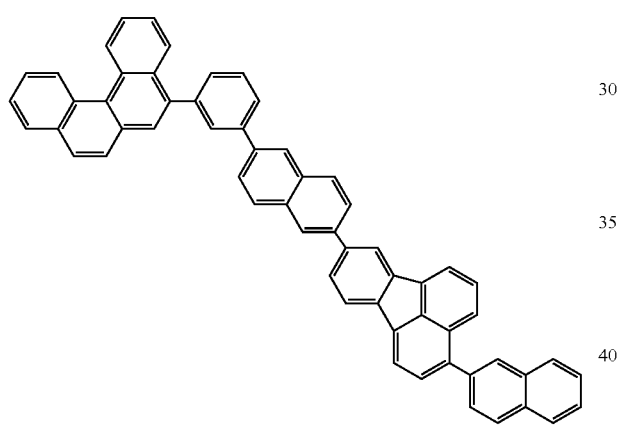
(A61)
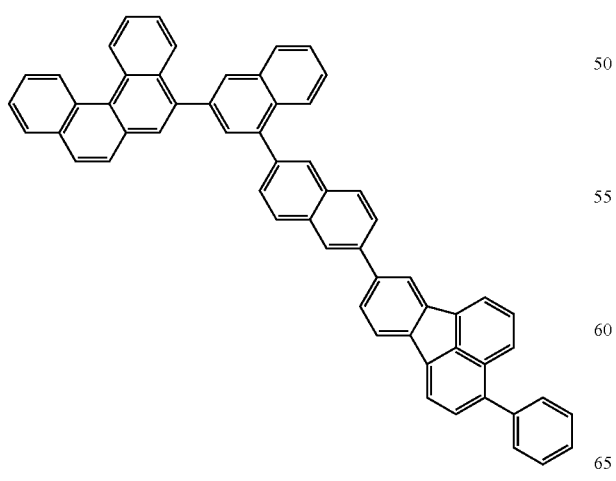
-continued
(A62)
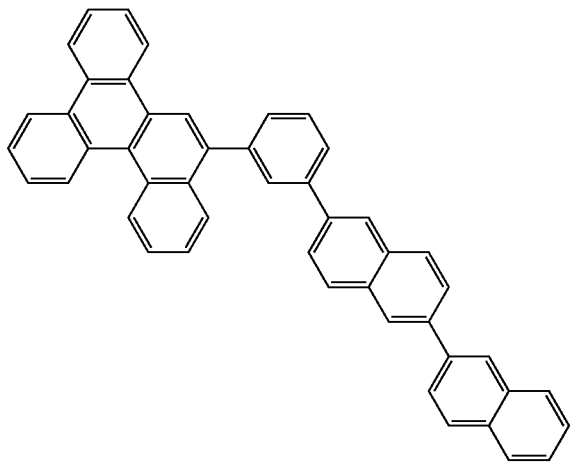
(A63)
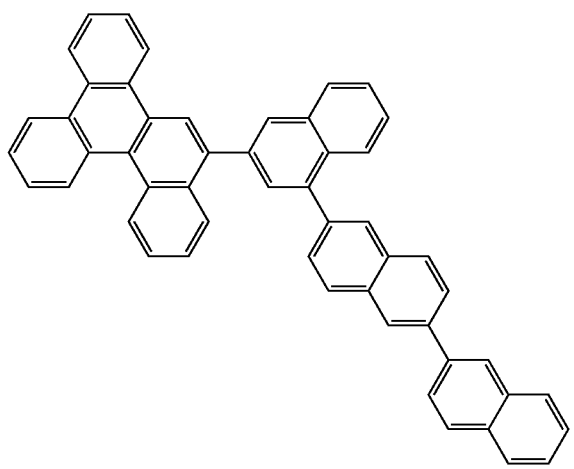
(A64)
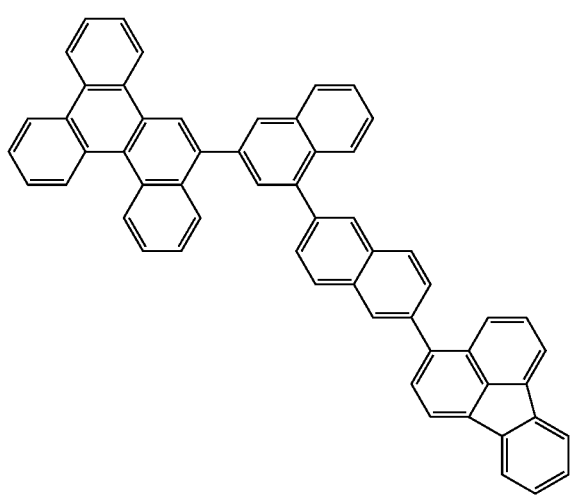

-continued (A65)
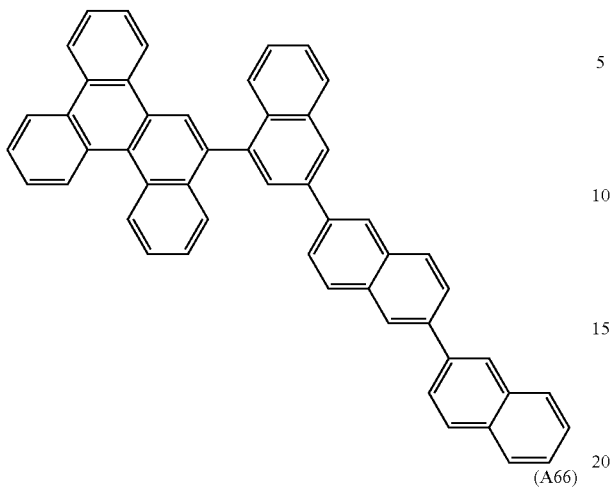

(A66)
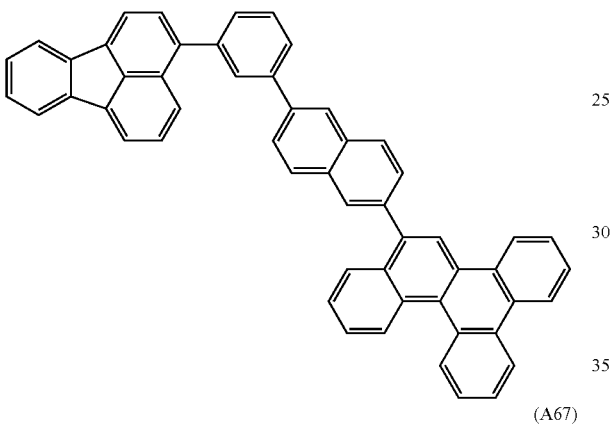

(A67)
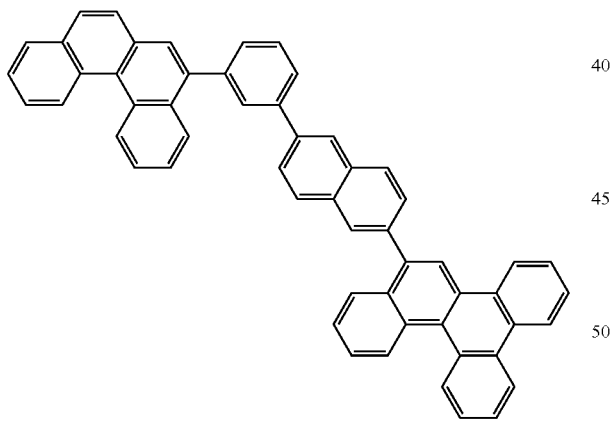

(Phosphorescent Material)

The phosphorescent material used in the invention, which generates phosphorescent emission, preferably contains a metal complex. The metal complex is preferably a metal complex having: a metal atom selected from Ir, Pt, Os, Au, Re and Ru; and a ligand. Particularly, the ligand preferably has an ortho-metal bond.

The phosphorescent material is preferably a compound containing a metal selected from iridium (Ir), osmium (Os) and platinum (Pt) because such a compound, which exhibits high phosphorescence quantum yield, can further enhance external quantum efficiency of the emitting device. The phosphorescent material is more preferably a metal complex such as an iridium complex, an osmium complex or a platinum complex, among which an iridium complex and a platinum complex are more preferable and ortho metalation of an iridium complex is the most preferable.

Examples of the metal complex are shown below, among which metal complexes that emit green to red light are particularly preferable.

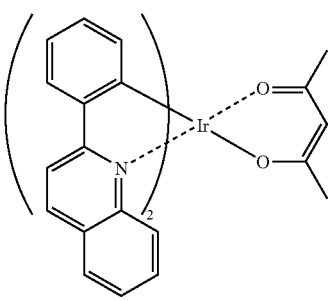

PQIr

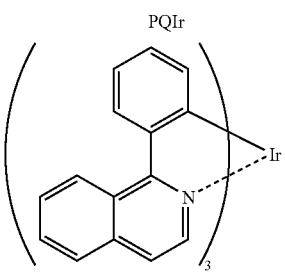

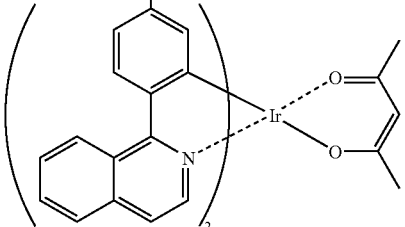

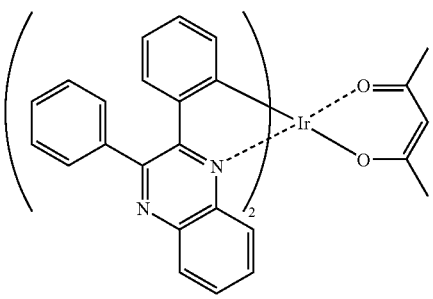

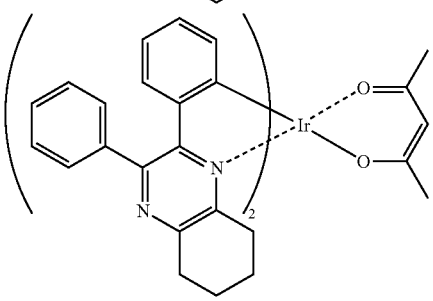

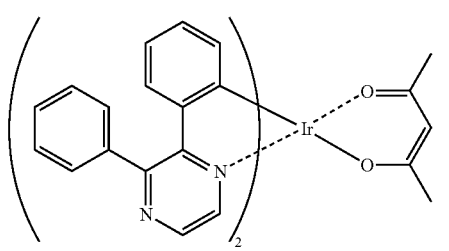
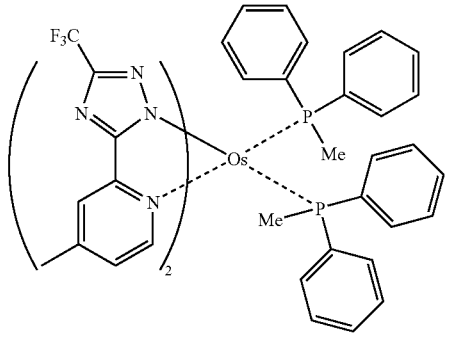
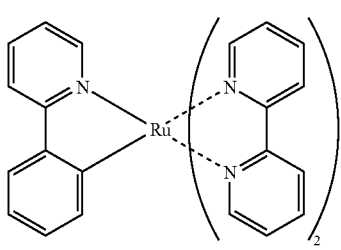
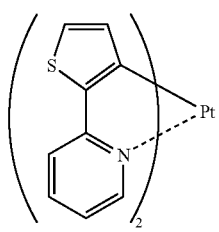
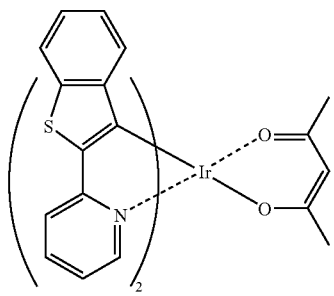
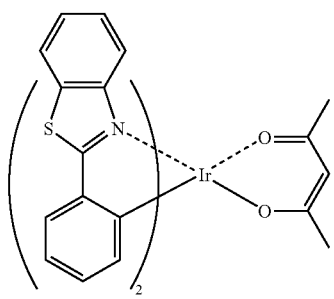
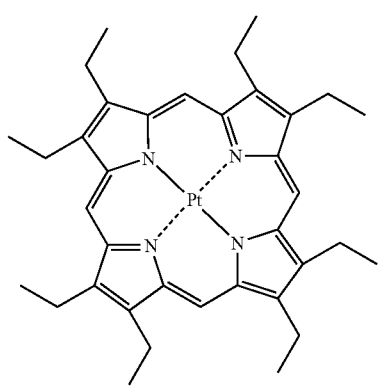
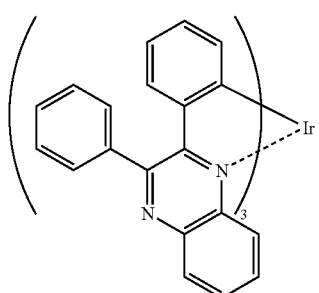
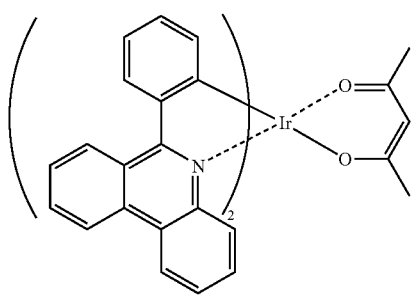
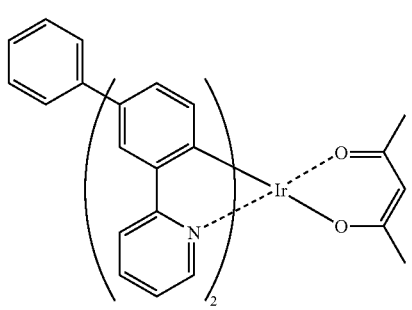
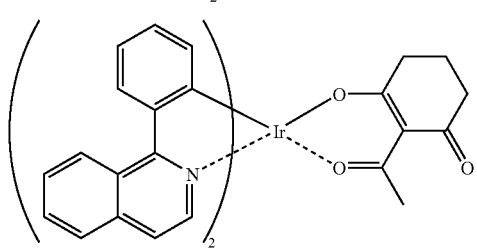

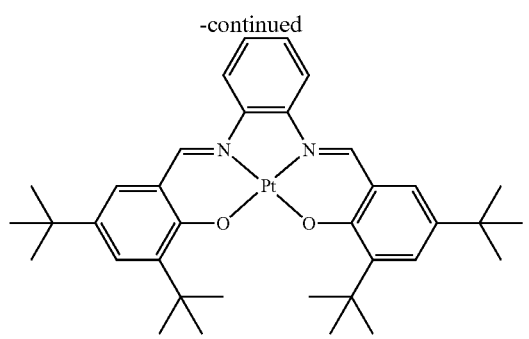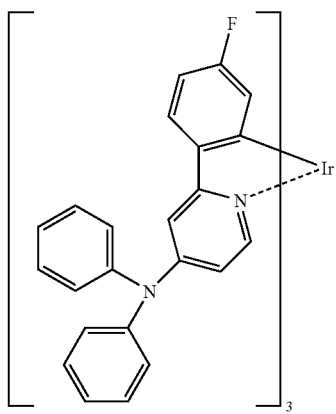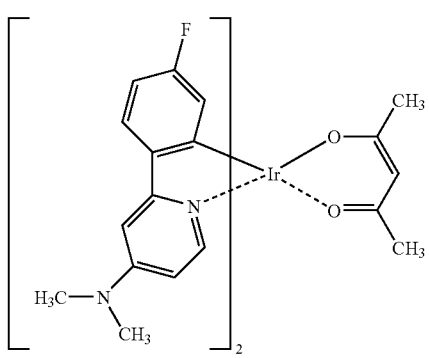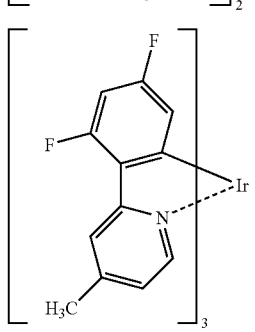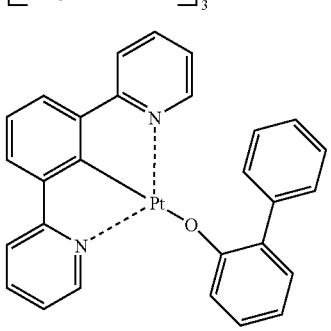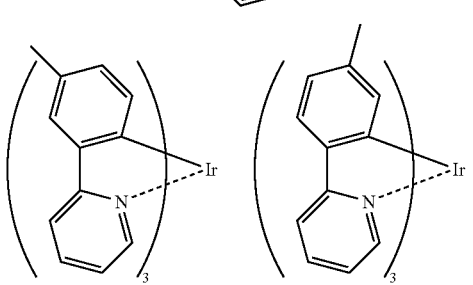

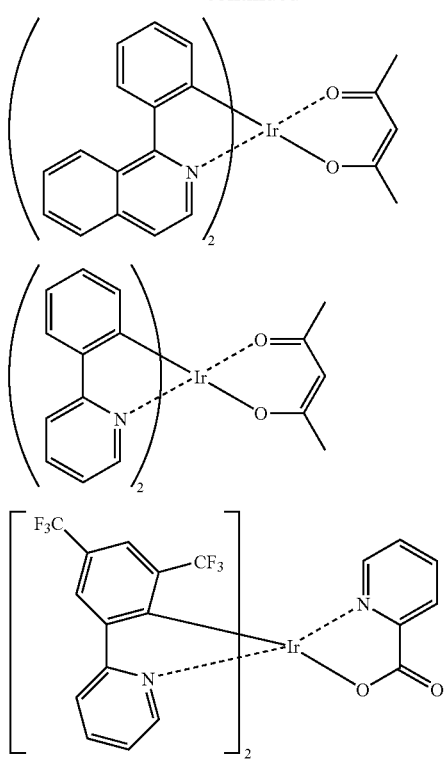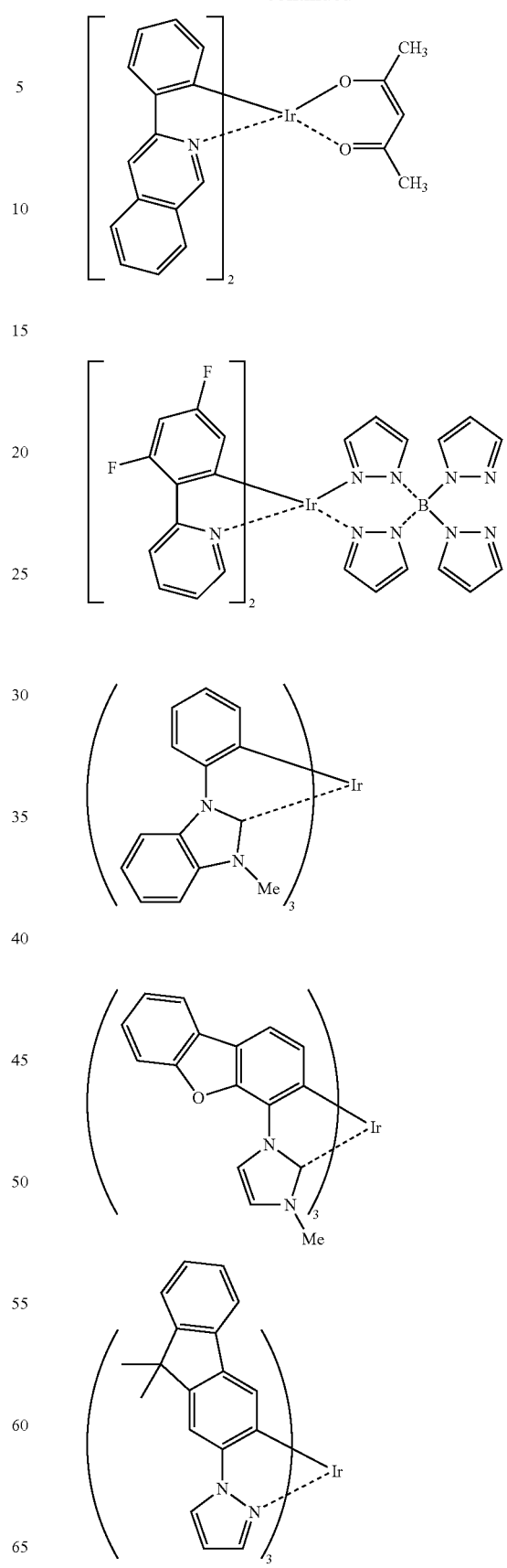

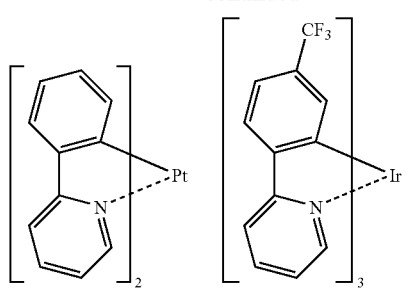
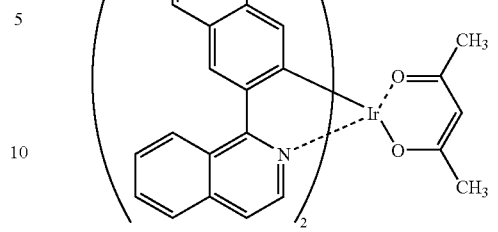
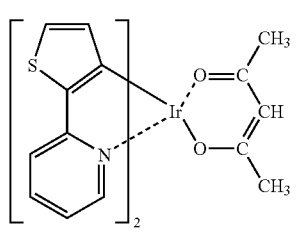
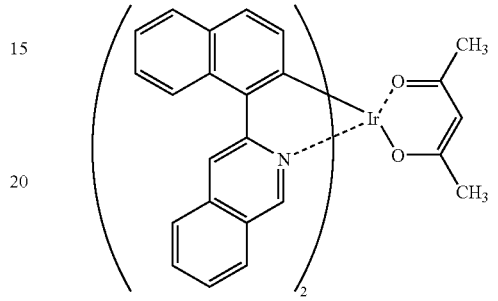
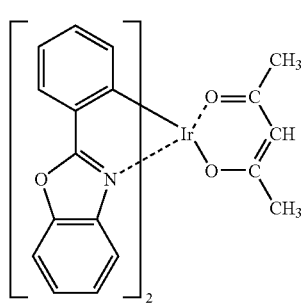
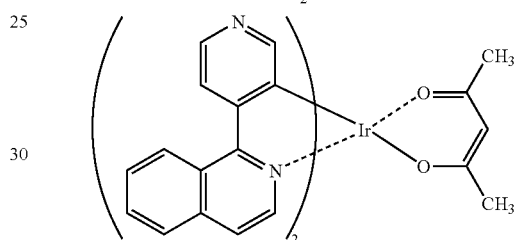
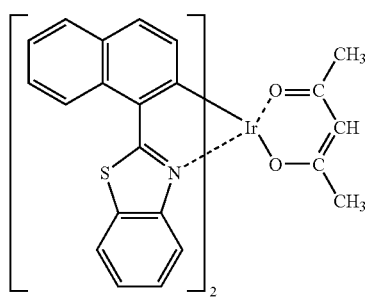
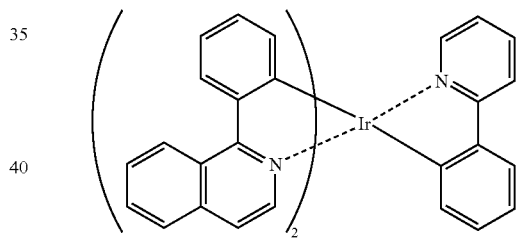
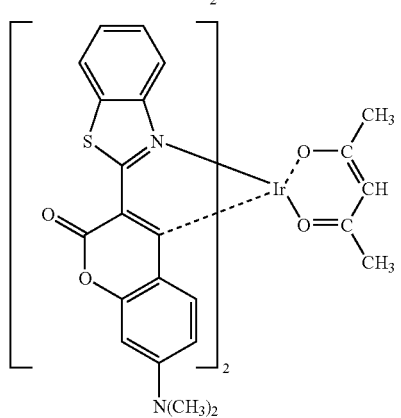
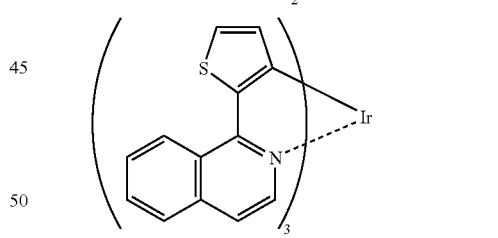
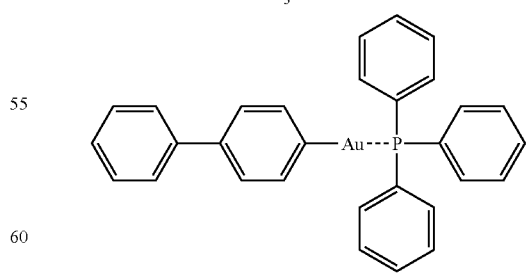
In the invention, at least one phosphorescent material contained in the emitting layer preferably emits light having the maximum wavelength of 520 to 720 nm, more preferably light having the maximum wavelength of 570 nm to 720 nm.

By doping the phosphorescent material (phosphorescent dopant) having such an emission wavelength to the specific host material usable for the invention so as to form the emitting layer, the organic EL device can exhibit high efficiency.

The organic EL device according to the aspect of the invention may include a hole transporting layer (hole injecting layer), and the hole transporting layer (hole injecting layer) may preferably contain the organic-EL-device material represented by the formula (1), (2) or (3).

The organic EL device according to the aspect of the invention may include an electron transporting layer (electron injecting layer), and the electron transporting layer (electron injecting layer) may preferably contain the organic-EL-device material represented by the formula (1), (2) or (3).

The organic EL device according to the aspect of the invention may include an electron blocking layer and a hole blocking layer, and the electron blocking layer and the hole blocking layer may preferably contain the organic-EL-device material represented by the formula (1), (2) or (3).

In the organic EL device according to the aspect of the invention, a reductive dopant may be preferably contained in an interfacial region between the cathode and the organic thin-film layer.

With this arrangement, the organic EL device can emit light with enhanced luminance intensity and have a longer lifetime.

The reductive dopant may be at least one compound selected from an alkali metal, an alkali metal complex, an alkali metal compound, an alkali earth metal, an alkali earth metal complex, an alkali earth metal compound, a rare-earth metal, a rare-earth metal complex, a rare-earth metal compound and the like.

Examples of the alkali metal are Na (work function: 2.36 eV), K (work function: 2.28 eV), Rb (work function: 2.16 eV), Cs (work function: 1.95 eV) and the like, among which a substance having a work function of 2.9 eV or less is particularly preferable. Among the above, the reductive dopant is preferably K, Rb or Cs, more preferably Rb or Cs, the most preferably Cs.

Examples of the alkali earth metal are Ca (work function: 2.9 eV), Sr (work function: 2.0 to 2.5 eV), Ba (work function: 2.52 eV), and the like, among which a substance having a work function of 2.9 eV or less is particularly preferable.

Examples of the rare-earth metal are Sc, Y, Ce, Tb, Yb and the like, among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound are an alkali oxide such as $Li_2O$, $Cs_2O$ or $K_2O$, an alkali halogen compound such as LiF, NaF, CsF or KF and the like, among which LiF, $Li_2O$ and NaF are preferable.

Examples of the alkali earth metal compound are BaO, SrO, CaO, a mixture thereof such as $Ba_xSr_{1-x}O$ ($0<x<1$) or $Ba_xCa_{1-x}O$ ($0<x<1$) and the like, among which BaO, SrO and CaO are preferable.

Examples of the rare-earth metal compound are $YbF_3$, $ScF_3$, $ScO_3$, $Y_2O_3$, $Ce_2O_3$, $GdF_3$, $TbF_3$ and the like, among which $YbF_3$, $ScF_3$ and $TbF_3$ are preferable.

The alkali metal complex, the alkali earth metal complex and the rare-earth metal complex are not specifically limited, as long as at least one of alkali metal ion, alkali earth metal ion and rare-earth metal ion is contained therein as metal ion. The ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The reductive dopant is added to preferably form a layer or an island pattern in the interfacial region. The layer of the reductive dopant or the island pattern of the reductive dopant is preferably formed by depositing the reductive dopant by resistance heating deposition while an emitting material for forming the interfacial region or an organic substance as an electron-injecting material are simultaneously deposited, so that the reductive dopant is dispersed in the organic substance. Dispersion concentration at which the reductive dopant is dispersed in the organic substance is a mole ratio (organic substance to reductive dopant) of 100:1 to 1:100, preferably 5:1 to 1:5.

When the reductive dopant forms the layer, the emitting material or the electron injecting material for forming the organic layer of the interfacial region is initially layered, and the reductive dopant is subsequently deposited singularly thereon by resistance heating deposition to form a preferably 0.1 to 15 nm-thick layer.

When the reductive dopant forms the island pattern, the emitting material or the electron injecting material for forming the organic layer of the interfacial region is initially formed in an island shape, and the reductive dopant is subsequently deposited singularly thereon by resistance heating deposition to form a preferably 0.05 to 1 nm-thick island shape.

A ratio of the main component to the reductive dopant in the organic EL device according to the aspect of the invention is preferably a mole ratio (main component to reductive dopant) of 5:1 to 1:5, more preferably 2:1 to 1:2.

The organic EL device according to the aspect of the invention preferably includes the electron transporting layer or the electron injecting layer between the emitting layer and the cathode, and the electron transporting layer or the electron injecting layer preferably contains the above organic-EL-device material. The electron transporting layer or the electron injecting layer more preferably contains the above organic-EL-device material as the main component. The electron injecting layer may serve also as the electron transporting layer.

It should be noted that "as the main component" means that the organic-EL-device material is contained in the electron injecting layer with a content of 50 mass % or more.

The electron injecting layer or the electron transporting layer, which aids injection of the electrons into the emitting layer, has a high electron mobility. The electron injecting layer is provided for adjusting energy level, by which, for instance, sudden changes of the energy level can be reduced.

A preferable example of an electron transporting material for forming the electron transporting layer or the electron injecting layer is an aromatic heterocyclic compound having in the molecule at least one heteroatom. Particularly, a nitrogen-containing cyclic derivative is preferable. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

A preferable example of the nitrogen-containing cyclic derivative is a nitrogen-containing cyclic metal chelate complex represented by the following formula (A).

(A)

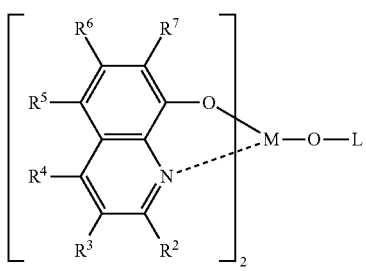

In the formula, $R^2$ to $R^7$ each independently represent a hydrogen atom, a halogen atom, an oxy group, an amino group, a hydrocarbon group having 1 to 40 carbon atoms, an alkoxy group, an aryloxy group, an alkoxycarbonyl group or a heterocyclic group. $R^2$ to $R^7$ may be substituted or unsubstituted.

Examples of the halogen atom are fluorine, chlorine, bromine, iodine and the like. Examples of a substituted or unsubstituted amino group are an alkylamino group, an arylamino group and an aralkylamino group.

Examples of the hydrocarbon group having 1 to 40 carbon atoms are a substituted or unsubstituted alkyl group, an alkenyl group, a cycloalkyl group, an aryl group, an aralkyl group and the like.

Examples of the alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group and 1,2,3-trinitropropyl group.

Among the above, the alkyl group is preferably a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 1-pentylhexyl group, 1-butylpentyl group or 1-heptyloctyl group.

Examples of the alkenyl group are a vinyl group, allyl group, 1-butenyl group, 2-butenyl group, 3-butenyl group, 1,3-butanedienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group, among which a styryl group, 2,2-phenylvinyl group and 1,2-diphenylvinyl group are preferable.

Examples of the cycloalkyl group are a cyclopentyl group, cyclohexyl group, cyclooctyl group, and 3,5-tetramethylcyclohexyl group, among which cyclohexyl group, cyclooctyl group and 3,5-tetramethylcyclohexyl group are preferable.

The alkoxy group is a group represented by —OY. Examples of Y are the same as the examples described in relation to the alkyl group, and preferable examples of Y are also the same as those described in relation to the alkyl group.

Examples of non-fused aryl group are a phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group, m-quarter-phenyl group and the like.

Among the above, a phenyl group, biphenyl-2-yl group, biphenyl-3-yl group, biphenyl-4-yl group, m-terphenyl-4-yl group, m-terphenyl-3-yl group, m-terphenyl-2-yl group, p-tolyl group, 3,4-xylyl group, m-quarter-phenyl-2-yl group are preferable.

Examples of a fused aryl group are a 1-naphthyl group and 2-naphtyl group.

The heterocyclic group, which may be monocyclic or fused, preferably has 1 to 20 carbon atoms for forming the ring, more preferably 1 to 12 carbon atoms for forming the ring, further preferably 2 to 10 carbon atoms for forming the ring. The heterocyclic group is an aromatic heterocyclic group having at least one heteroatom selected from a nitrogen atom, oxygen atom, sulfur atom and selenium atom. Examples of the heterocyclic group are groups induced by pirrolidine, piperidine, piperazine, morpholine, thiophene, selenophene, furane, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzoimidazole, benzooxazole, benzothiazole, benzotriazole, tetra-aza indene, carbazole, azepine and the like, preferably groups induced by furane, thiophene, pyridine, pyrazine, pyrimidine, pyridazine, triazine, quinoline, phthalazine, naphthyridine, quinoxaline and quinazoline, further preferably groups induced by furane, thiophene, pyridine and quinoline, further more preferably a quinolinyl group.

Examples of the aralkyl group are a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like.

Among the above, a benzyl group, p-cyanobenzyl group, m-cyanobenzyl group, o-cyanobenzyl group, 1-phenylethyl group, 2-phenylethyl group, 1-phenylisopropyl group and 2-phenylisopropyl group are preferable.

The aryloxy group is represented by —OY'. Preferable examples of Y' are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

Among the aryloxy group, the heteroaryloxy group is represented by —OZ'. Examples of Z' are a 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The alkoxycarbonyl group is represented by —COOY'. Examples of Y' are the same as the examples of the alkyl group.

The alkylamino group and the aralkylamino group are represented by —NQ$^1$Q$^2$. Examples for each of Q$^1$ and Q$^2$ are the same as the examples described in relation to the alkyl group and the aralkyl group, and preferable examples for each of Q$^1$ and Q$^2$ are also the same as those described in relation to the alkyl group and the aralkyl group. Either one of Q$^1$ and Q$^2$ may be a hydrogen atom.

The arylamino group is represented by —NAr$^1$Ar$^2$. Examples for each of Ar$^1$ and Ar$^2$ are the same as the examples described in relation to the non-fused aryl group and the fused aryl group. Either one of Ar$^1$ and Ar$^2$ may be a hydrogen atom.

M represents aluminum (Al), gallium (Ga) or indium (In), among which In is preferable.

L in the formula (A) represents a group represented by the following formula (A') or the following formula (A").

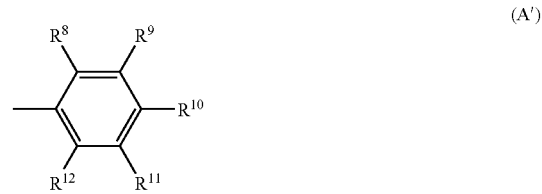

(A')

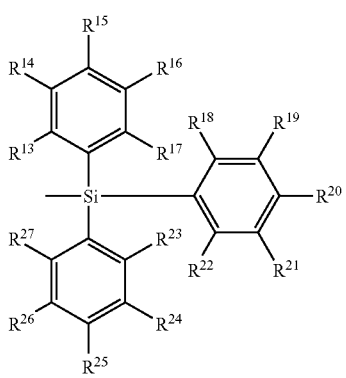
(A″)

In the formula, $R^8$ to $R^{12}$ each independently represent a hydrogen atom or a substituted or unsubstituted hydrocarbon group having 1 to 40 carbon atoms. Adjacent groups may form a cyclic structure. In the formula, $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A″) are the same as those of $R^2$ to $R^7$.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, a diphenylpropane-4,4'-diyl group and the like.

Examples of the nitrogen-containing cyclic metal chelate complex represented by the formula (A) will be shown below. However, the nitrogen-containing cyclic metal chelate complex is not limited to the exemplary compounds shown below.

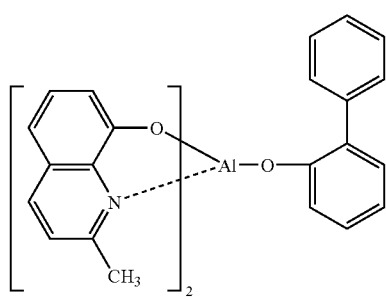
(A-1)

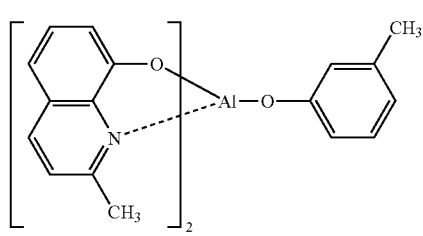
(A-2)

(A-3)

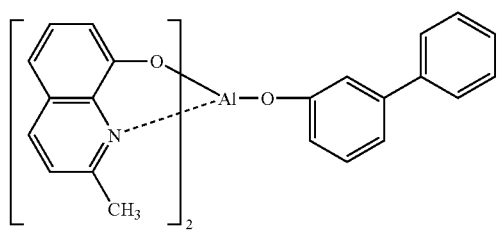
(A-4)

(A-5)

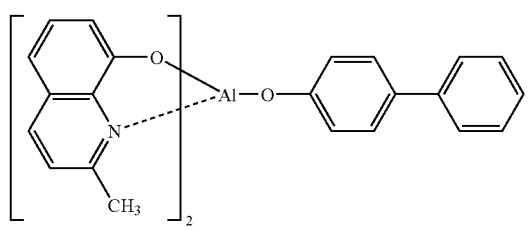
(A-6)

(A-7)

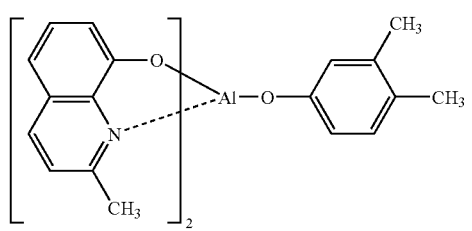
(A-8)

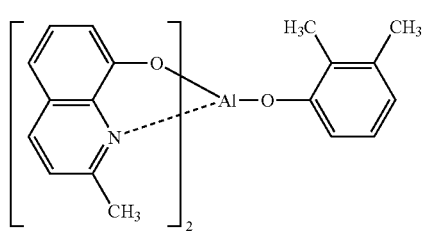
(A-9)

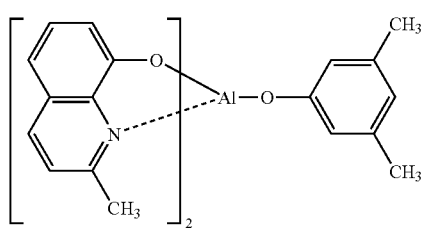 (A-10)
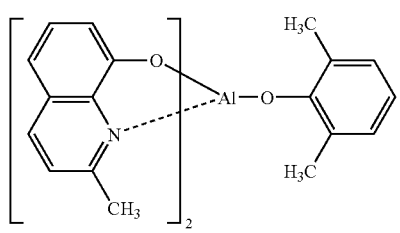 (A-11)
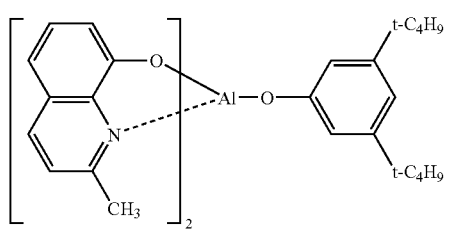 (A-12)
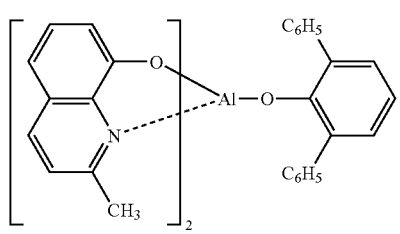 (A-13)
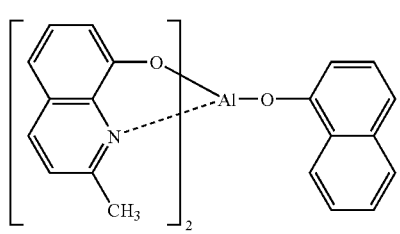 (A-14)
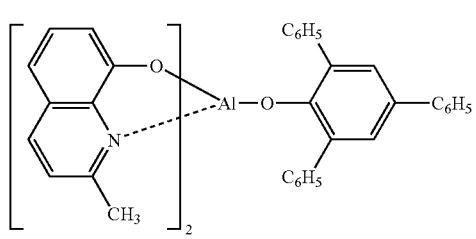 (A-15)
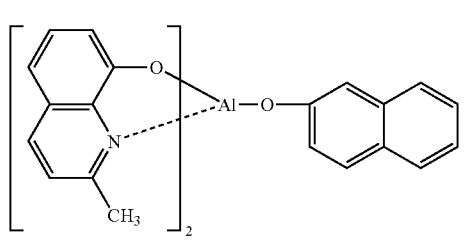 (A-16)
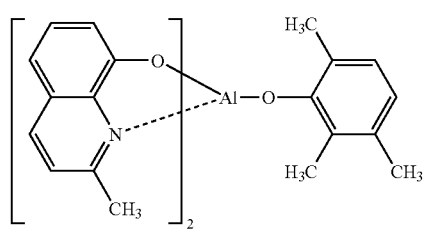 (A-17)
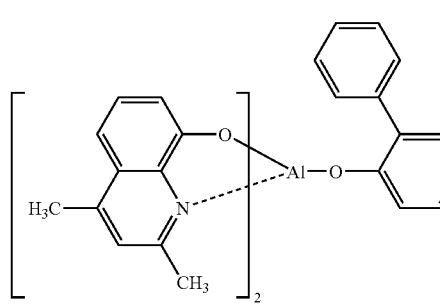 (A-18)
(A-19)
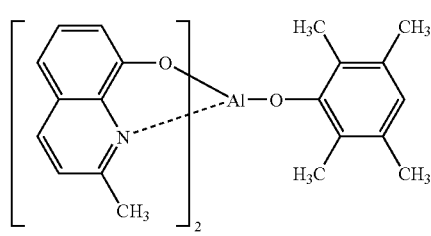 (A-20)
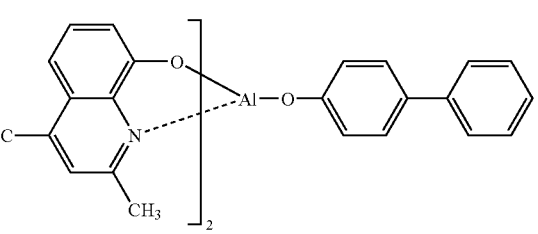 (A-21)
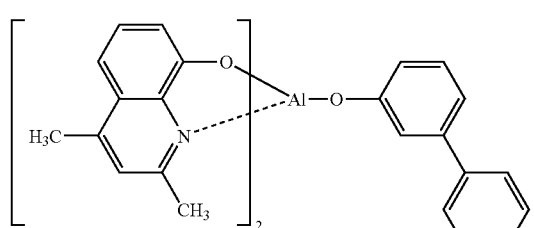 (A-22)

(A-23) 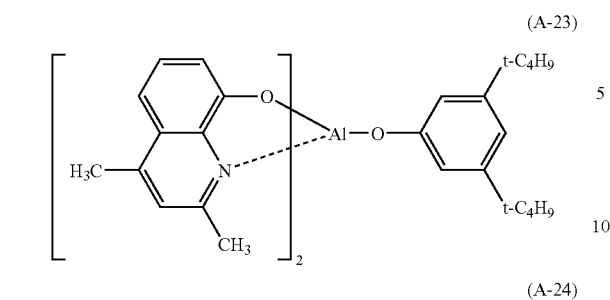
(A-24)
(A-25) 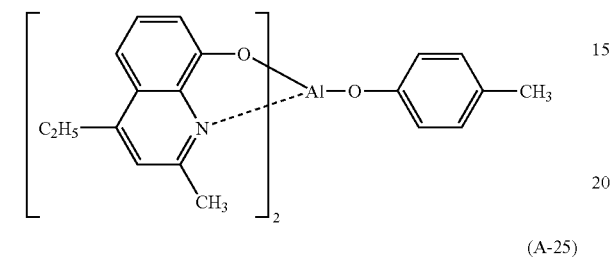
(A-26) 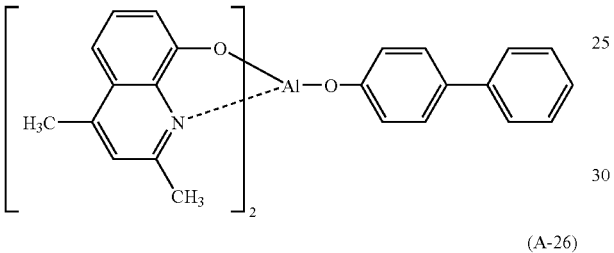
(A-27) 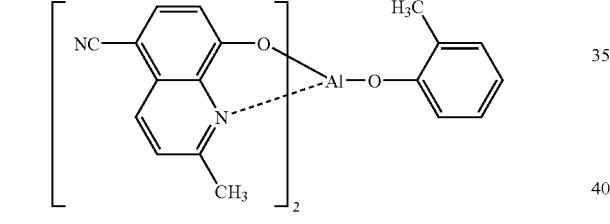
(A-28) 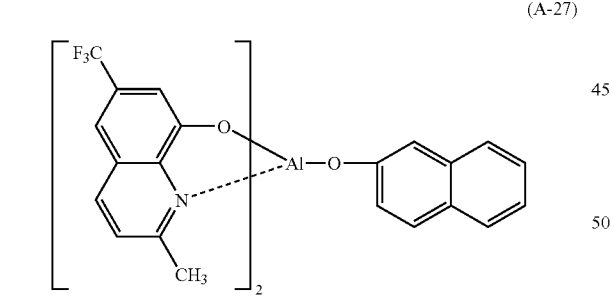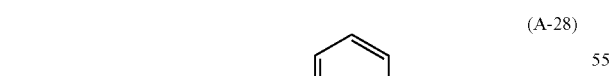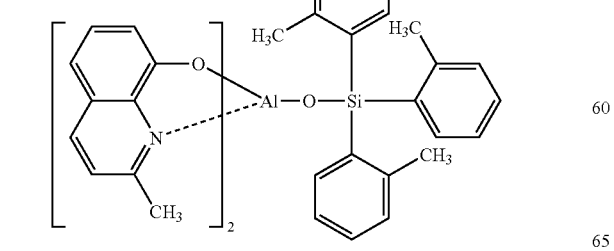
(A-29) 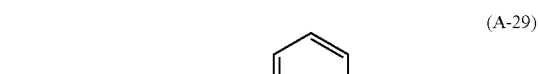
(A-30)
(A-31) 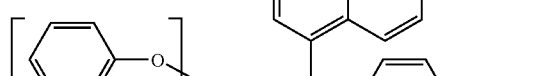
(A-32)
(A-33) 
(A-34) 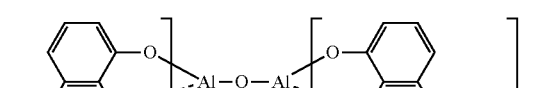

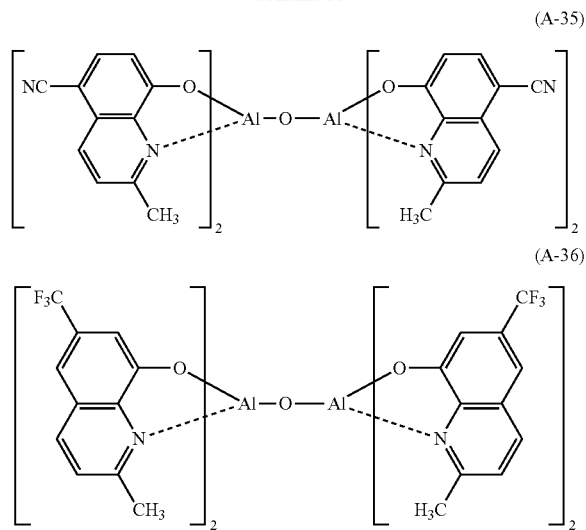

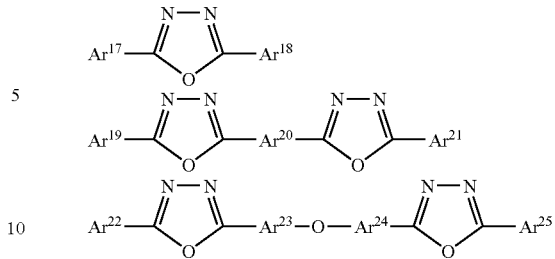

According to the aspect of the invention, the electron injecting layer or the electron transporting layer preferably contains a nitrogen-containing heterocyclic derivative.

In the formula, $Ar^{17}$, $Ar^{18}$, $Ar^{19}$, $Ar^{21}$, $Ar^{22}$ and $Ar^{25}$ each represent a substituted or unsubstituted arylene group. $Ar^{17}$, $Ar^{19}$ and $Ar^{22}$ may be the same as or different from $Ar^{18}$, $Ar^{21}$ and $Ar^{25}$ respectively. $Ar^{20}$, $Ar^{23}$ and $Ar^{24}$ each represent a substituted or unsubstituted arylene group. $Ar^{23}$ and $Ar^{24}$ may be mutually the same or different.

Examples of the arylene group are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group. Such an electron transport compound is preferably an electron transport compound that can be favorably formed into a thin film(s). Examples of the electron transport compounds are as follows.

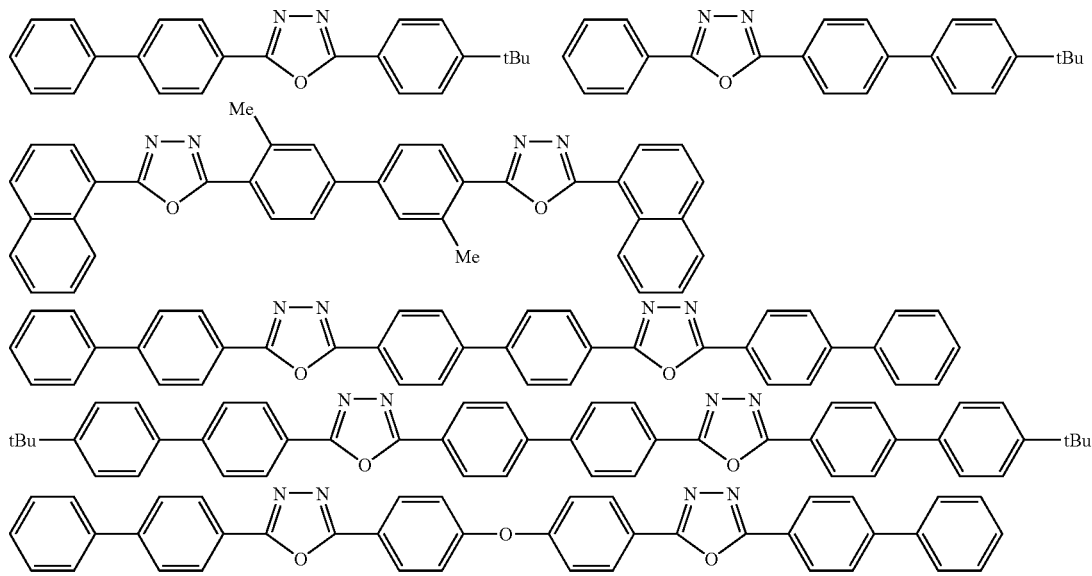

The electron injecting layer or the electron transporting layer, which aids injection of the electrons into the emitting layer, has a high electron mobility. The electron injecting layer is provided for adjusting energy level, by which, for instance, sudden changes of the energy level can be reduced. As a material for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

An example of the nitrogen-containing heterocyclic derivative is a nitrogen-containing heterocyclic derivative that is not a metal complex, the derivative being formed of an organic compound having the following structure. Examples of the nitrogen-containing heterocyclic derivative are five-membered ring or six-membered ring derivative having a skeleton represented by the formula (A) and a derivative having a structure represented by the formula (B).

(A)

-continued

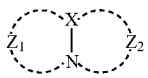
(B)

In the formula (B), X represents a carbon atom or a nitrogen atom. $Z_1$ and $Z_2$ each independently represent an atom group capable of forming a nitrogen-containing heterocycle.

(C)

Preferably, the nitrogen-containing heterocyclic derivative is an organic compound having a nitrogen-containing aromatic polycyclic group having a five-membered ring or six-membered ring. When the nitrogen-containing heterocyclic derivative is such a nitrogen-containing aromatic polycyclic group that contains plural nitrogen atoms, the nitrogen-containing heterocyclic derivative may be a nitrogen-containing aromatic polycyclic organic compound having a skeleton formed by a combination of the skeletons respectively represented by the formulae (A) and (B), or by a combination of the skeletons respectively represented by the formulae (A) and (C).

A nitrogen-containing group of the nitrogen-containing organic compound is selected from nitrogen-containing heterocyclic groups respectively represented by the following.

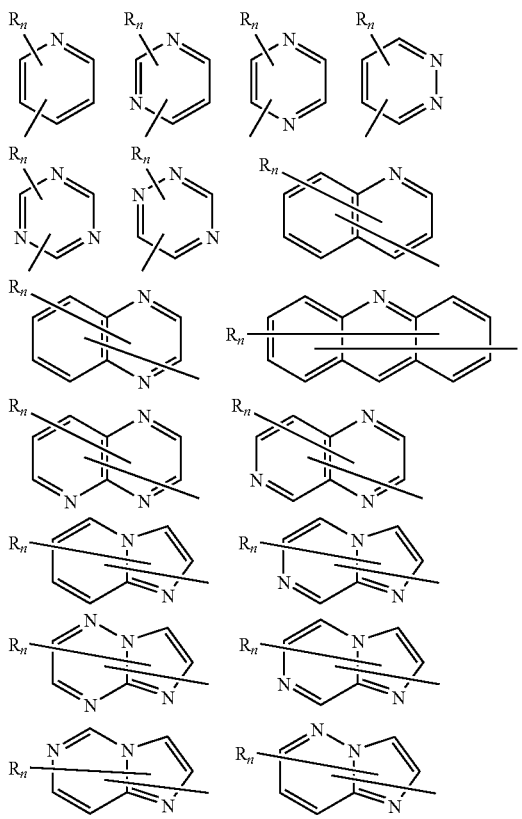

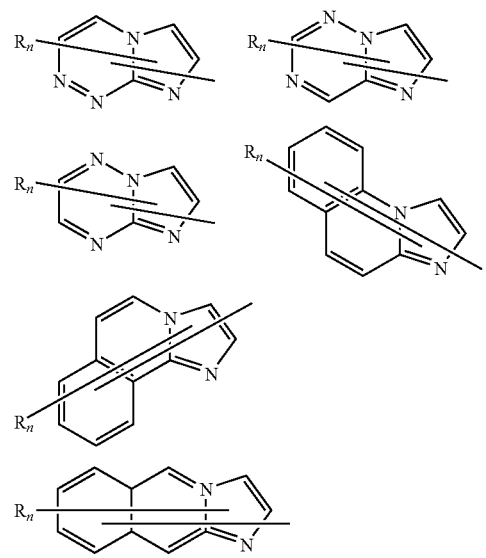

In the formulae: R represents an aryl group having 6 to 40 carbon atoms, heteroaryl group having 3 to 40 carbon atoms, alkyl group having 1 to 20 carbon atoms or alkoxy group having 1 to 20 carbon atoms; and n represents an integer in a range of 0 to 5. When n is an integer of 2 or more, plural R may be mutually the same or different.

A preferable specific compound is a nitrogen-containing heterocyclic derivative represented by the following formula HAr-L$^1$-Ar$^1$—Ar$^2$ In the formula, HAr represents a substituted or unsubstituted nitrogen-containing heterocycle having 3 to 40 carbon atoms; L$^1$ represents a single bond, substituted or unsubstituted arylene group having 6 to 40 carbon atoms or substituted or unsubstituted heteroarylene group having 3 to 40 carbon atoms; Ar$^1$ represents a substituted or unsubstituted divalent aromatic hydrocarbon group having 6 to 40 carbon atoms; and Ar$^2$ represents a substituted or unsubstituted aryl group having 6 to 40 carbon atoms or substituted or unsubstituted heteroaryl group having 3 to 40 carbon atoms.

HAr is exemplarily selected from the following group.

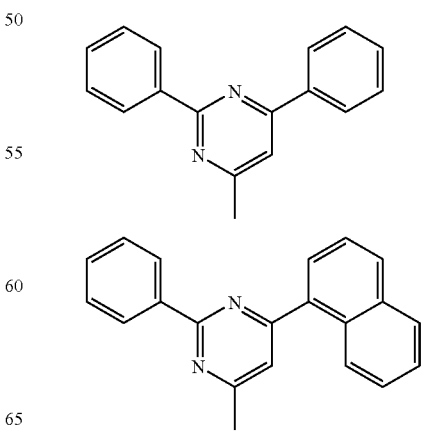

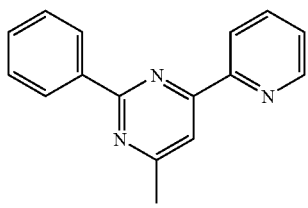
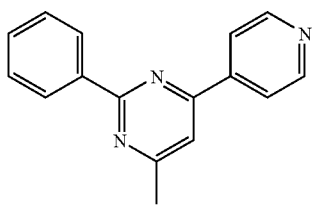
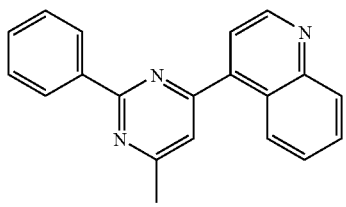
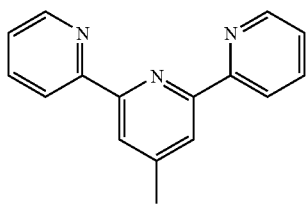
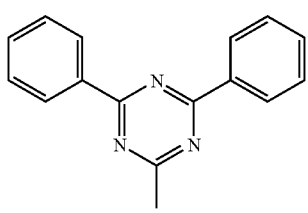
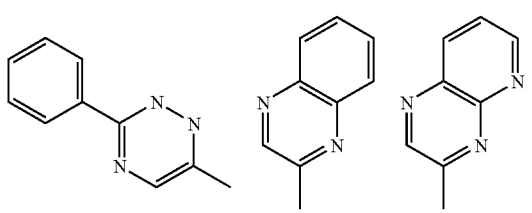
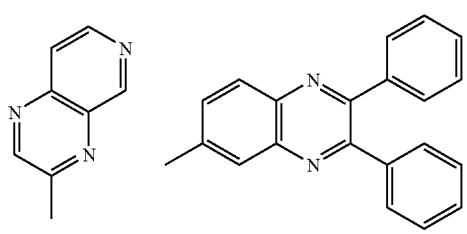
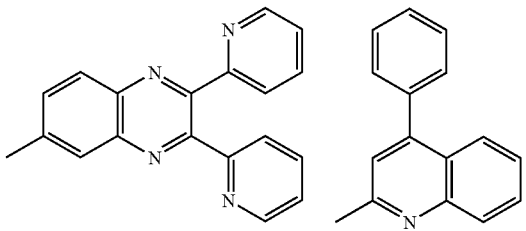
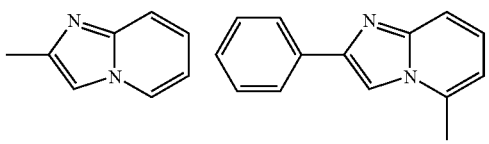
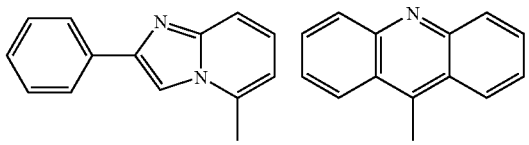
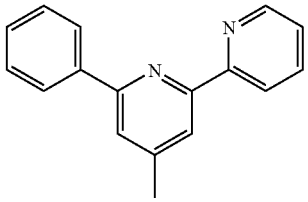
$L^1$ is exemplarily selected from the following group.
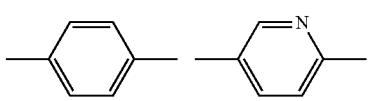
$Ar^2$ is exemplarily selected from the following group.
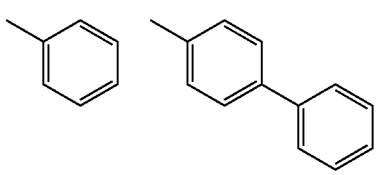
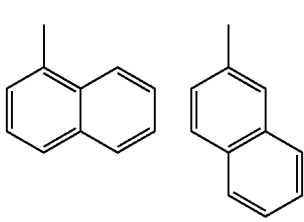

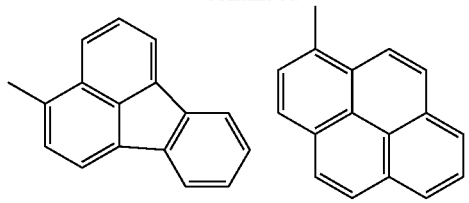
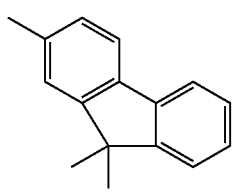

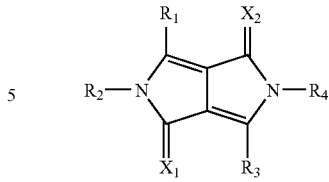

In the formula, $R_1$ to $R_4$ each independently represent a hydrogen atom, substituted or unsubstituted aliphatic group, substituted or unsubstituted alicyclic group, substituted or unsubstituted carbocyclic aromatic cyclic group or substituted or unsubstituted heterocyclic group. $X_1$ and $X_2$ each independently represent an oxygen atom, sulfur atom or dicyanomethylene group.

Alternatively, the following compound (see JP-A-2000-173774) can also be favorably used.

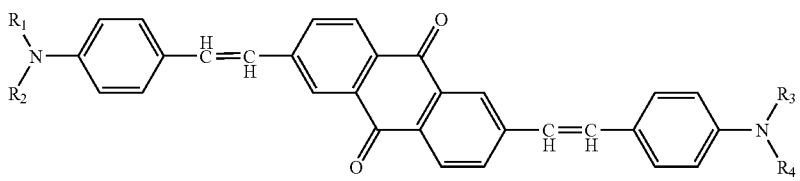

$Ar^1$ is exemplarily selected from the following arylanthranil groups.

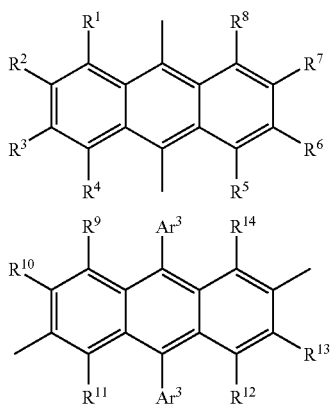

In the formula, $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 carbon atoms, substituted or unsubstituted aryl group having 6 to 40 carbon atoms or heteroaryl group having 3 to 40 carbon atoms. $Ar^3$ represents a substituted or unsubstituted aryl group having 6 to 40 carbon atoms or heteroaryl group having 3 to 40 carbon atoms.

The nitrogen-containing heterocyclic derivative may be a nitrogen-containing heterocyclic derivative in which $R^1$ to $R^8$ in the structure of $Ar^1$ represented by the above formula each represent a hydrogen atom.

Other than the above, the following compound (see JP-A-9-3448) can be favorably used.

In the formula, $R^1$, $R^2$, $R^3$ and $R^4$, which may be mutually the same or different, each represent an aryl group represented by the following formula.

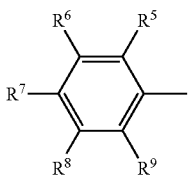

In the formula, $R^5$, $R^6$, $R^7$, $R^8$ and $R^9$, which may be mutually the same or different, each represent a hydrogen atom, saturated or unsaturated alkoxy group, alkyl group, amino group or alkylamino group. At least one of $R^5$, $R^6$, $R^7$, $R^8$ and $R^9$ represents a saturated or unsaturated alkoxy group, alkyl group, amino group or alkylamino group.

A polymer compound containing the nitrogen-containing heterocyclic group or a nitrogen-containing heterocyclic derivative may be used.

The electron transporting layer preferably contains at least one of nitrogen-containing heterocycle derivatives respectively represented by the following formulae (201) to (203).

(201)

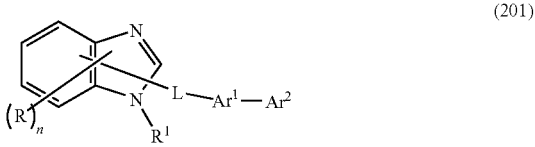

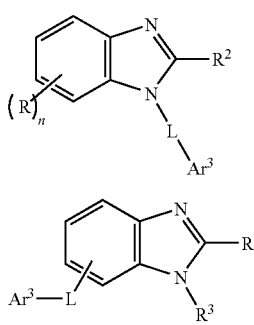

(202)

(203)

In the formulae (201) to (203): R represents a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or substituted or unsubstituted alkoxy group having 1 to 20 carbon atoms; n represents an integer of 0 to 4; $R^1$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or alkoxy group having 1 to 20 carbon atoms; $R^2$ and $R^3$ each independently represent a hydrogen atom, substituted or unsubstituted aryl group having 6 to 60 carbon atoms, substituted or unsubstituted pyrydyl group, substituted or unsubstituted quinolyl group, substituted or unsubstituted alkyl group having 1 to 20 carbon atoms or substituted or unsubstituted alkoxy group having 1 to 20 carbon atoms; L represents a substituted or unsubstituted arylene group having 6 to 60 carbon atoms, substituted or unsubstituted pyridinylene group, substituted or unsubstituted quinolinylene group or substituted or unsubstituted fluorenylene group; $Ar^1$ represents a substituted or unsubstituted arylene group having 6 to 60 carbon atoms, substituted or unsubstituted pyridinylene group or substituted or unsubstituted quinolinylene group; $Ar^2$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or substituted or unsubstituted alkoxy group having 1 to 20 carbon atoms.

$Ar^3$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, substituted or unsubstituted alkoxy group having 1 to 20 carbon atoms or a group represented by —$Ar^1$—$Ar^2$ ($Ar^1$ and $Ar^2$ may be the same as the above).

In the formulae (201) to (203), R represents a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms or substituted or unsubstituted alkoxy group having 1 to 20 carbon atoms.

The aryl group having 6 to 60 carbon atom is preferably an aryl group having 6 to 40 carbon atoms, more preferably an aryl group having 6 to 20 carbon atoms. Examples of such an aryl group are a phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, a monovalent group formed of spirobifluorene, perfluorophenyl group, perfluoronaphthyl group, perfluoroanthryl group, perfluorobiphenyl group, a monovalent group formed of 9-phenylanthracene, a monovalent group formed of 9-(1'naphthyl)anthracene, a monovalent group formed of 9-(2'-naphthyl)anthracene, a monovalent group formed of 6-phenylchrysene, and a monovalent group formed of 9-[4-(diphenylamine)phenyl]anthracene, among which a phenyl group, naphthyl group, biphenyl group, terphenyl group, 9-(10-phenyl)anthryl group, 9-[10-(1'-naphthyl)]anthryl group and 9-[10-(2'-naphthyl)]anthryl group are preferable.

The alkyl group having 1 to 20 carbon atoms is preferably an alkyl group having 1 to 6 carbon atoms. Examples of such an alkyl group are a methyl group, ethyl group, propyl group, butyl group, pentyl group, hexyl group, and a haloalkyl group such as trifluoromethyl group. When such an alkyl group has 3 or more carbon atoms, the alkyl group may be linear, cyclic or branched.

The alkoxy group having 1 to 20 carbon atoms is preferably an alkoxy group having 1 to 6 carbon atoms. Examples of such an alkoxy group are a methoxy group, ethoxy group, propoxy group, butoxy group, pentyloxy group, and hexyloxy group. When such an alkoxy group has 3 or more carbon atoms, the alkoxy group may be linear, cyclic or branched.

Examples of a substituent for the group represented by R are a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms.

Examples of the halogen atom are fluorine, chlorine, bromine, iodine and the like.

Examples for each of the alkyl group having 1 to 20 carbon atoms, the alkoxy group having 1 to 20 carbon atoms, and an aryl group having 6 to 40 carbon atoms may be the same as the above examples.

Examples of the aryloxy group having 6 to 40 carbon atoms are a phenoxy group and a biphenyloxy group.

Examples of the heteroaryl group having 3 to 40 carbon atoms are a pyroryl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group and triazolyl group.

n is an integer of 0 to 4, preferably 0 to 2.

In the formulae (201), $R^1$ represents a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or an alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $R^2$ and $R^3$ each independently represent a hydrogen atom, a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (201) to (203), L represents a substituted or unsubstituted arylene group having 6 to 60 carbon atoms, a substituted or unsubstituted pyridinylene group, a substituted or unsubstituted quinolinylene group, or a substituted or unsubstituted fluorenylene group.

The arylene group having 6 to 60 carbon atoms is preferably an arylene group having 6 to 40 carbon atoms, more preferably an arylene group having 6 to 20 carbon atoms. An example of such an arylene group is a divalent group formed by removing one hydrogen atom from the aryl group having been described in relation to R. Examples of a substituent for the group represented by L are the same as those described in relation to R.

Alternatively, L is preferably a group selected from a group consisting of the following.

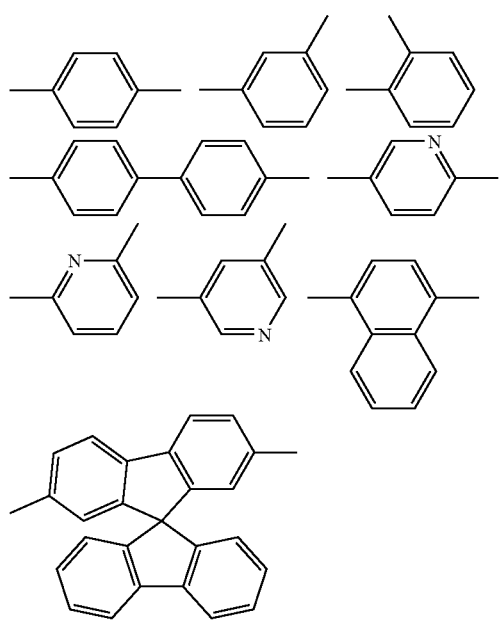

In the formulae (201), Ar¹ represents a substituted or unsubstituted arylene group having 6 to 60 carbon atoms, a substituted or unsubstituted pyridinylene group, or a substituted or unsubstituted quinolinylene group. Examples of a substituent for the group represented by L are the same as those described in relation to R.

Alternatively, Ar¹ is preferably selected from a group consisting of fused cyclic groups respectively represented by the following formulae (101) to (110).

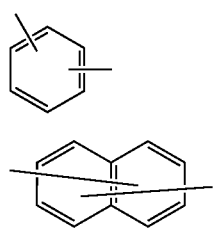
(101)

(102)

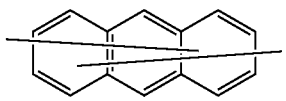
(103)

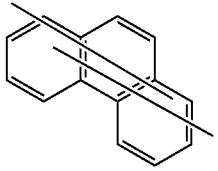
(104)

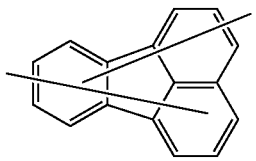
(105)

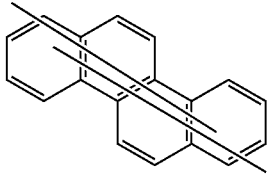
(106)

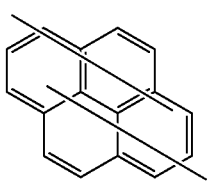
(107)

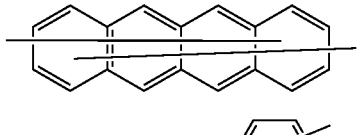
(108)

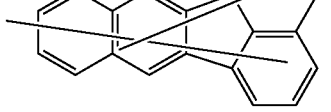
(109)

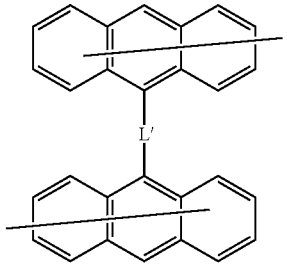
(110)

In the formulae (101) to (110), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (110), L' represents a single bond or a group selected from a group consisting of the following.

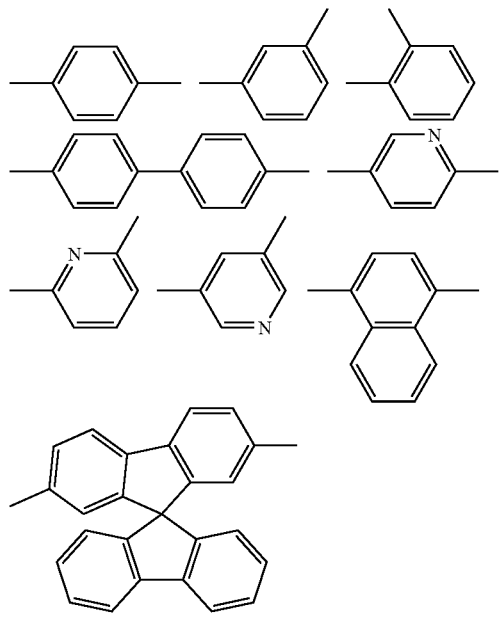

The structure of $Ar^1$ represented by the formula (103) is preferably a fused cyclic group represented by any one of the following formulae (111) to (125).

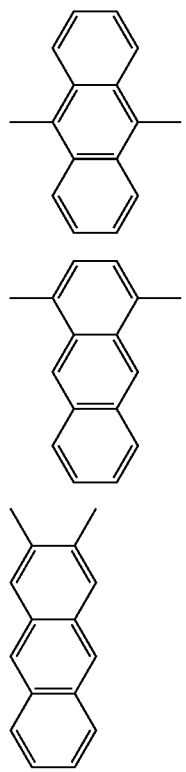

(111)

(112)

(113)

-continued

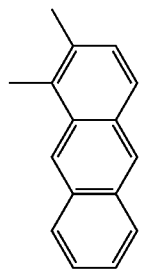

(114)

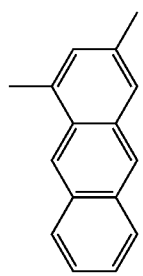

(115)

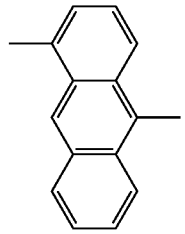

(116)

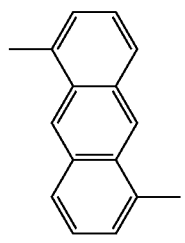

(117)

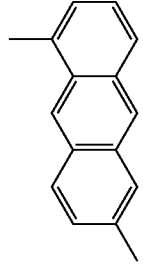

(118)

(119)

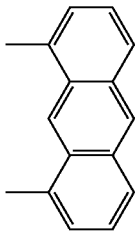 (120)

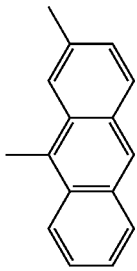 (121)

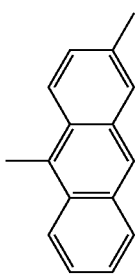 (122)

(123)

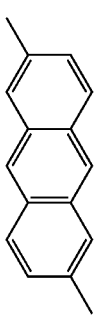 (124)

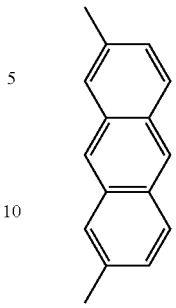 (125)

In the formulae (111) to (125), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (201), $Ar^2$ represents a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $Ar^3$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ ($Ar^1$ and $Ar^2$ may be the same as the above).

Examples for each of the groups, the preferable number of carbon atoms contained in each of the groups, and preferable examples of the substituent for each of the groups are the same as those described in relation to R.

Alternatively, $Ar^3$ is preferably selected from fused cyclic groups respectively represented by the following formulae (126) to (135).

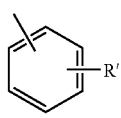 (126)

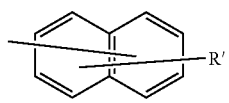 (127)

-continued

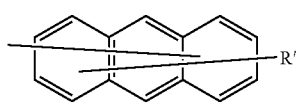
(128)

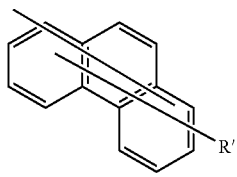
(129)

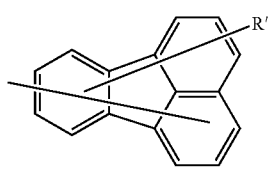
(130)

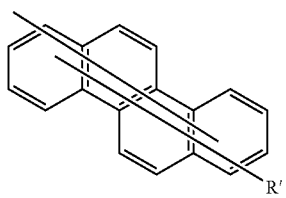
(131)

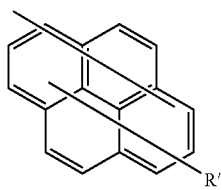
(132)

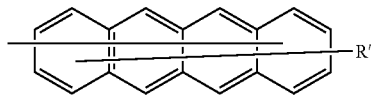
(133)

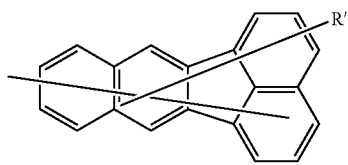
(134)

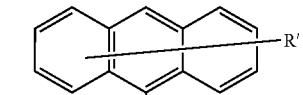
(135)

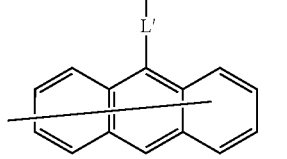

In the formulae (126) to (135), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above.

In the formula (135), L' represents the same as the above.

In the formulae (126) to (135), R' represents a hydrogen atom, a substituted or unsubstituted alkyl group having 1 to 20 carbon atoms, a substituted or unsubstituted aryl group having 6 to 40 carbon atoms, or substituted or unsubstituted heteroaryl group having 3 to 40 carbon atoms. Examples for each of the groups are the same as those described above.

A structure represented by the formula (128), which is an example of Ar³, is preferably a fused cyclic group represented by any one of the following formulae (136) to (158).

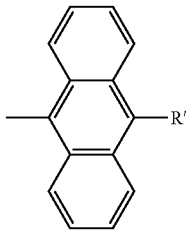
(136)

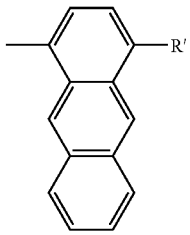
(137)

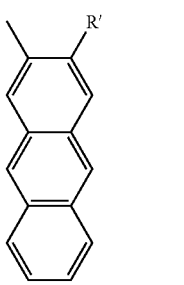
(138)

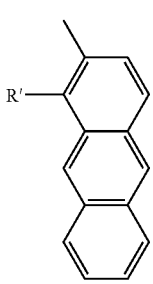
(139)

(140) 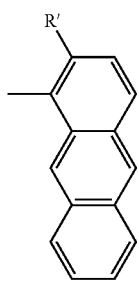
(141) 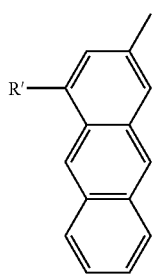
(142) 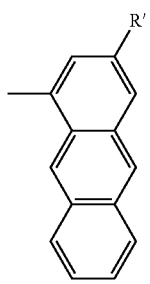
(143) 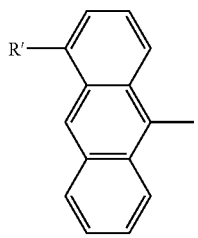
(144) 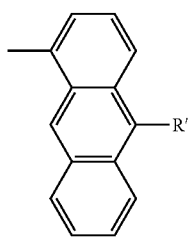
(145) 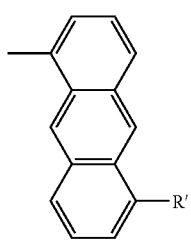
(146) 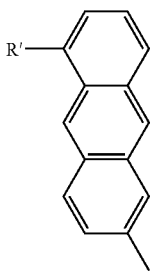
(147) 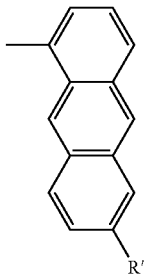
(148) 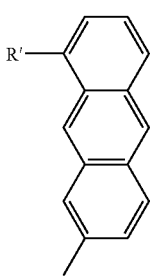
(149) 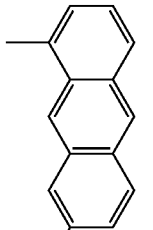
(150) 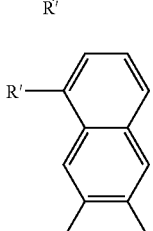
(151) 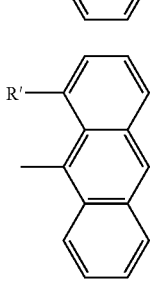

(152) 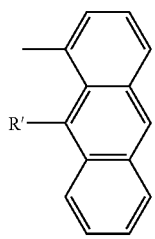

(153) 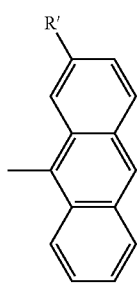

(154) 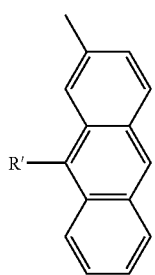

(155) 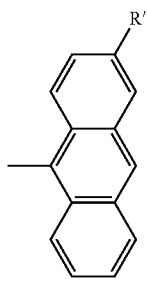

(156) 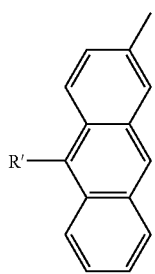

(157) 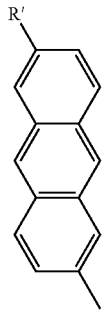

(158) 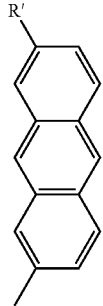

In the formulae (136) to (158), the fused rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each are linked with plural link groups, the plural link groups may be mutually the same or different. Examples for each of the groups are the same as those described above. R' is the same as the above.

Alternatively, $Ar^2$ and $Ar^3$ each independently are preferably a group selected from a group consisting of the following.

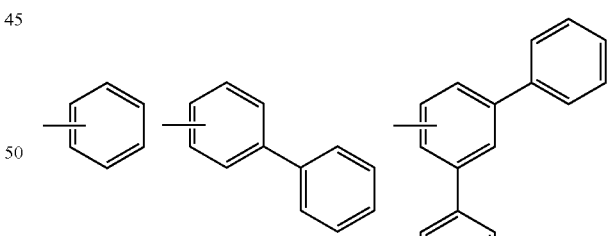

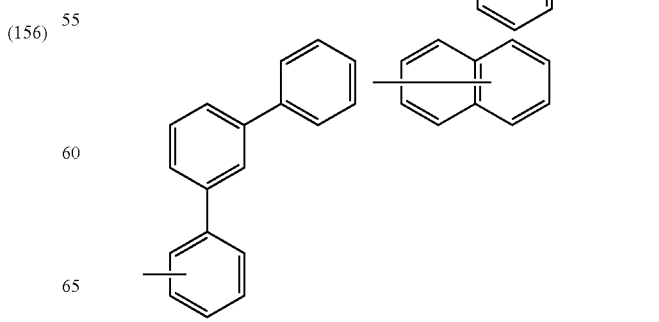

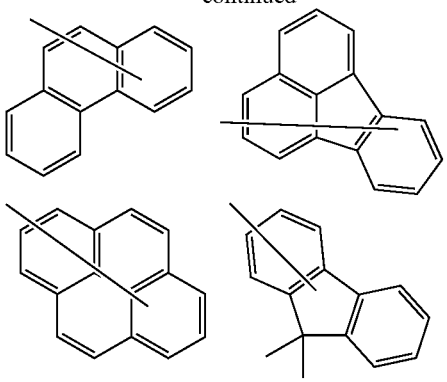
Examples of the nitrogen-containing heterocyclic derivative represented by any one of the general formulae (201) to (203) according to the aspect of the invention will be shown below. However, the invention is not limited to the exemplary compounds shown below.
In the chart shown below, HAr represents any one of structures represented by the formulae (201) to (203).
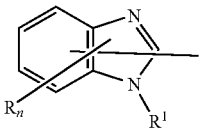 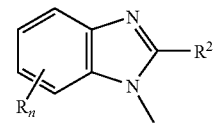
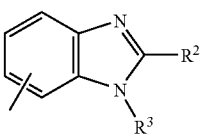

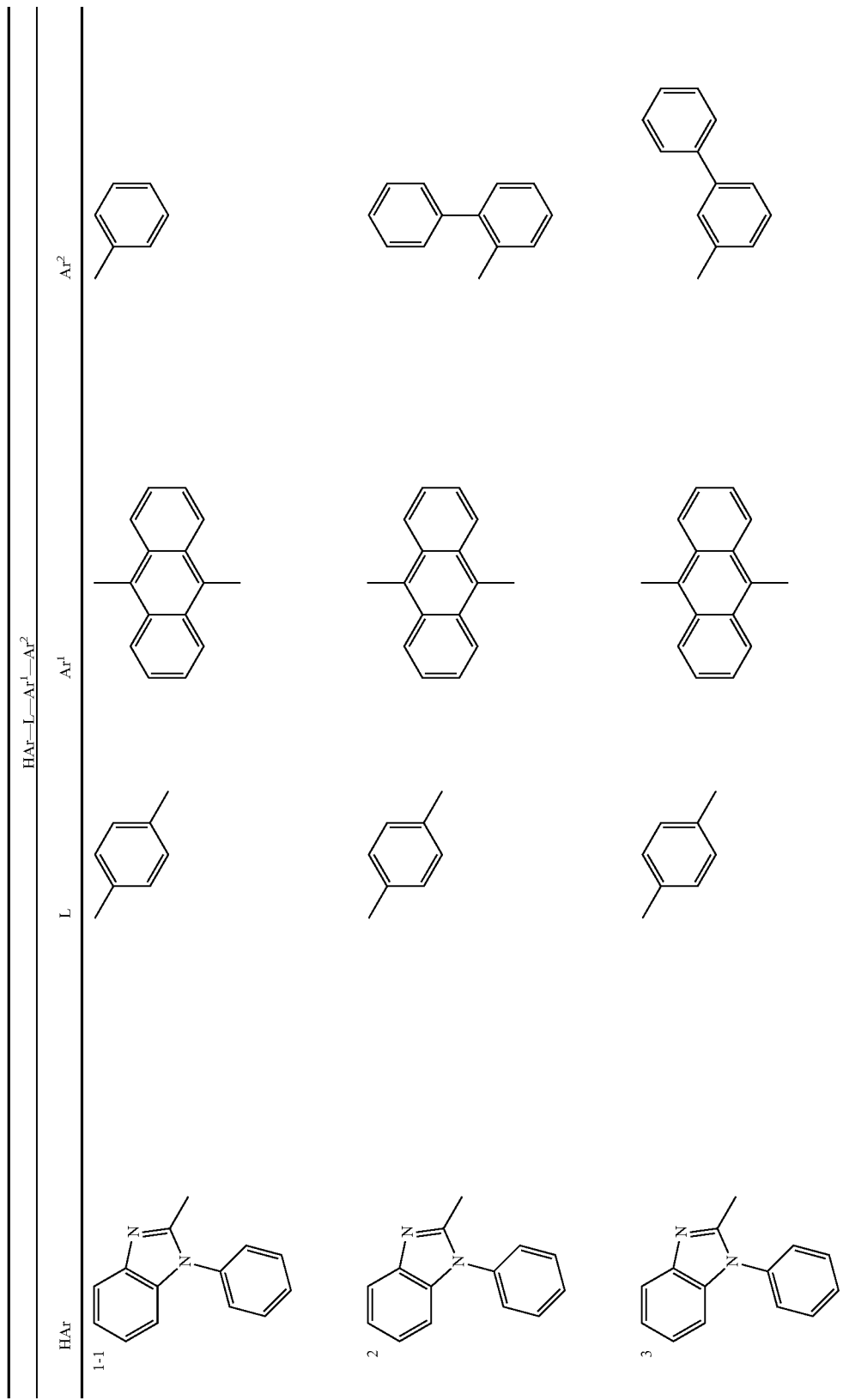

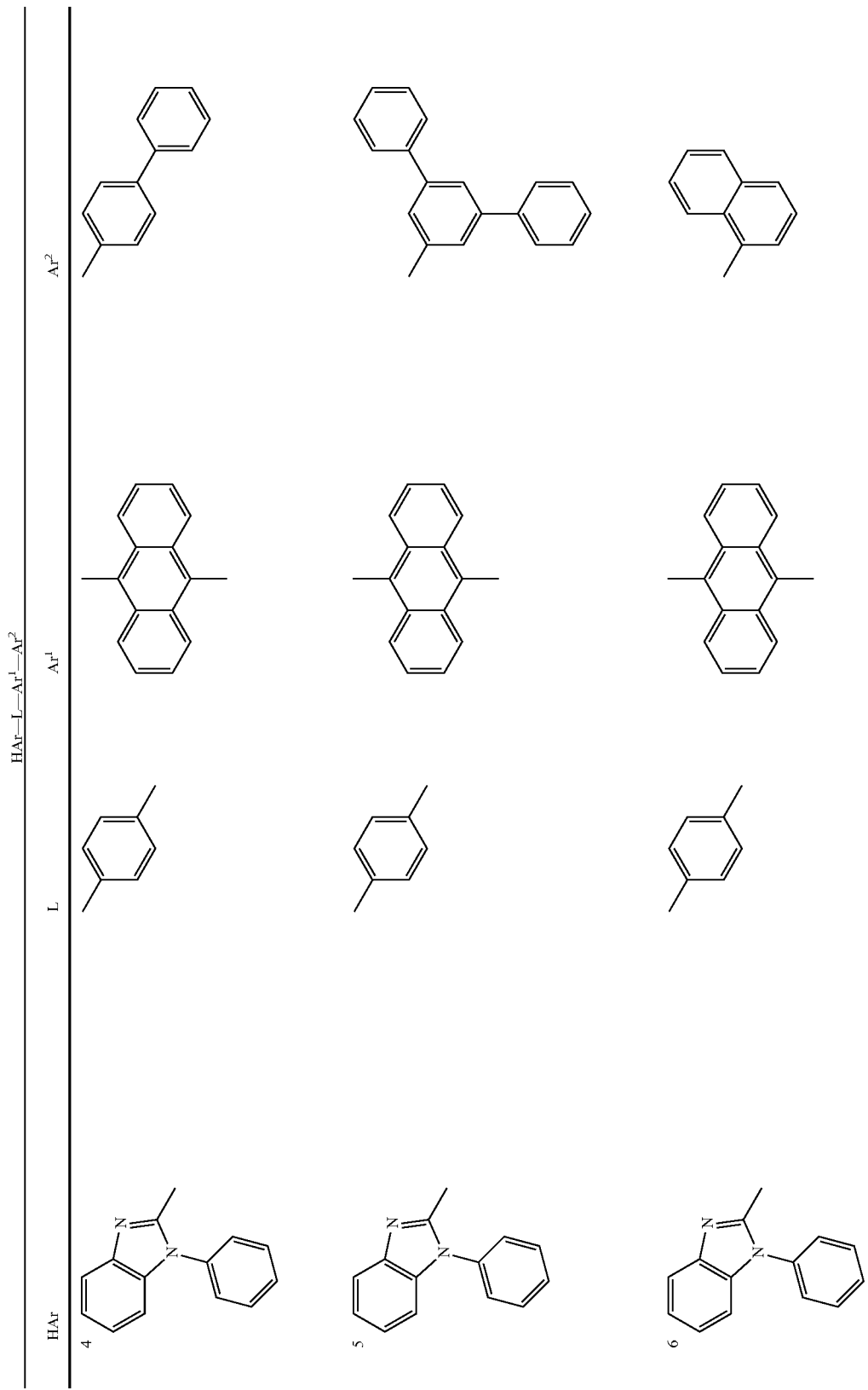

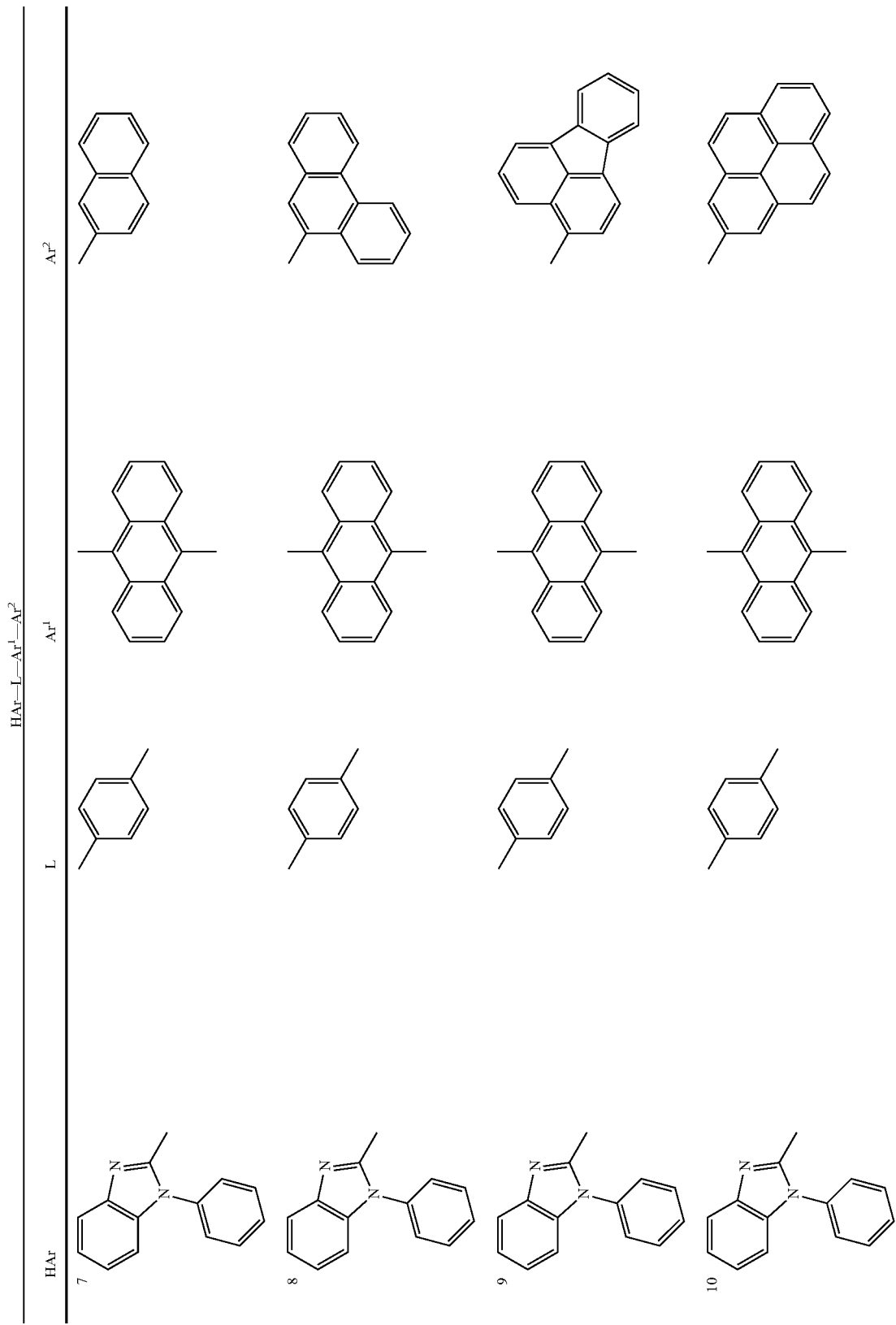

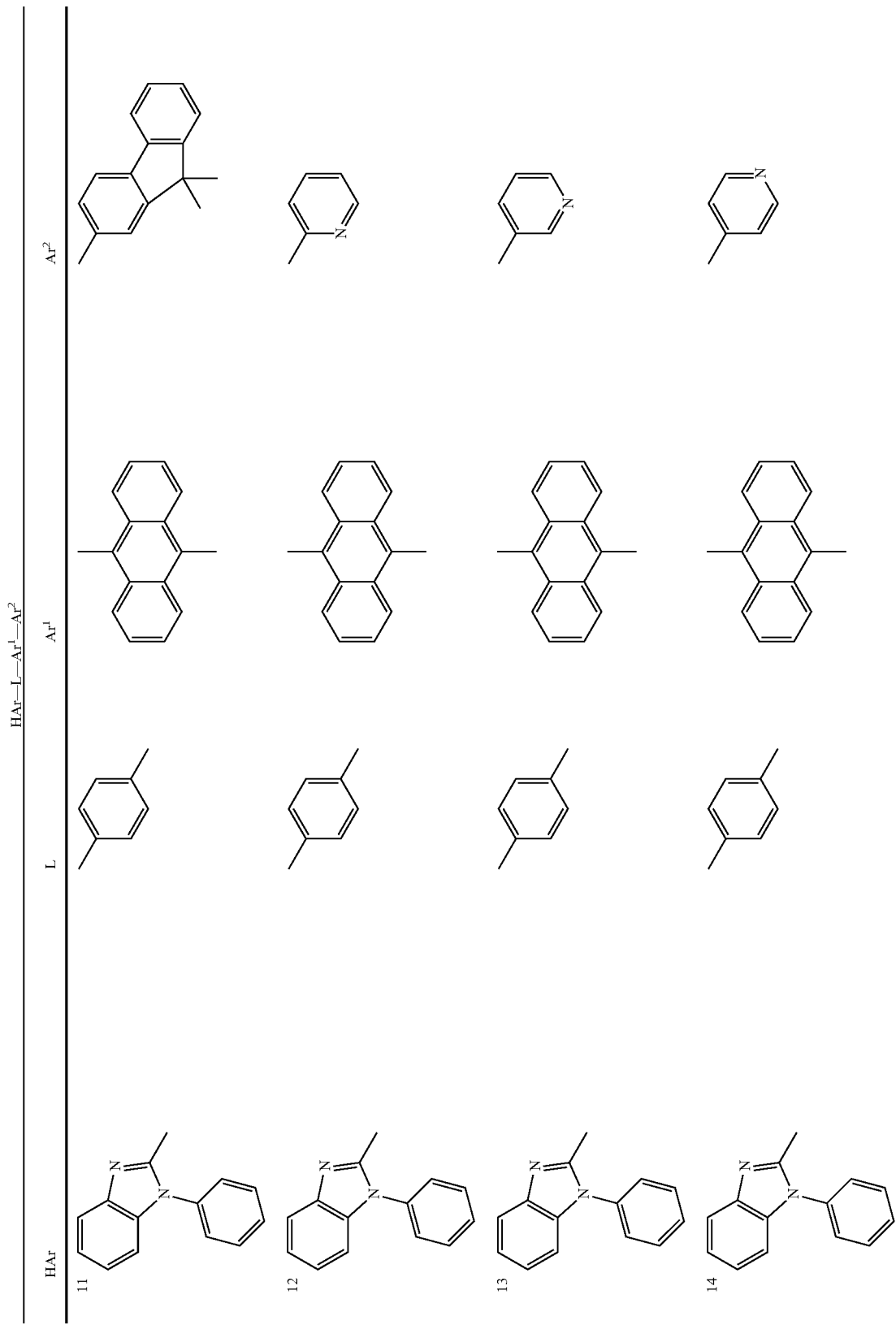

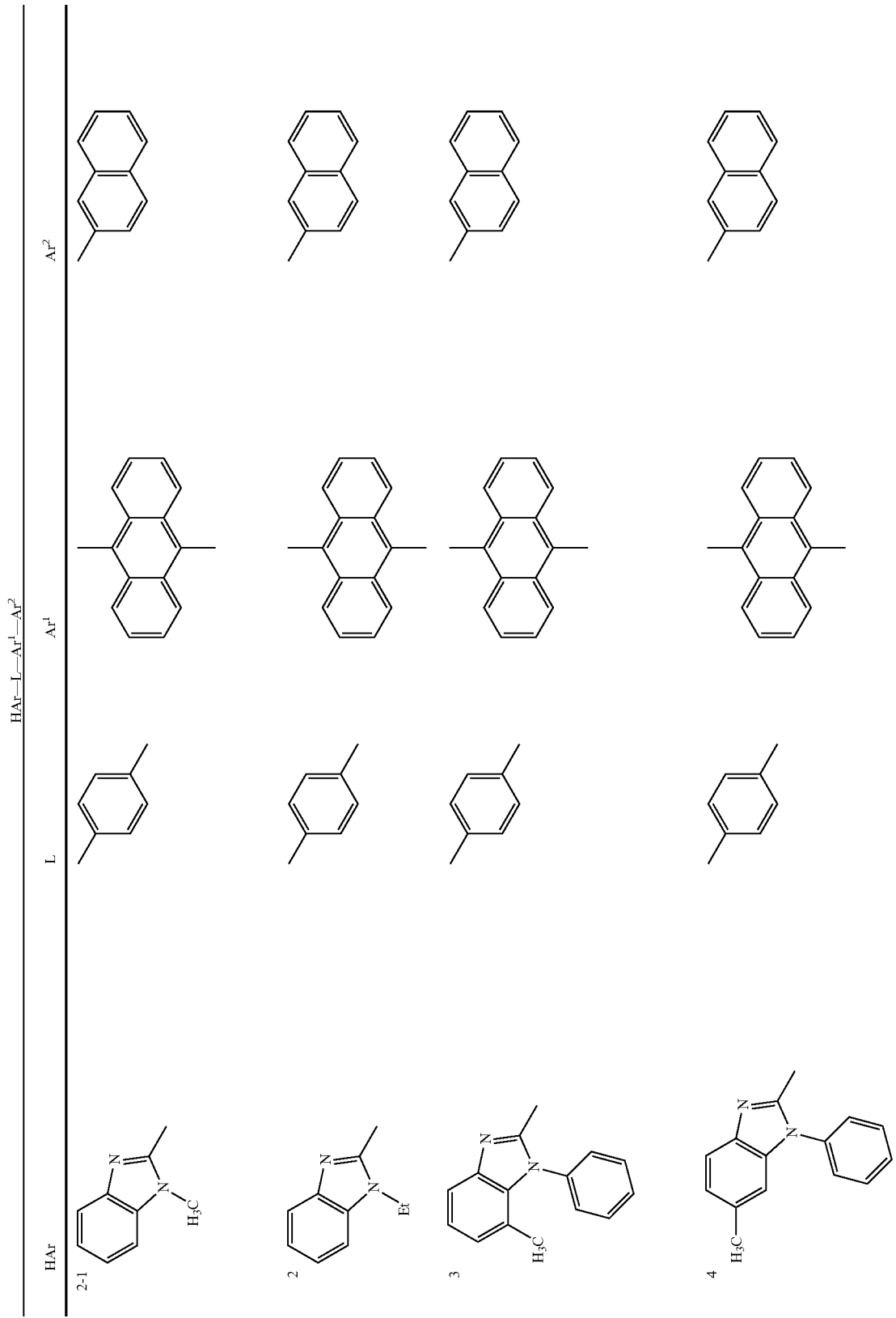

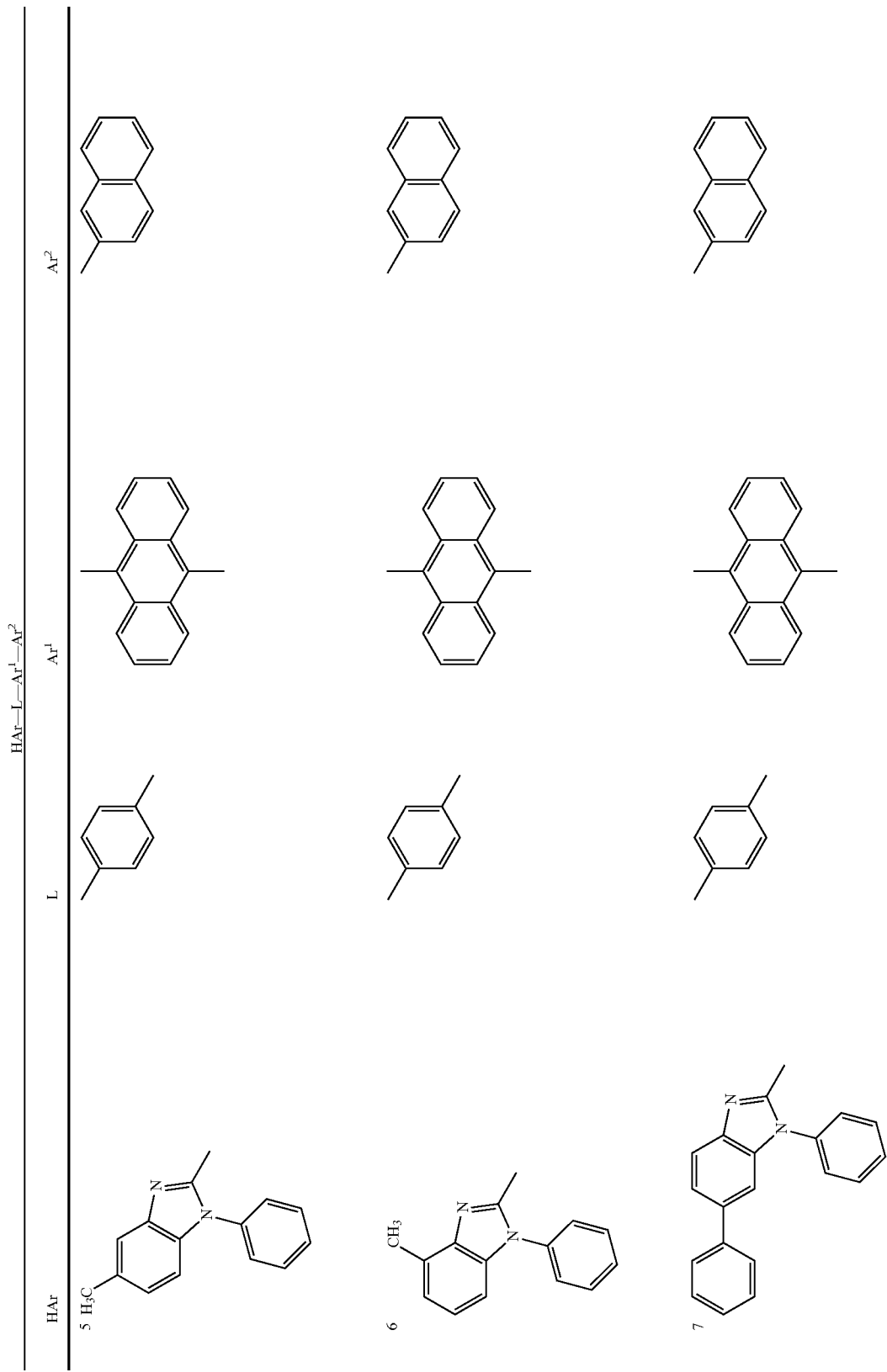

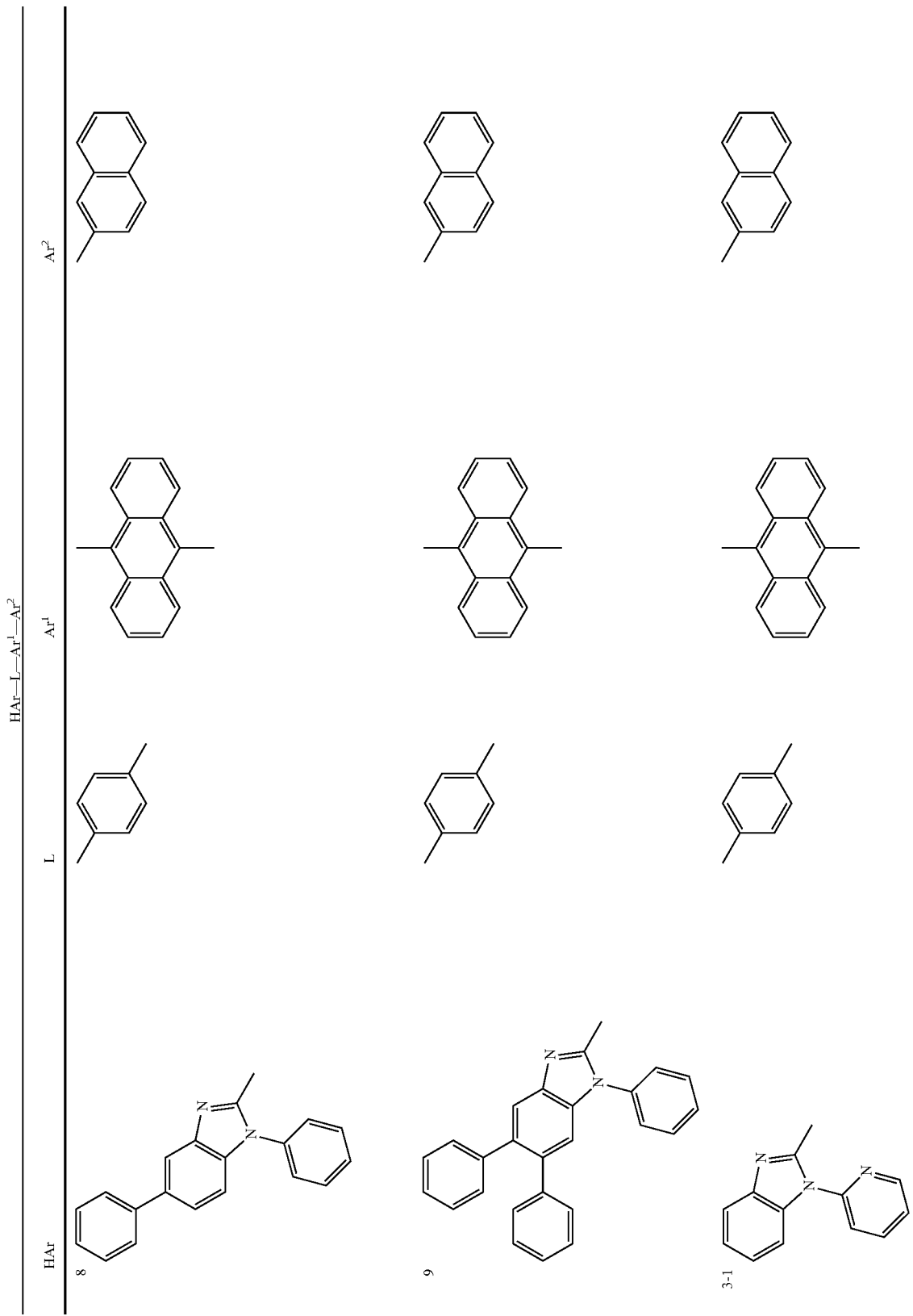

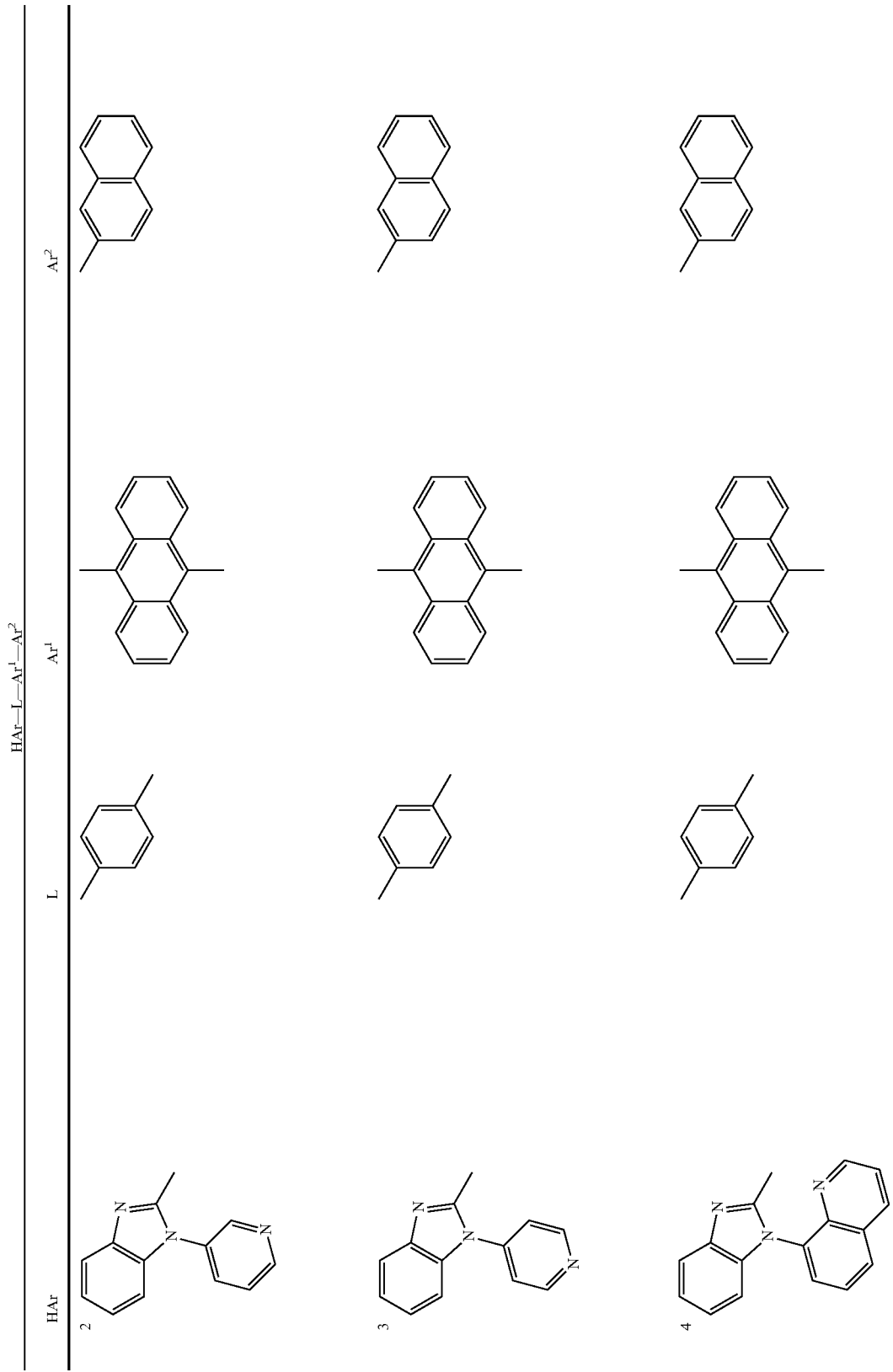

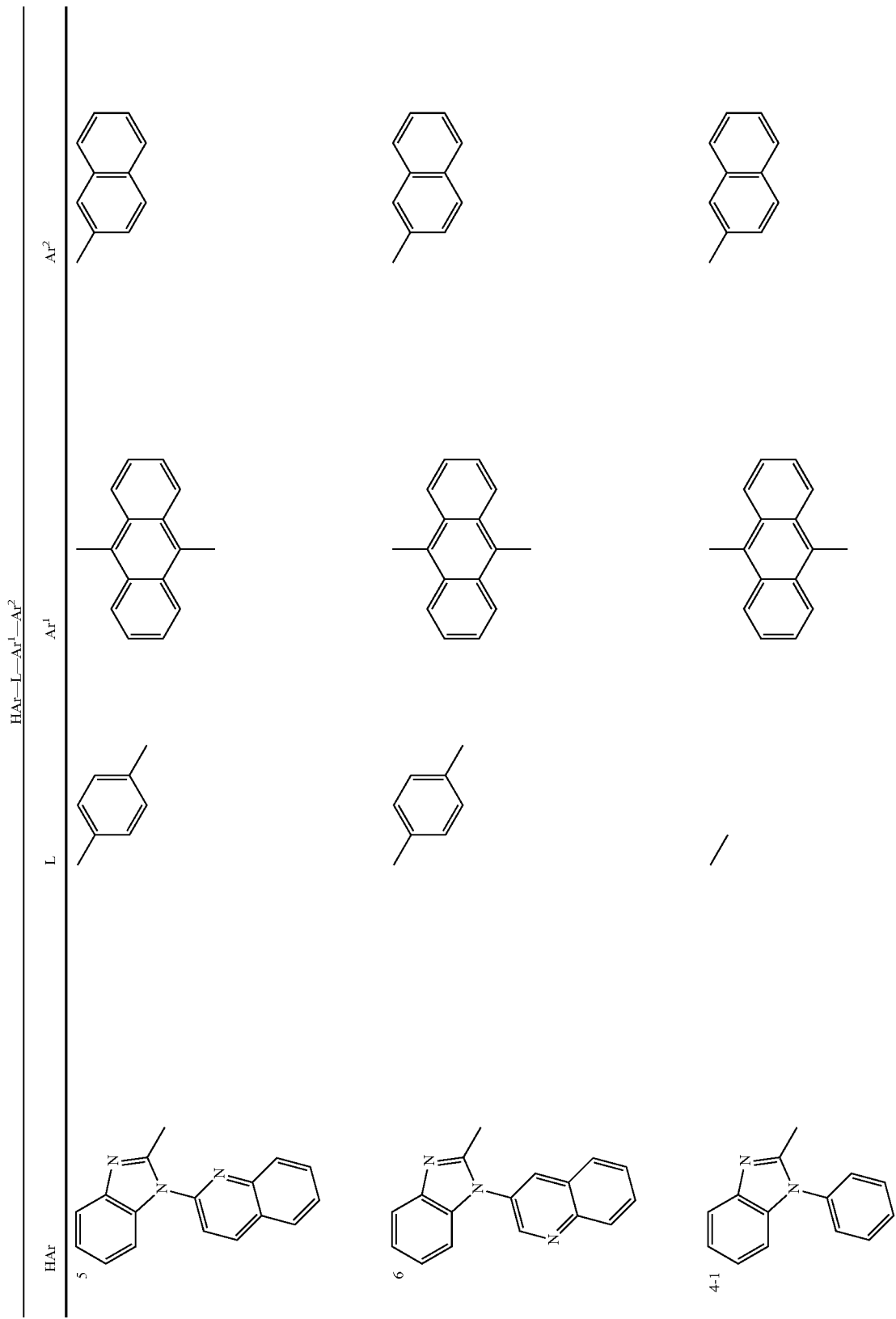

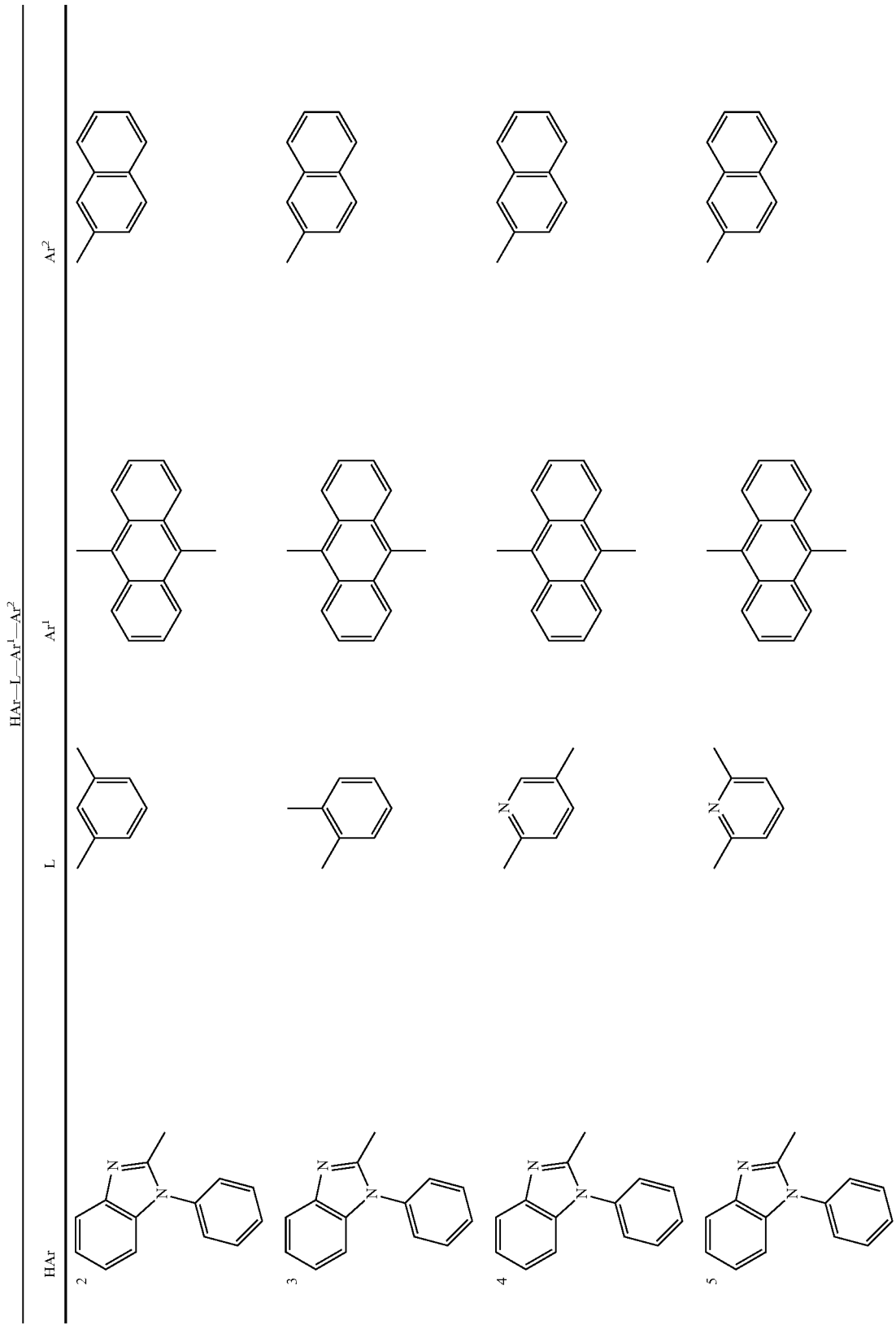

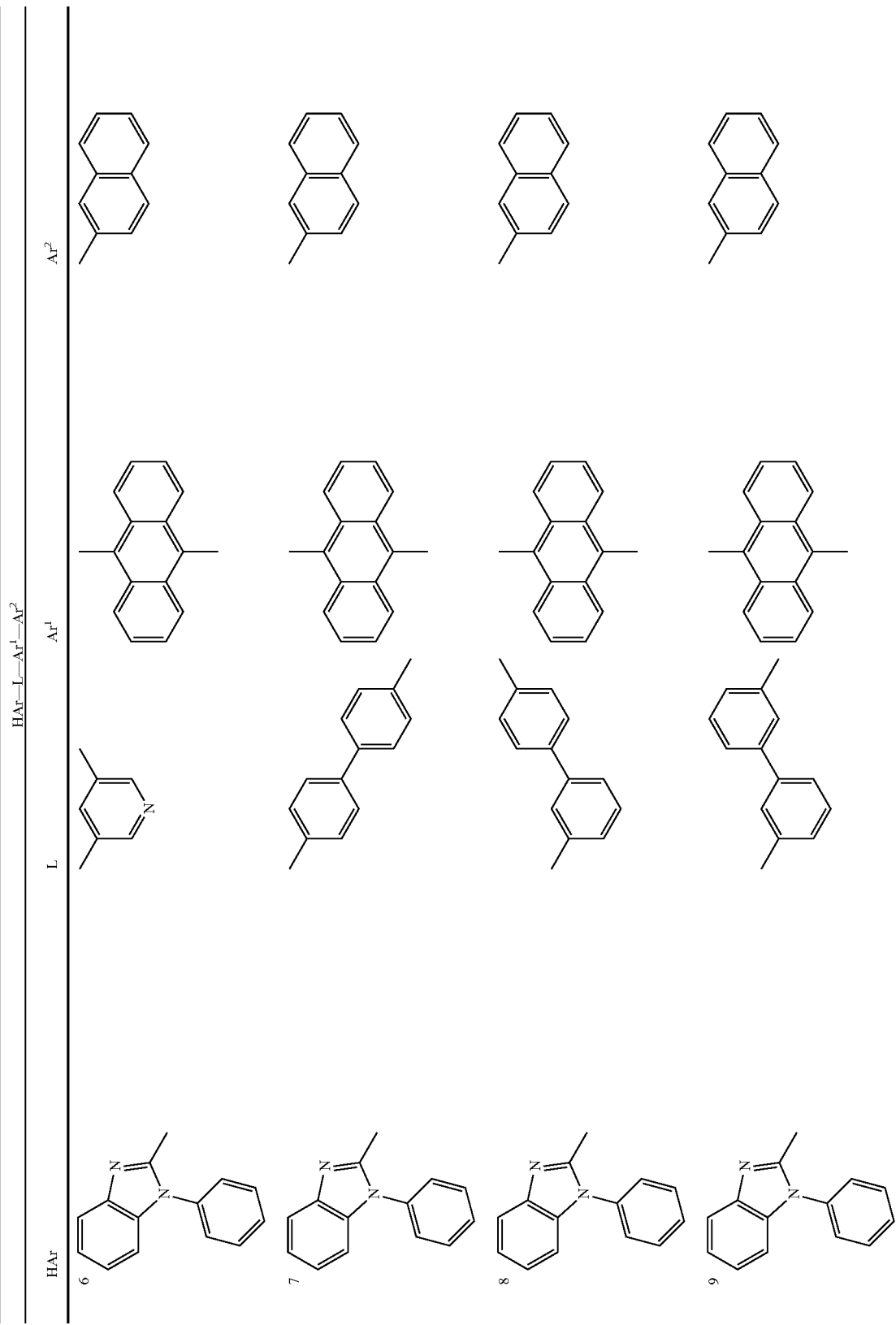

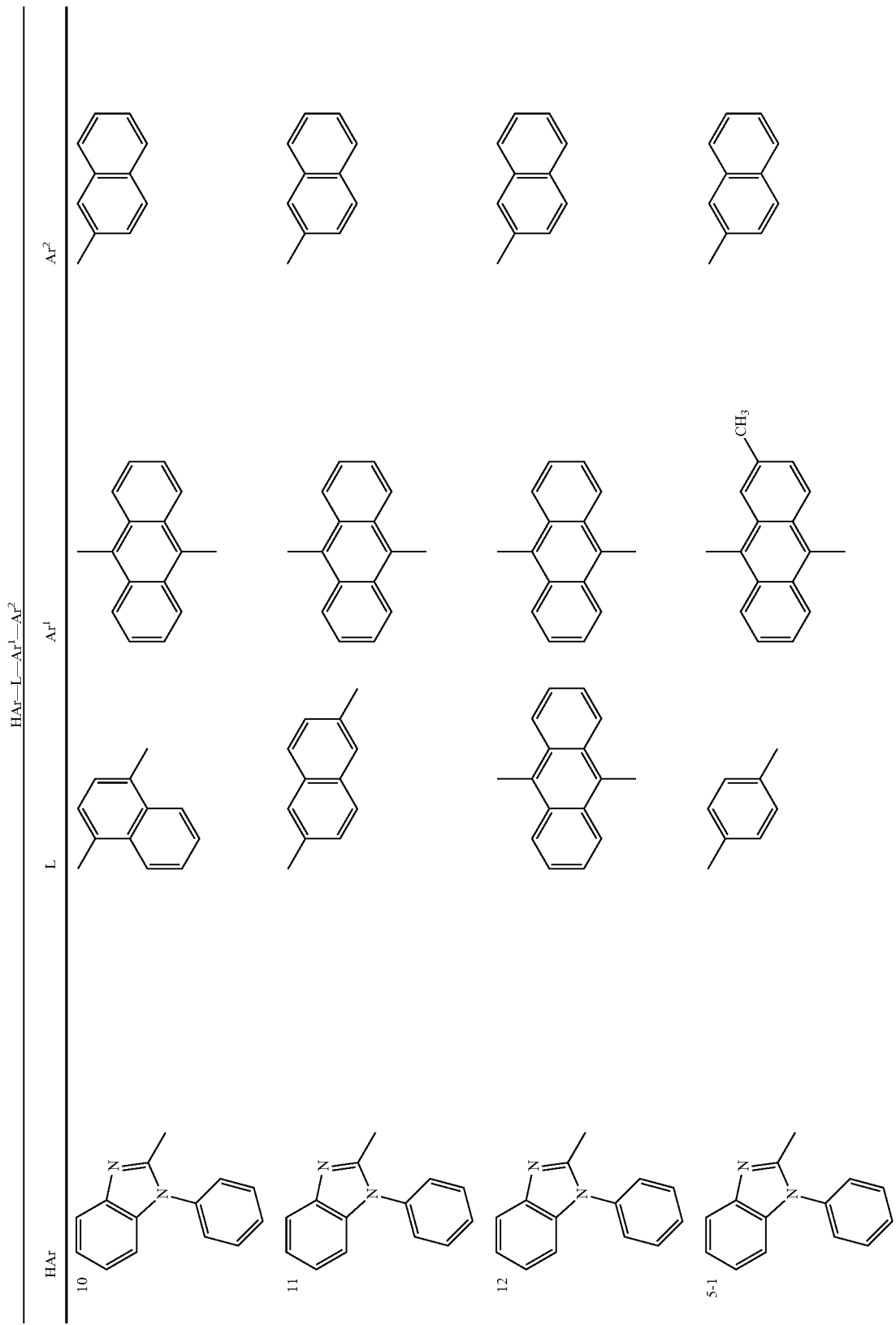

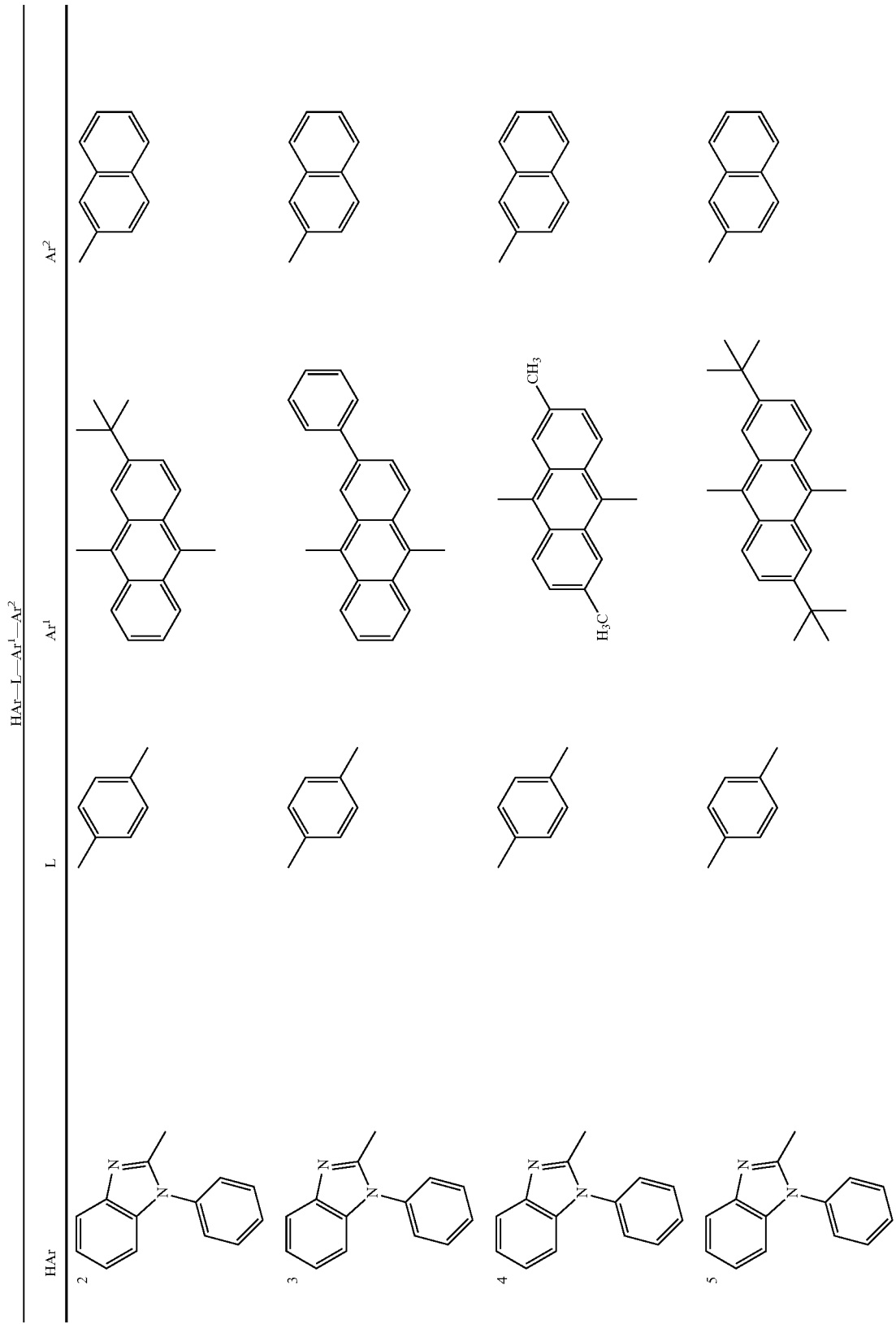

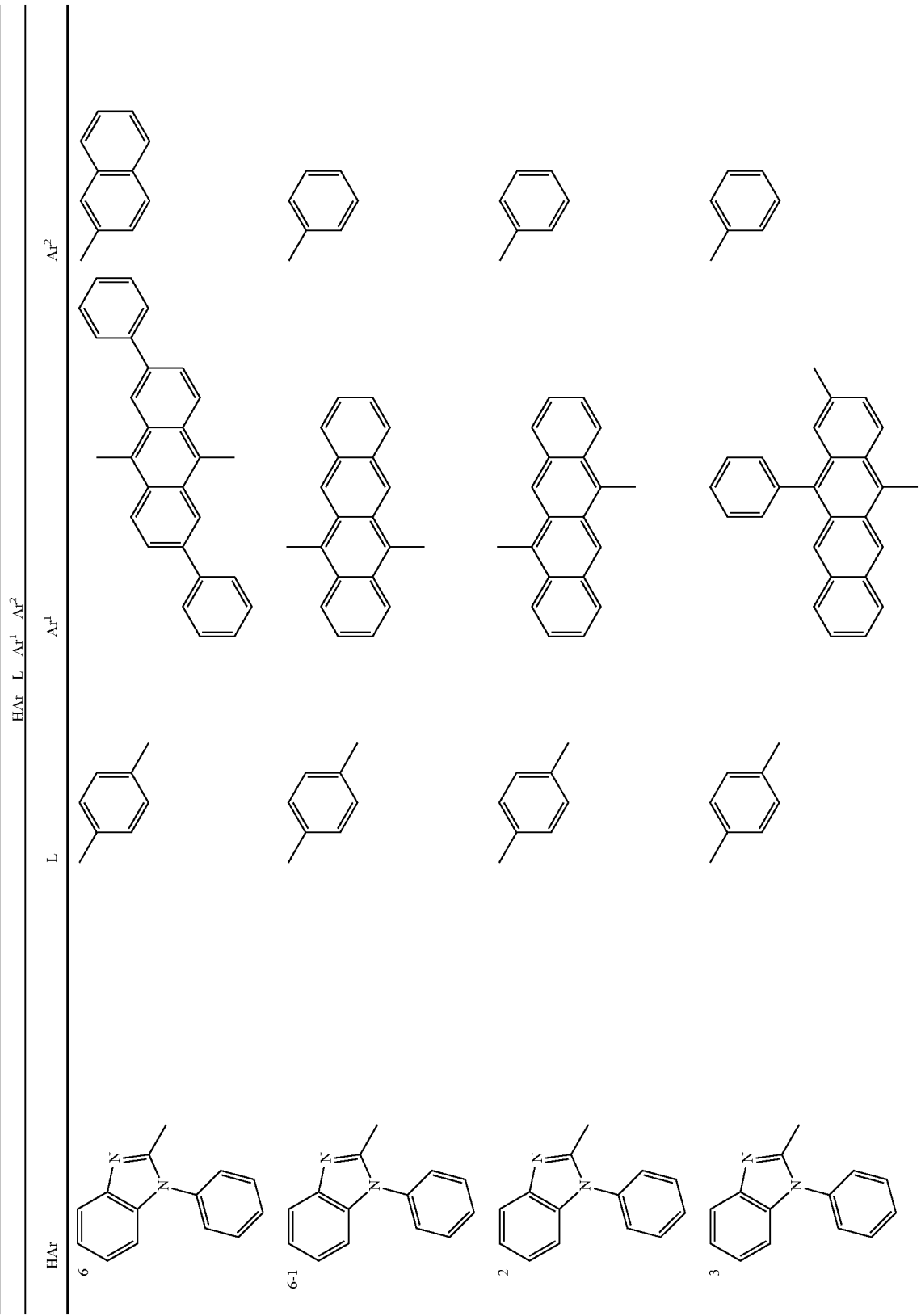

-continued
| HAr—L—Ar¹—Ar² | | | |
|---|---|---|---|
| HAr | L | Ar¹ | Ar² |
| 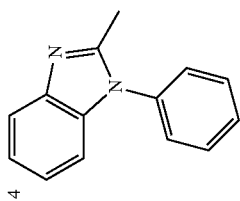 4 | 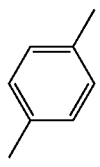 | 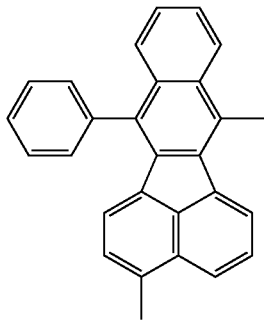 | 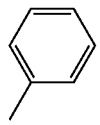 |
| 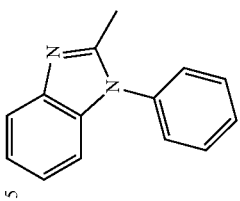 5 | 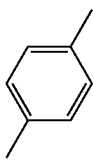 | 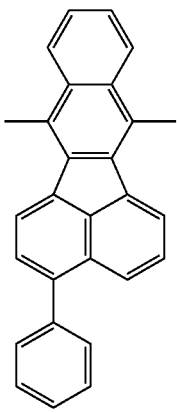 | 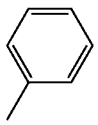 |
| 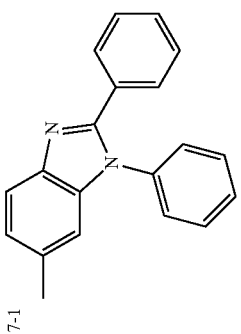 7-1 | 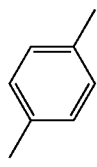 | 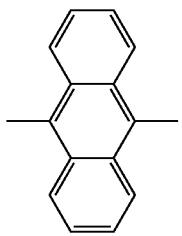 |  |

-continued
| HAr | L | Ar¹ | Ar² |
|---|---|---|---|
| HAr—L—Ar¹—Ar² | | | |
| 2 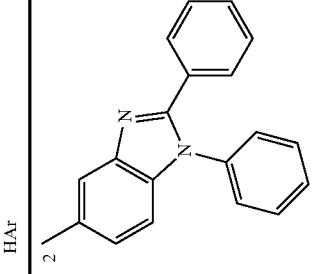 | 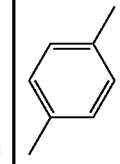 | 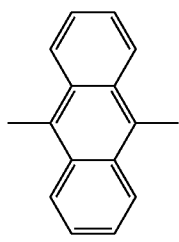 |  |
| 3 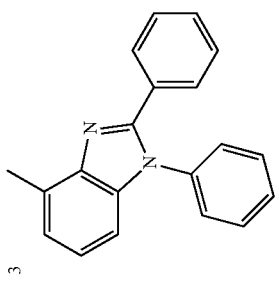 | 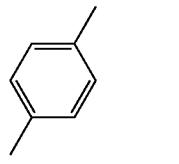 | 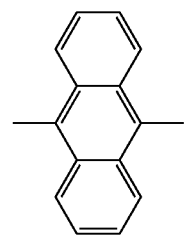 | 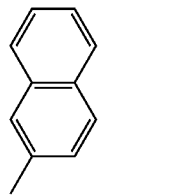 |
| 4 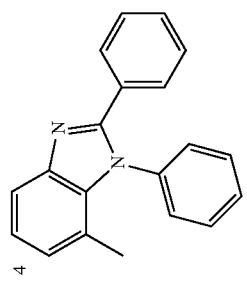 | 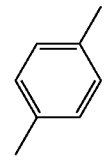 | | 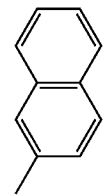 |

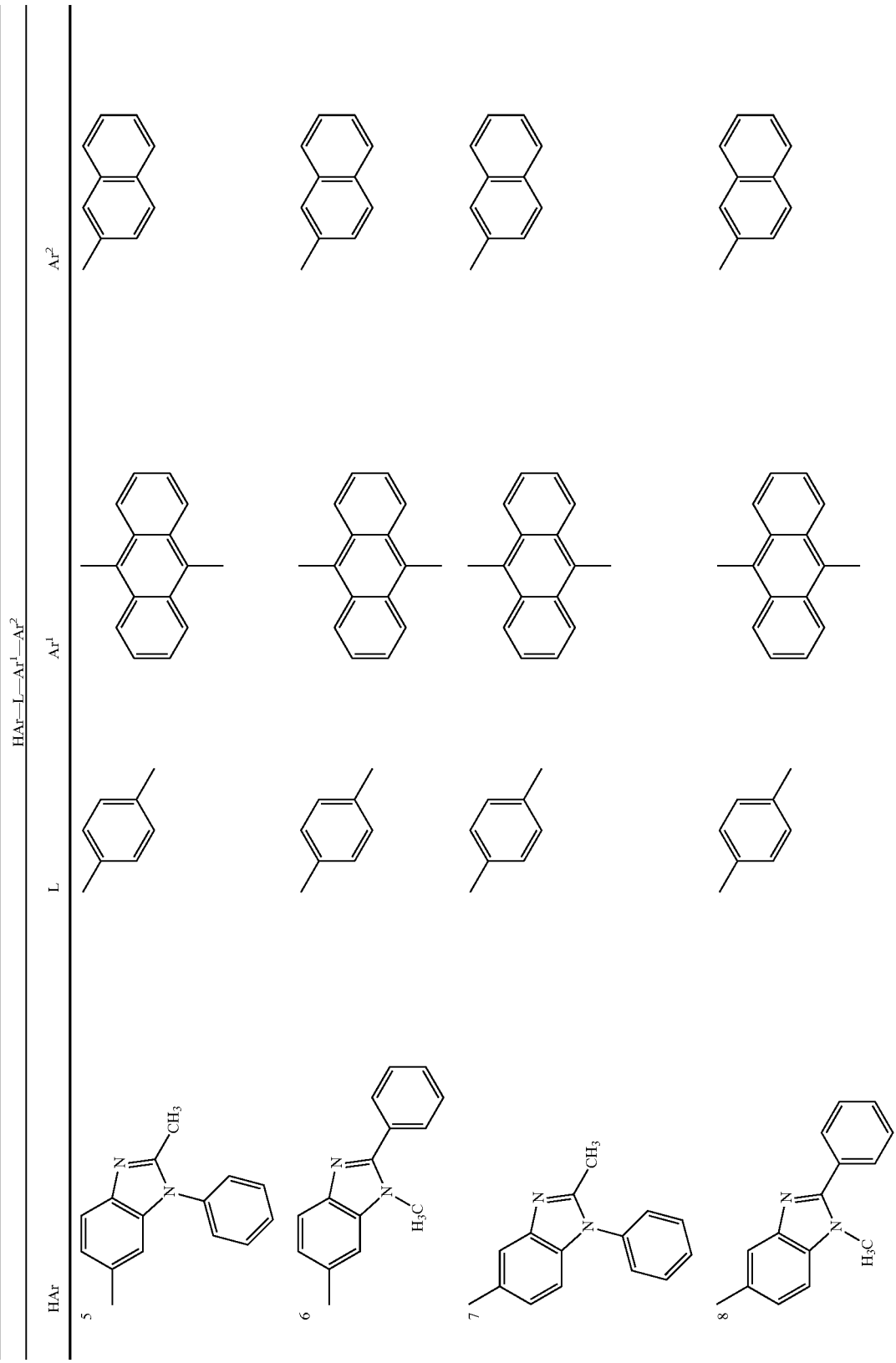

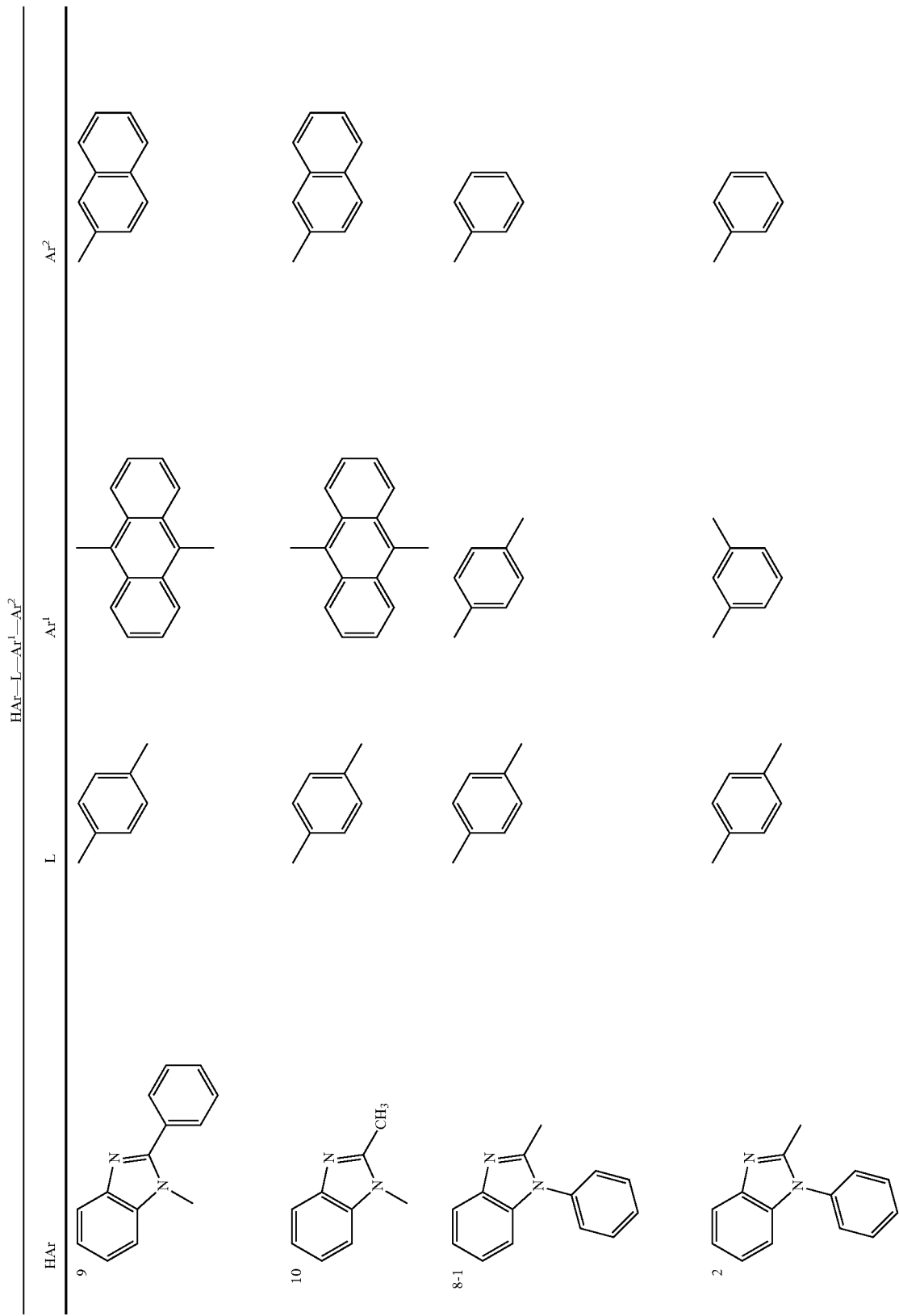

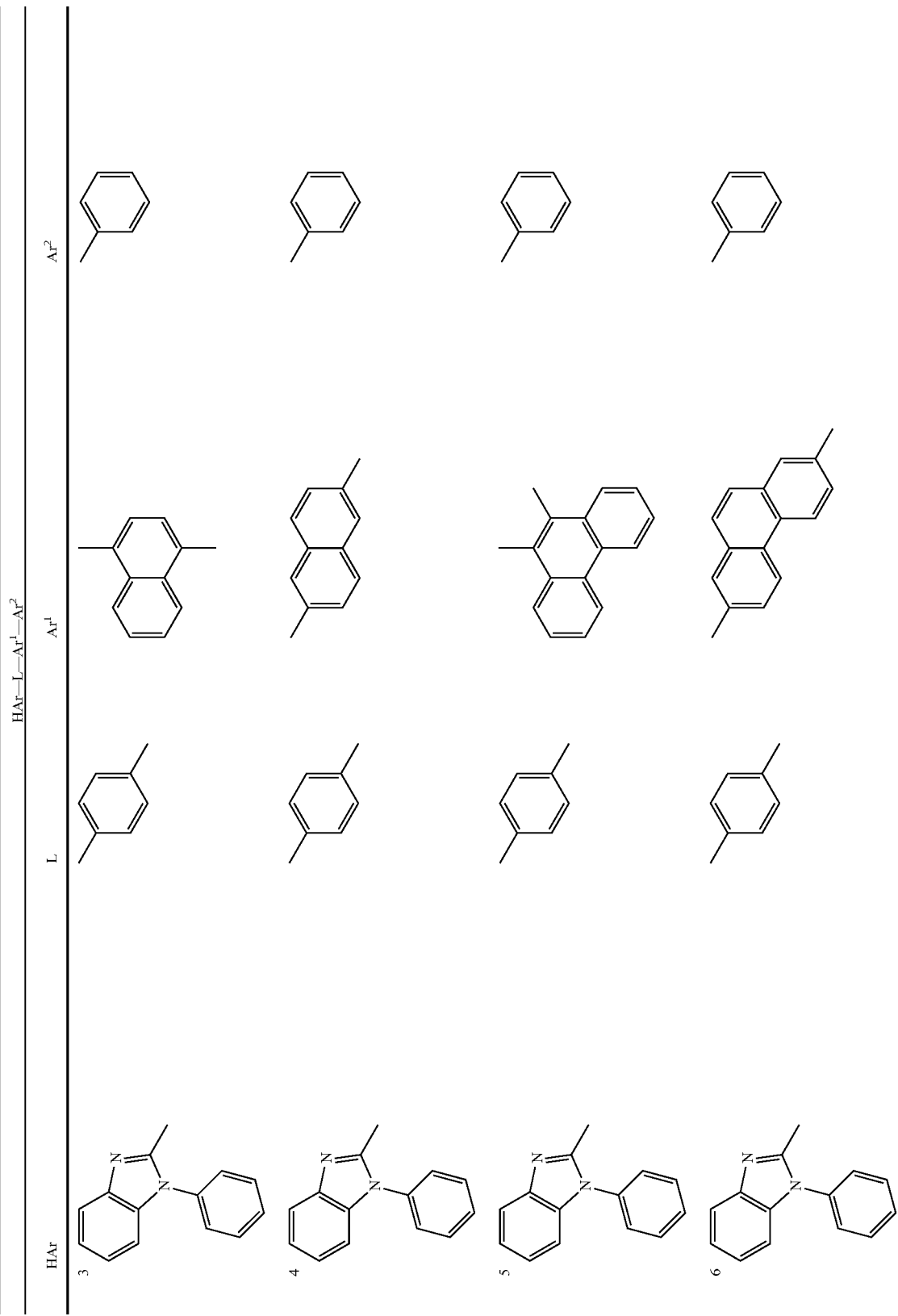

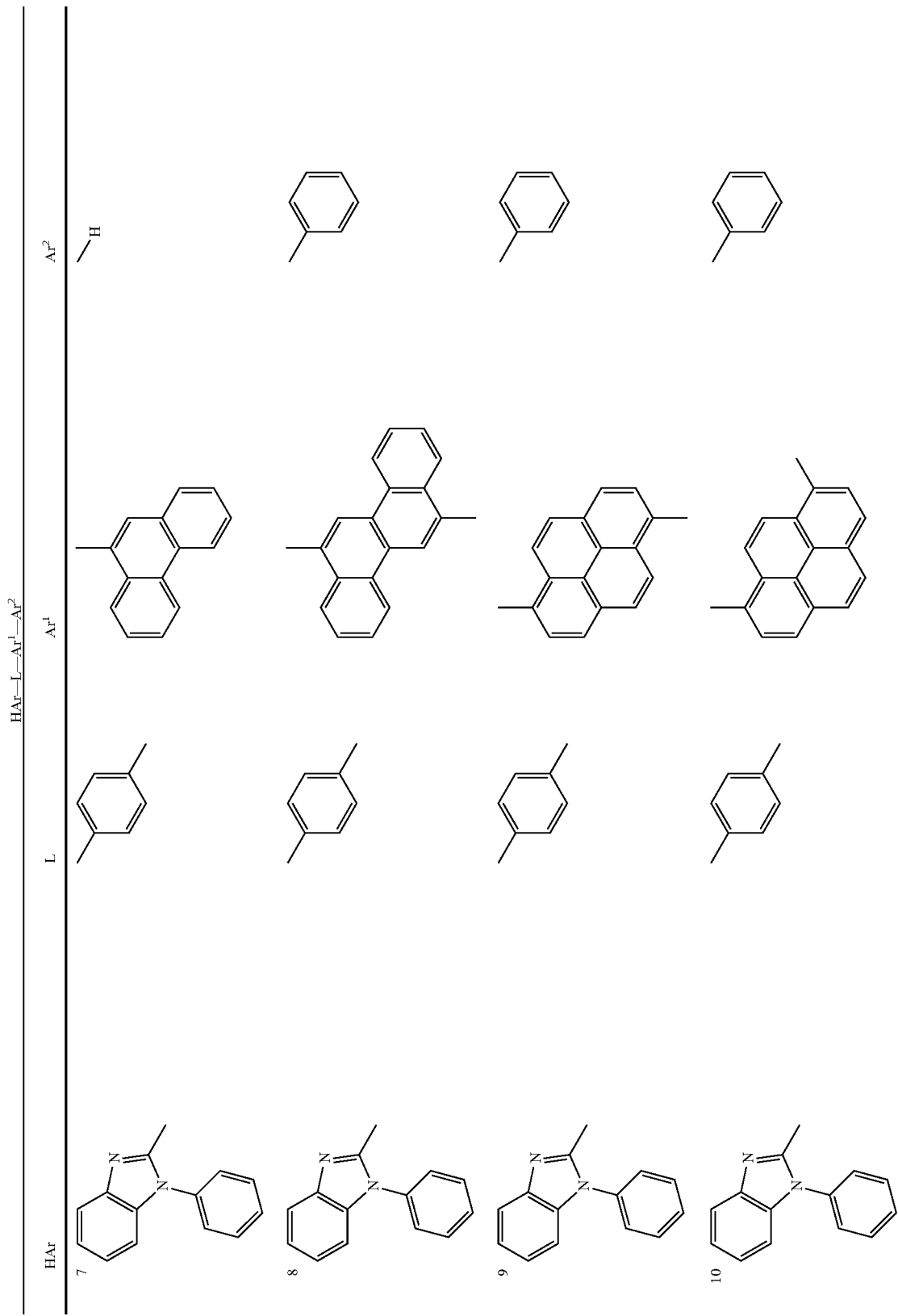

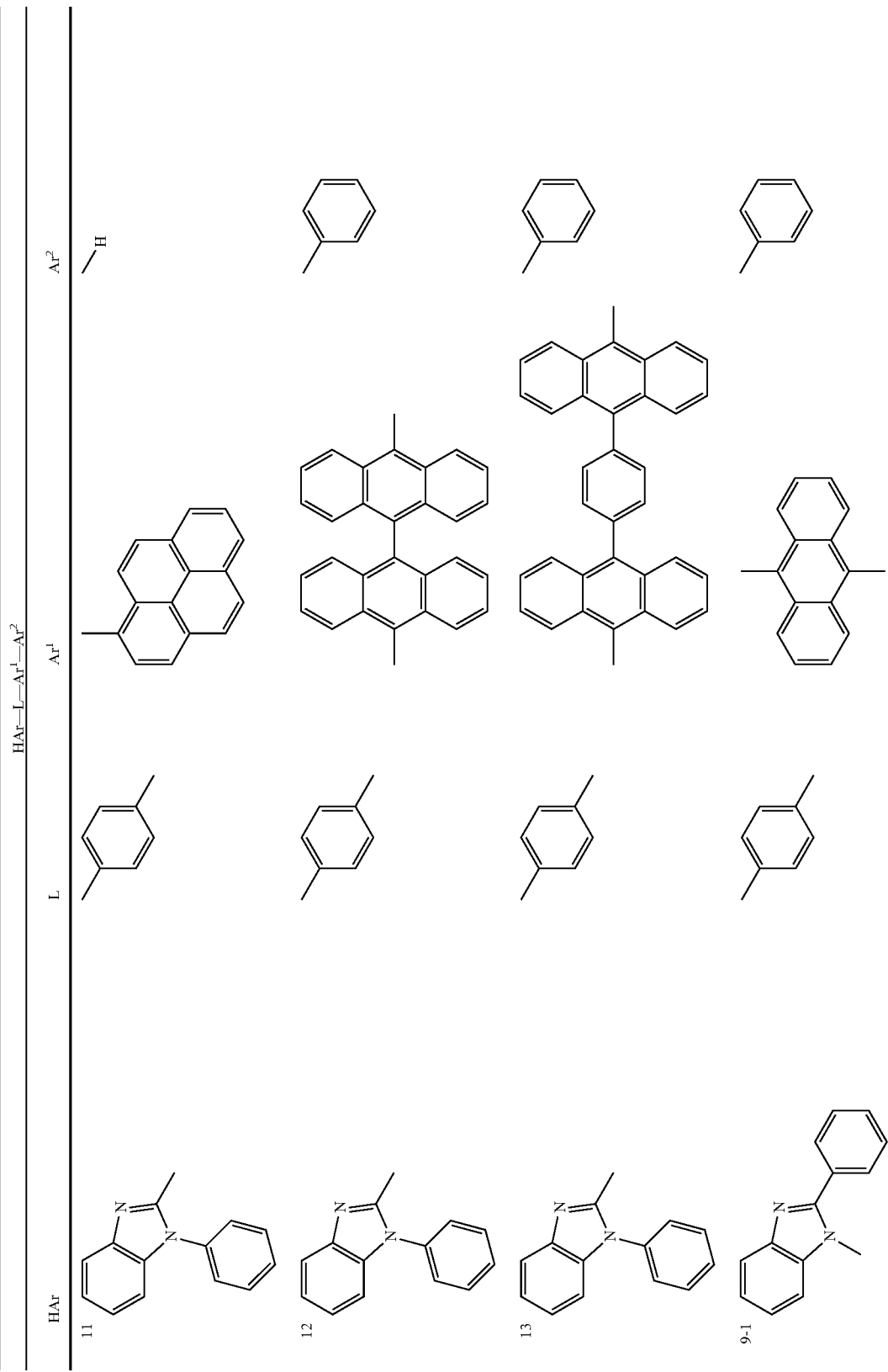

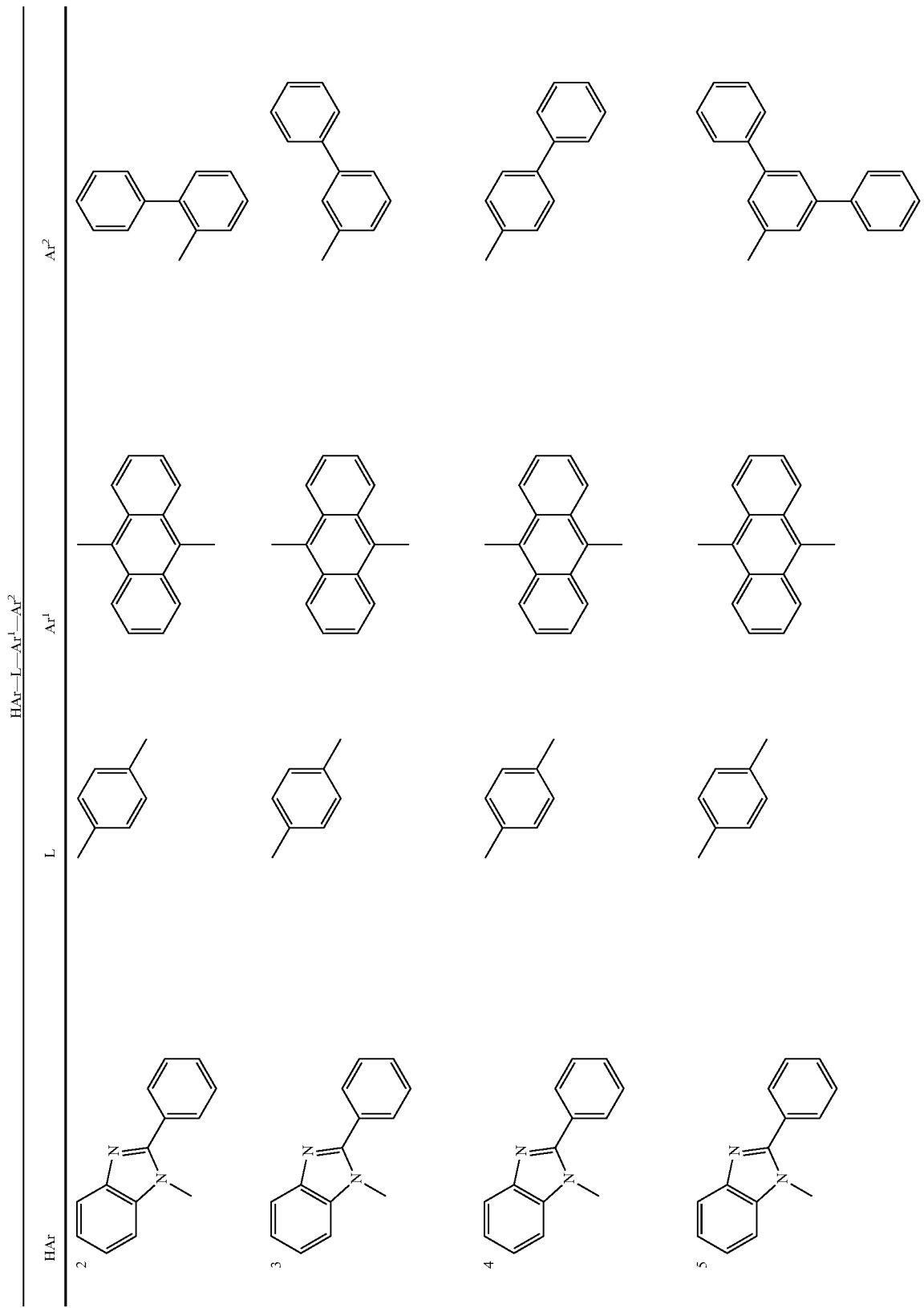

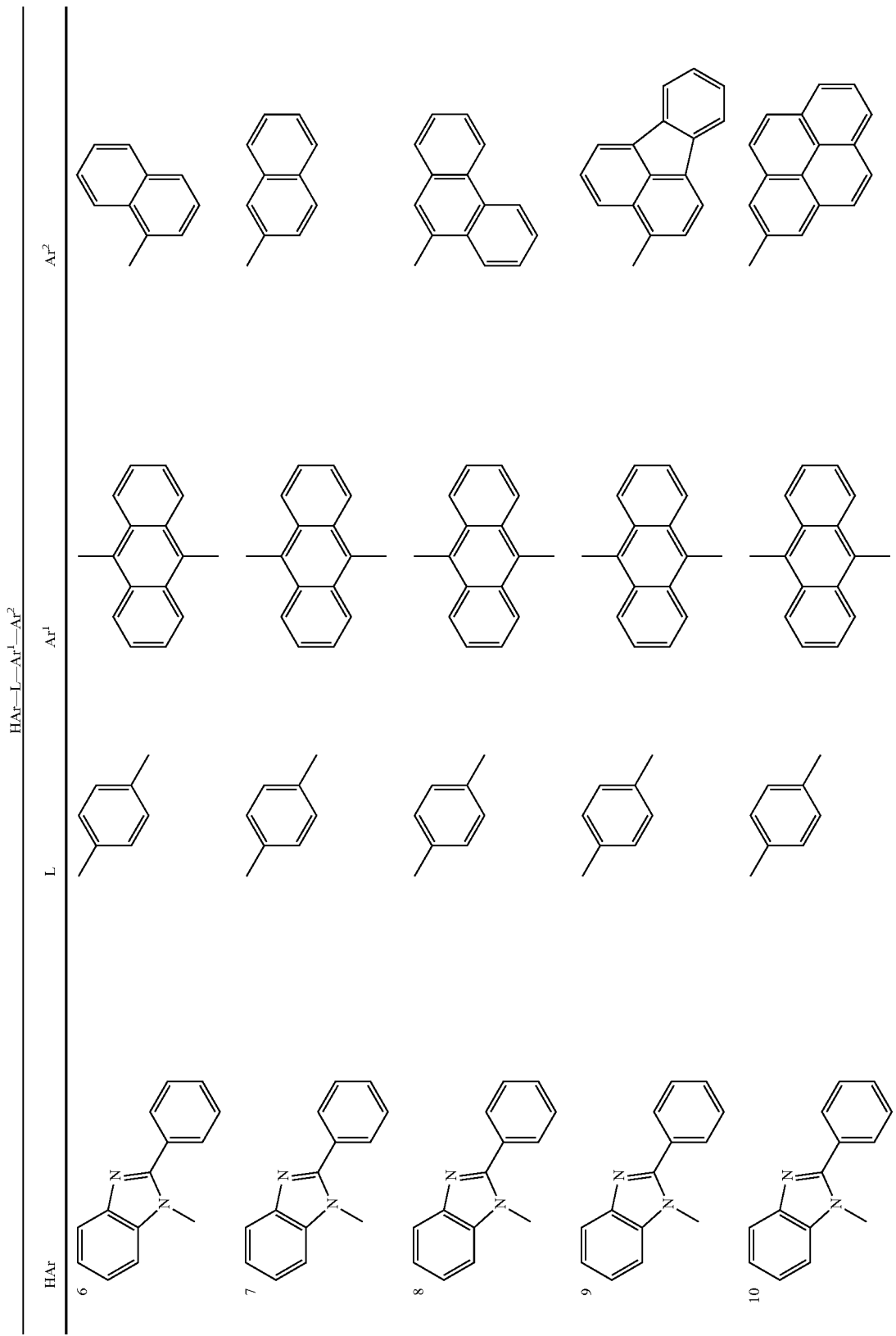

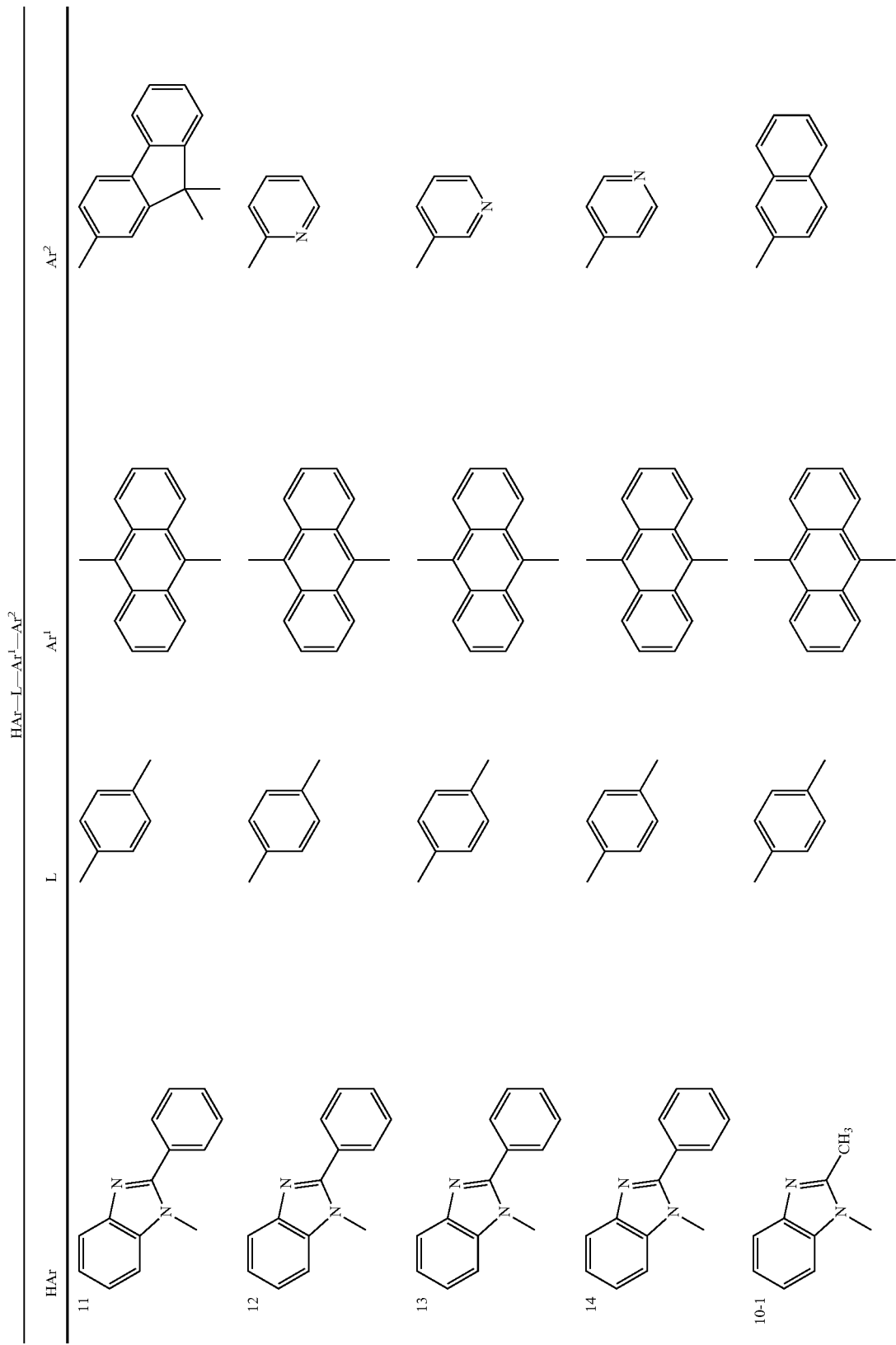

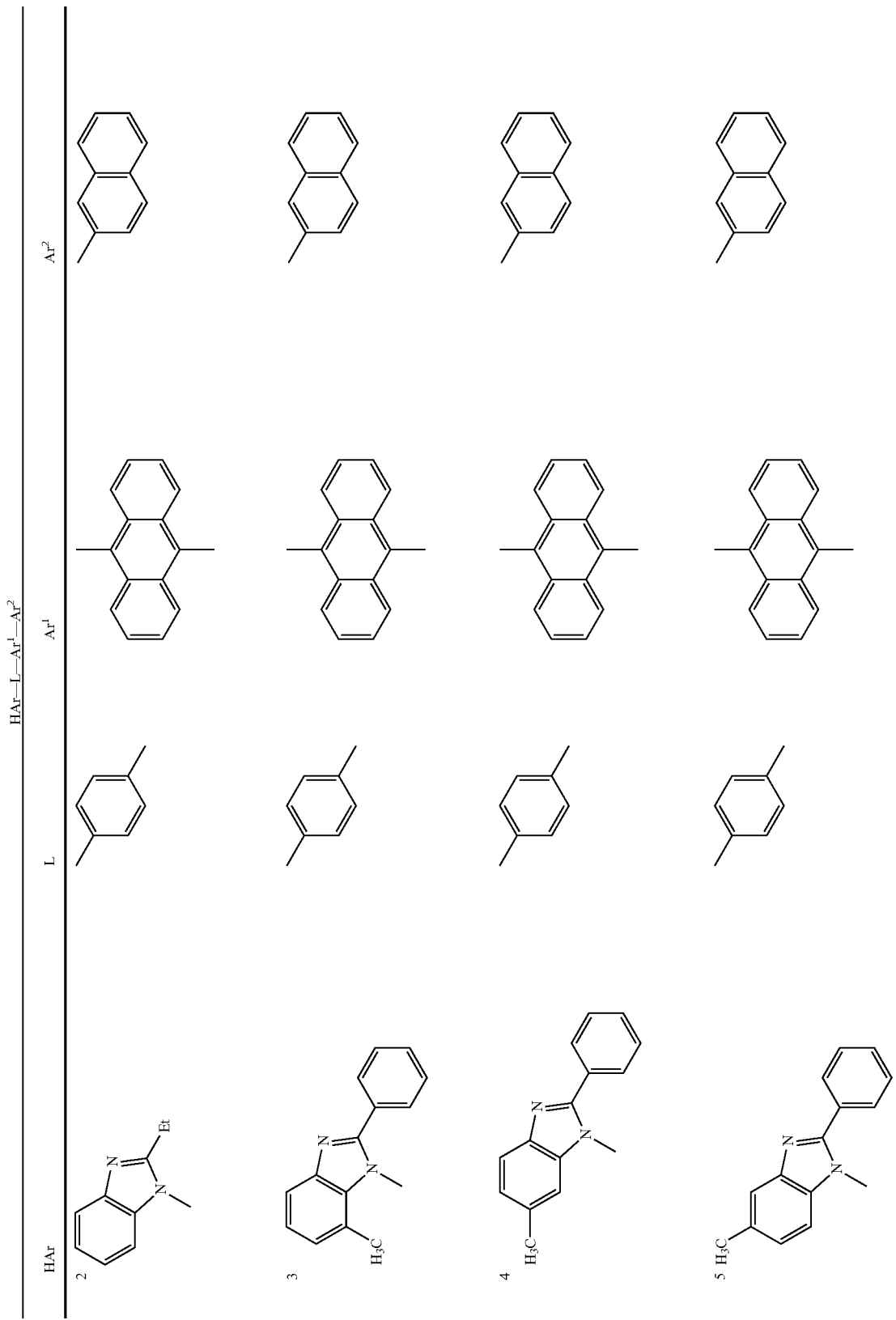

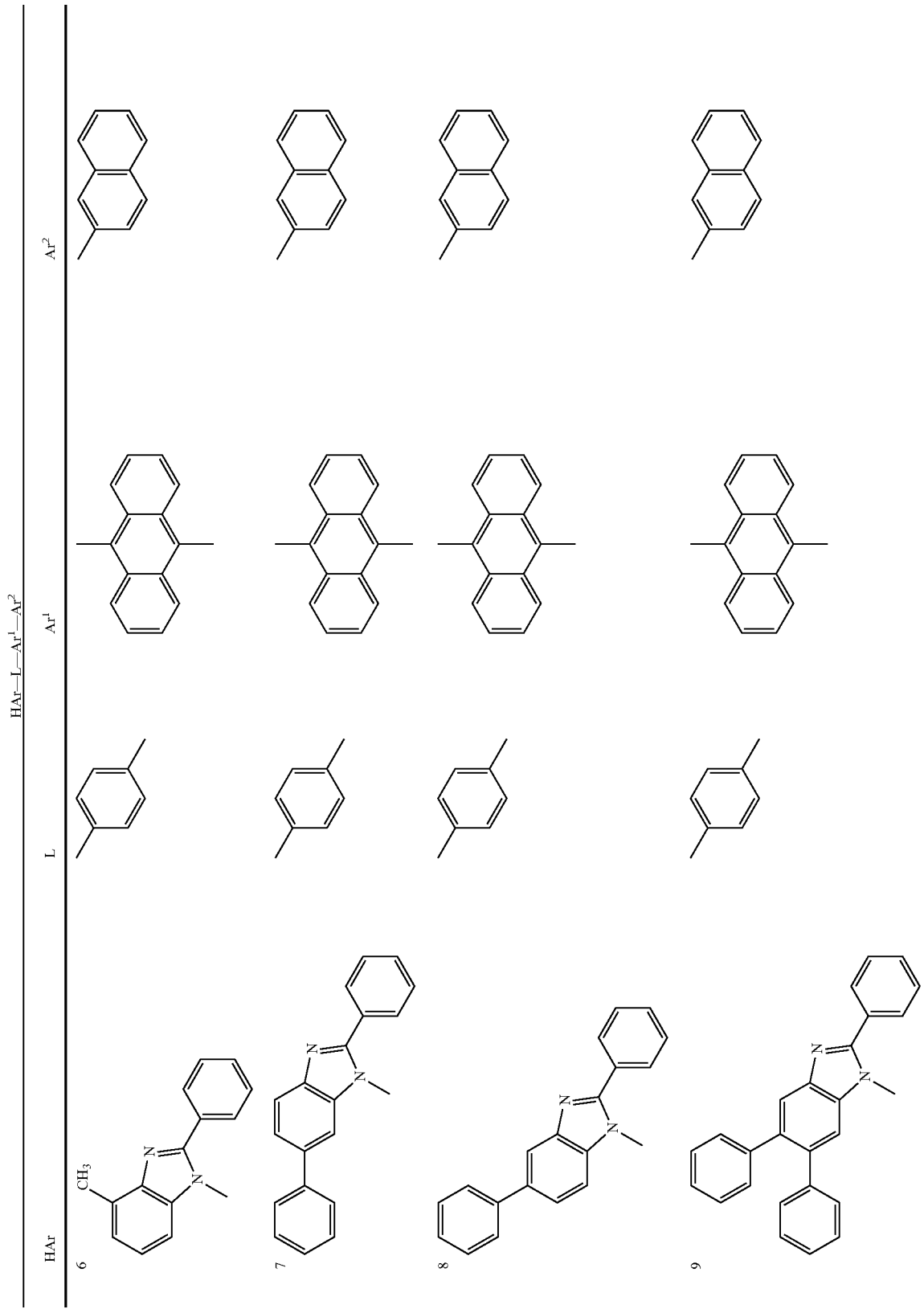

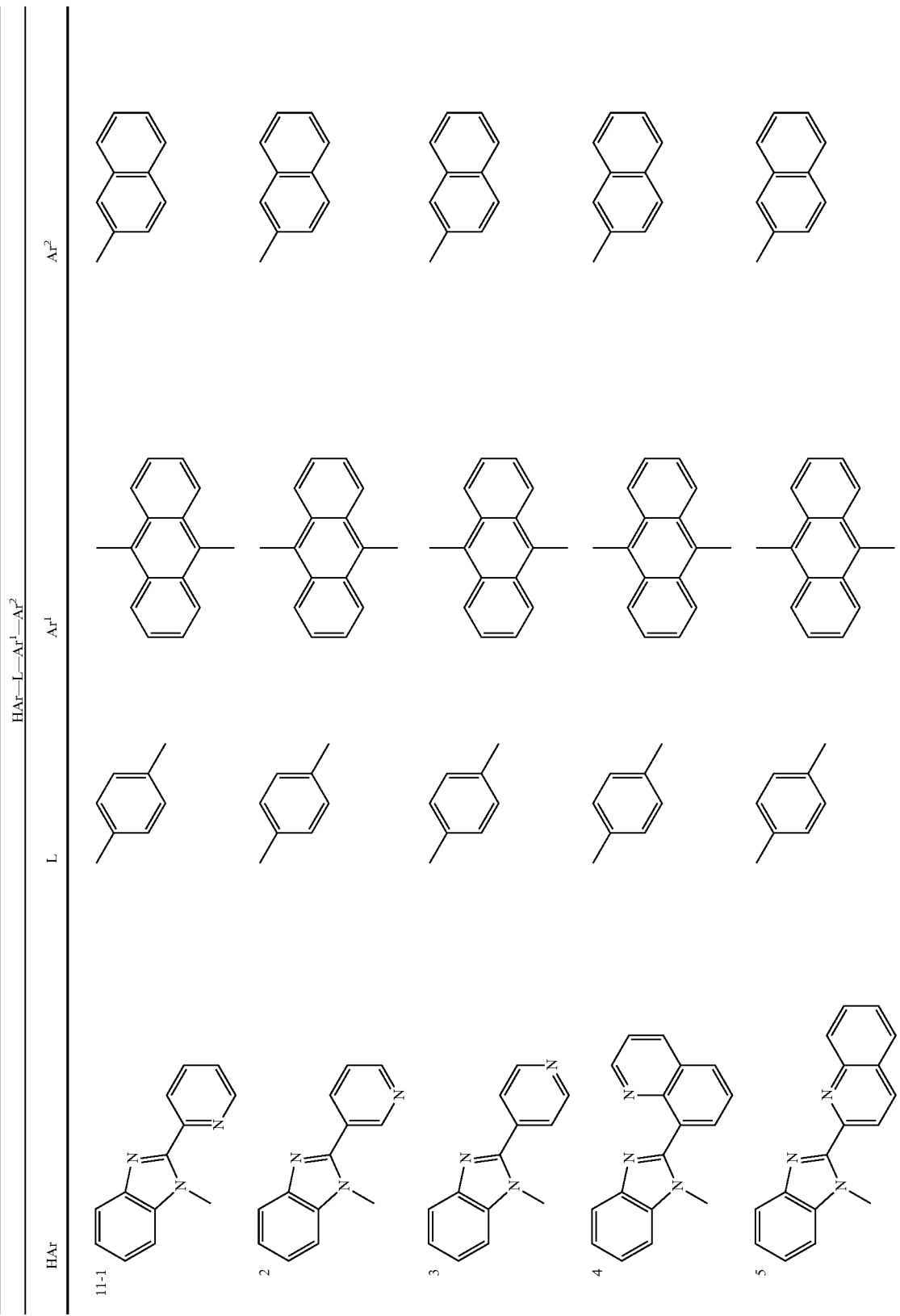

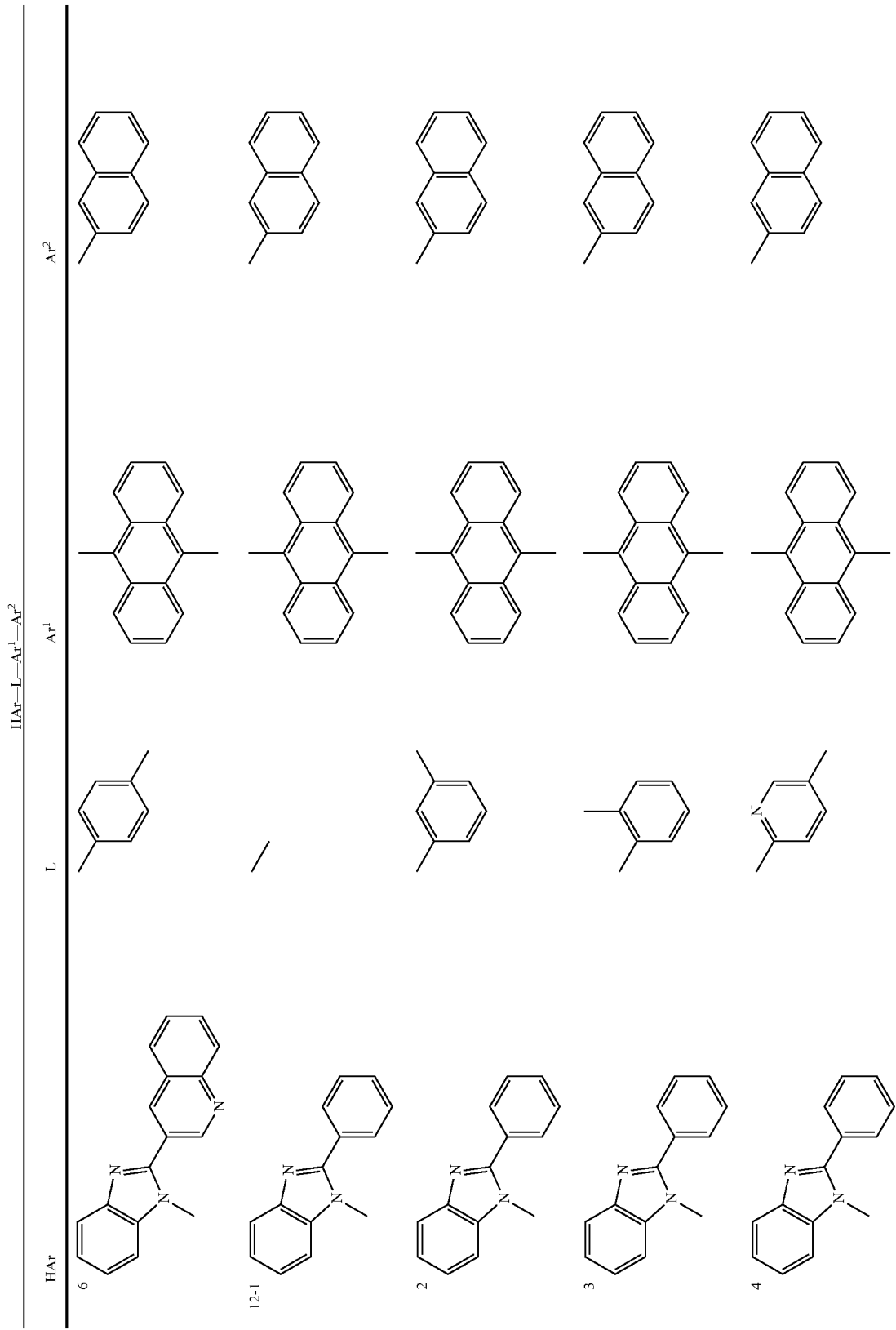

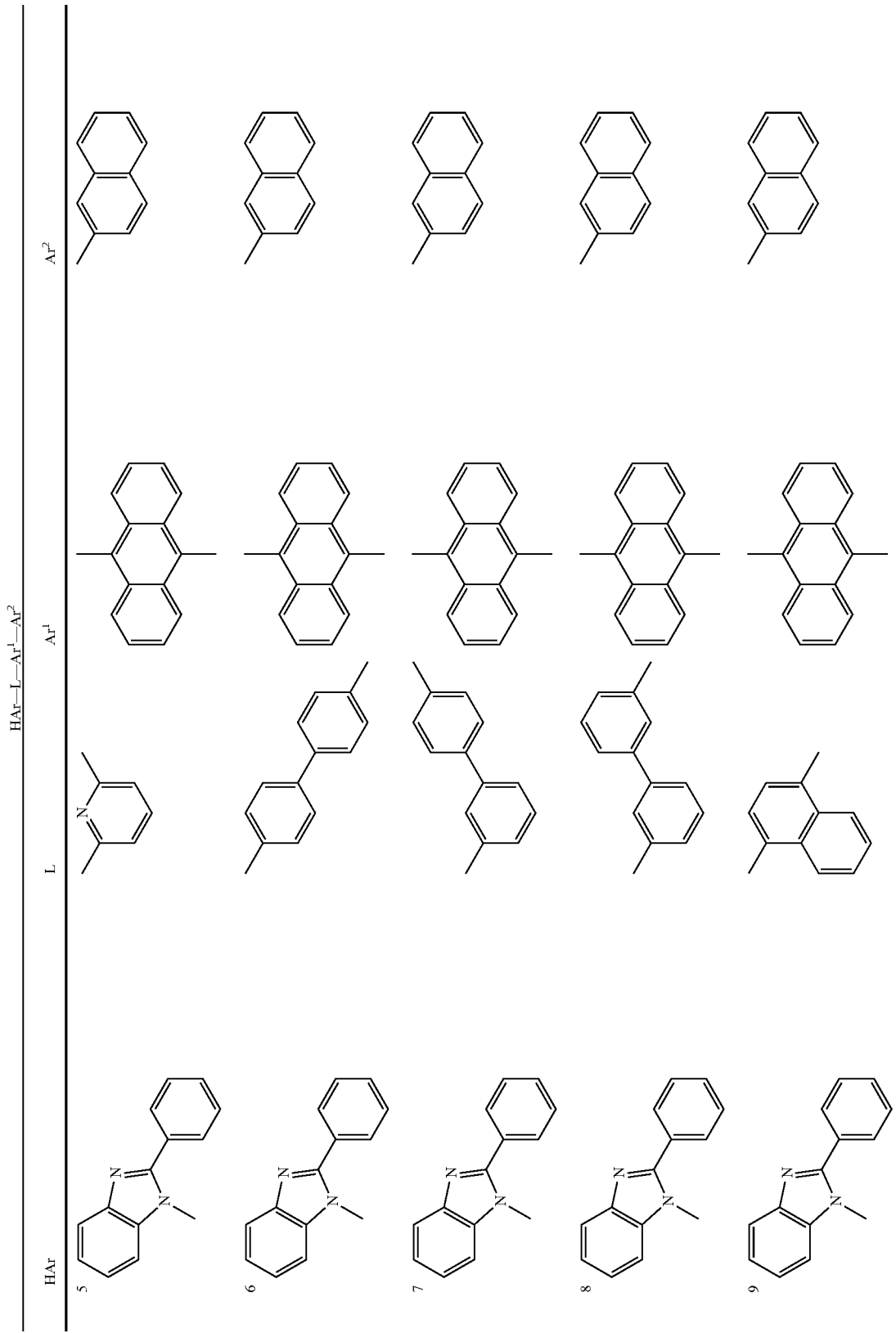

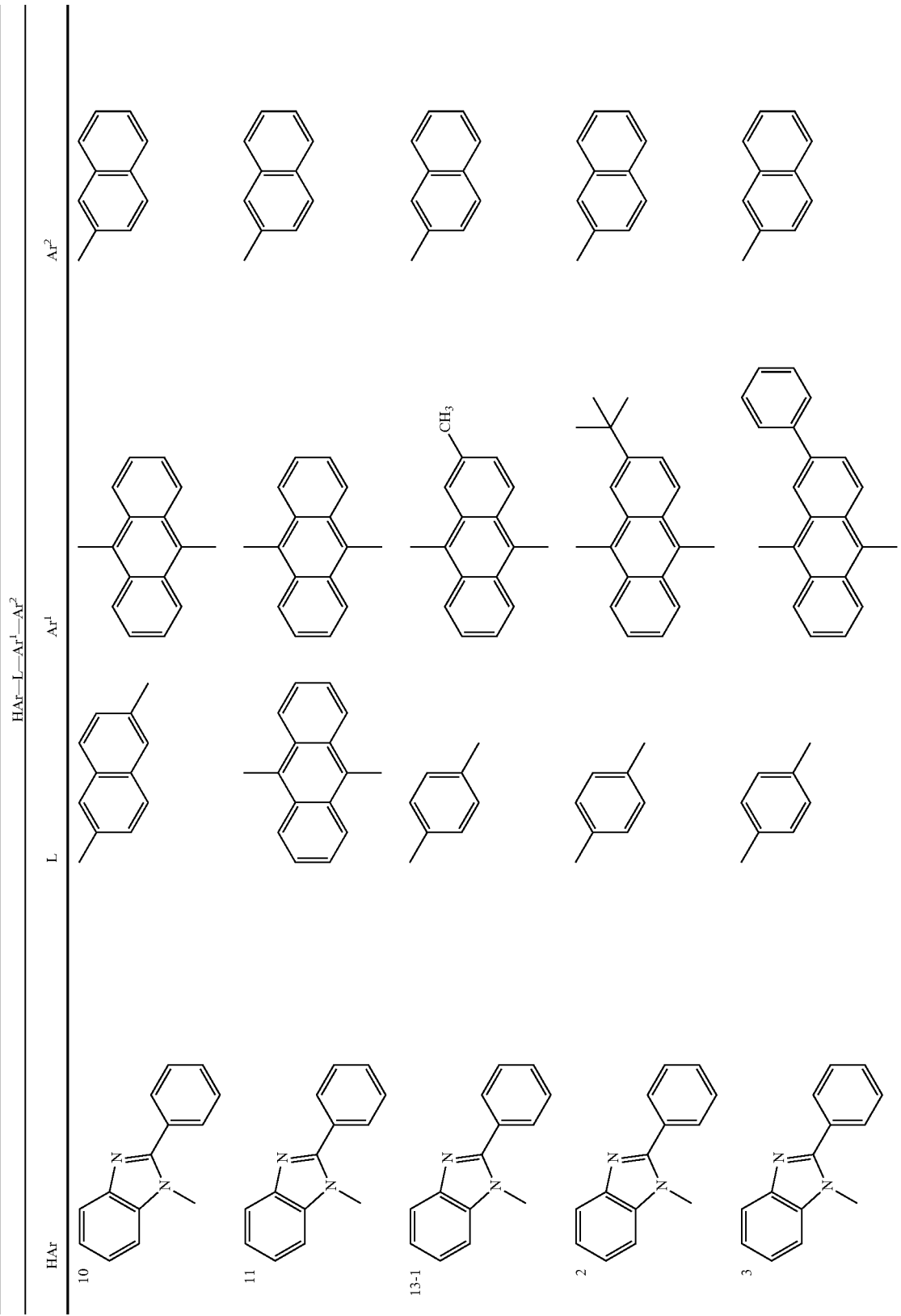

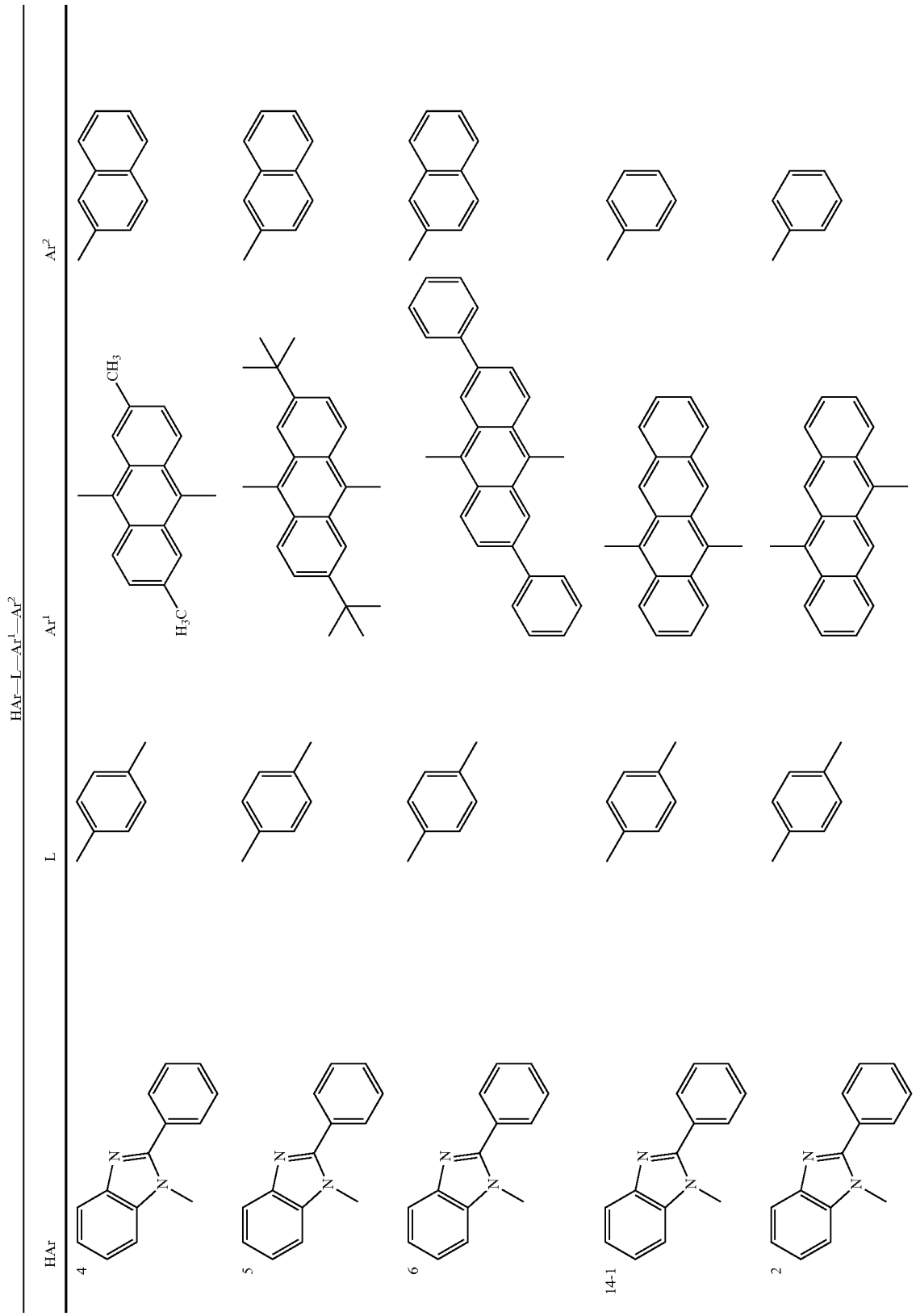

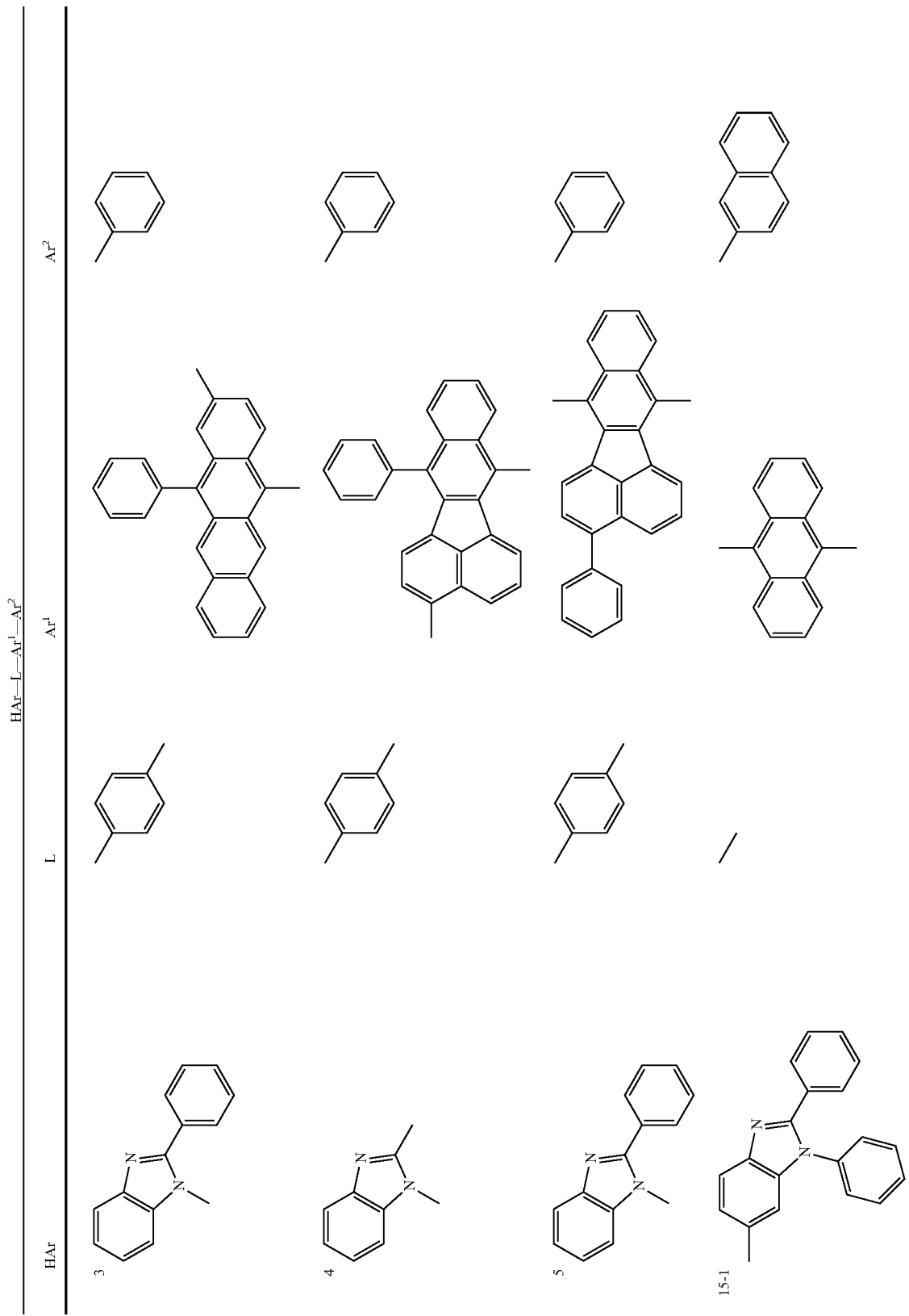

-continued

| HAr | L | Ar¹ | Ar² |
|---|---|---|---|
| 2 (2-methyl-1,3-diphenyl benzimidazole) | / | 9,10-disubstituted anthracene | 2-methylnaphthalene |
| 3 (4-methyl-1,3-diphenyl benzimidazole) | / | 9,10-disubstituted anthracene | 2-methylnaphthalene |
| 4 (7-methyl-1,3-diphenyl benzimidazole) | / | 9,10-disubstituted anthracene | 2-methylnaphthalene |

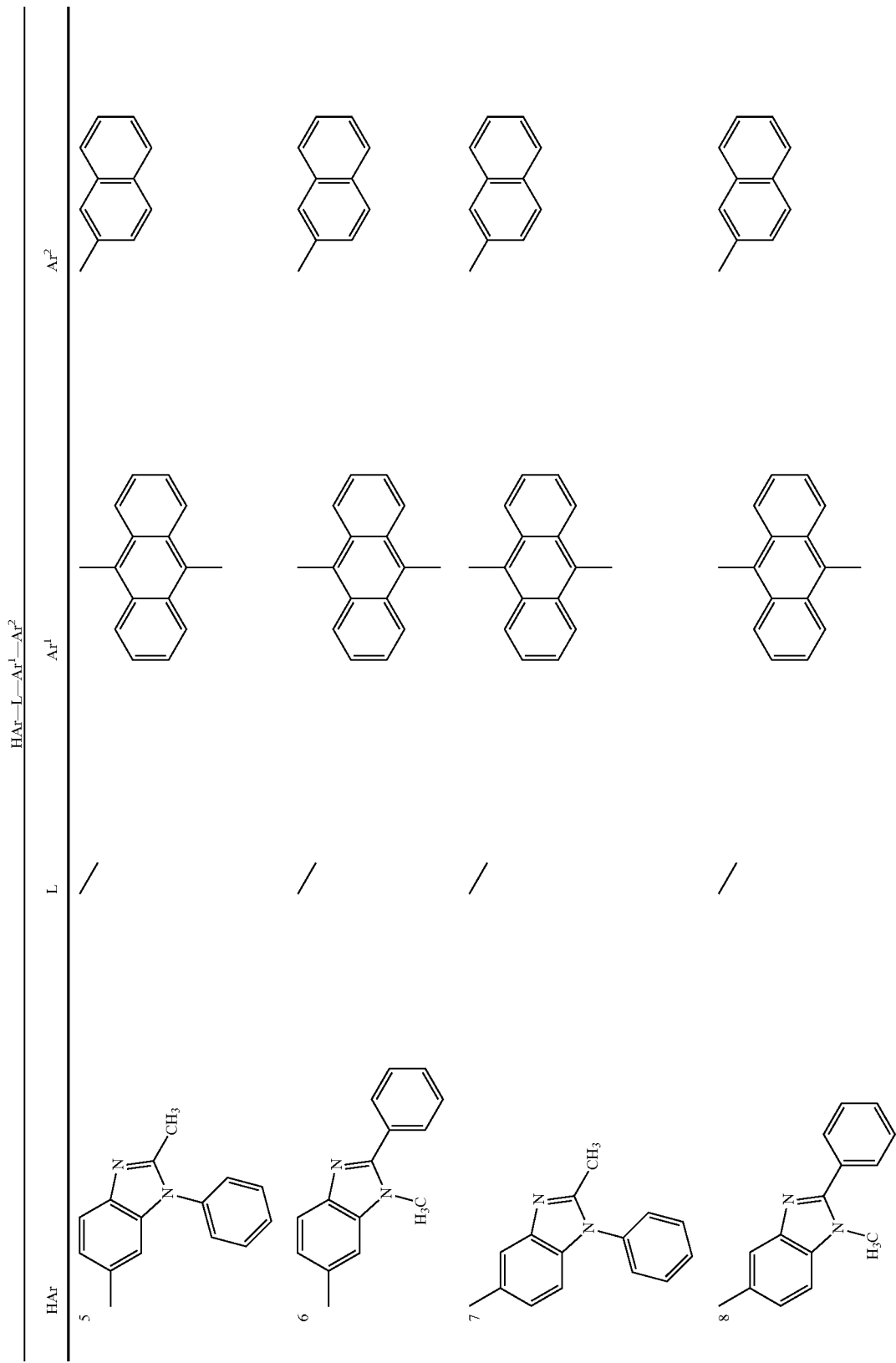

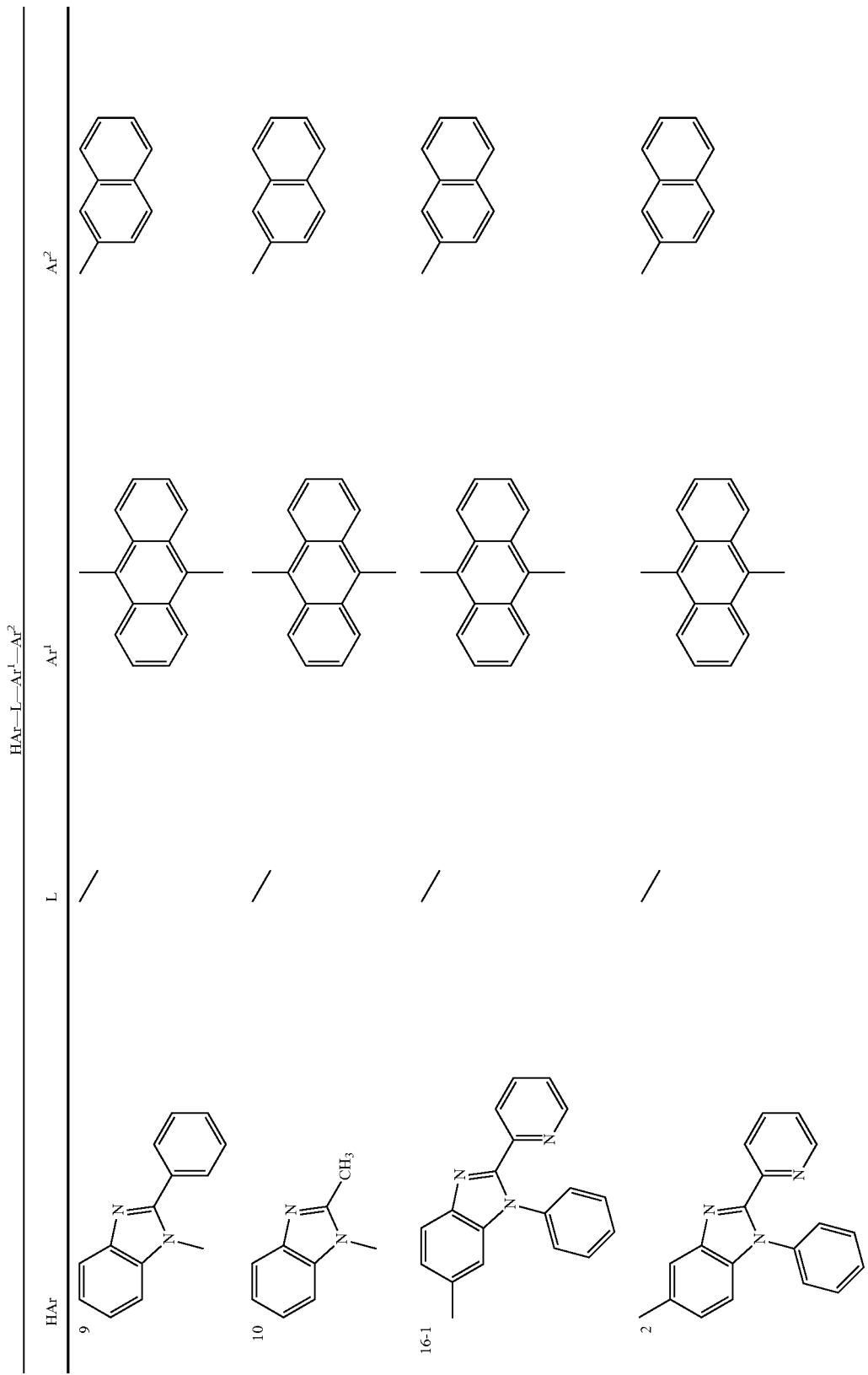

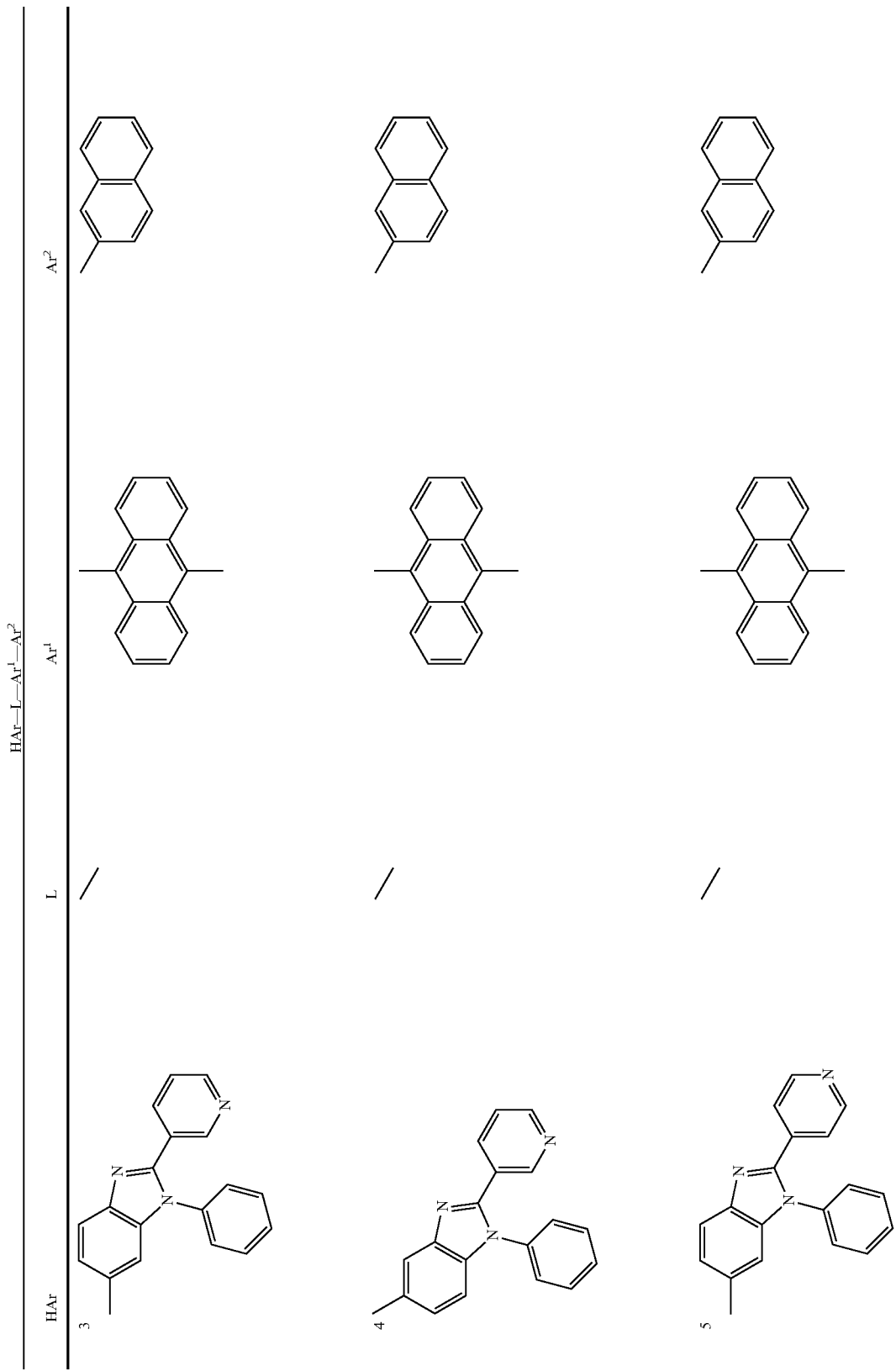

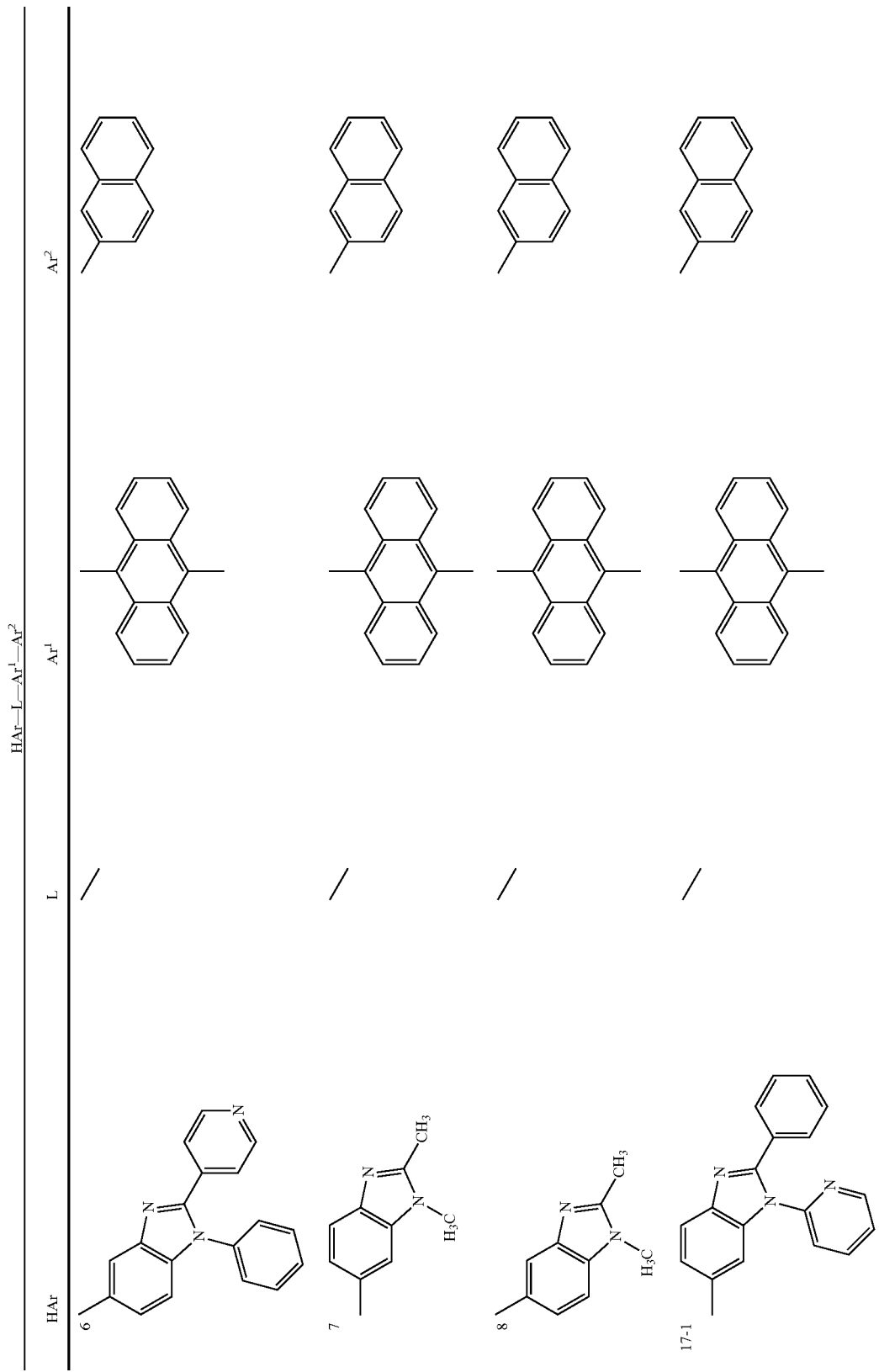

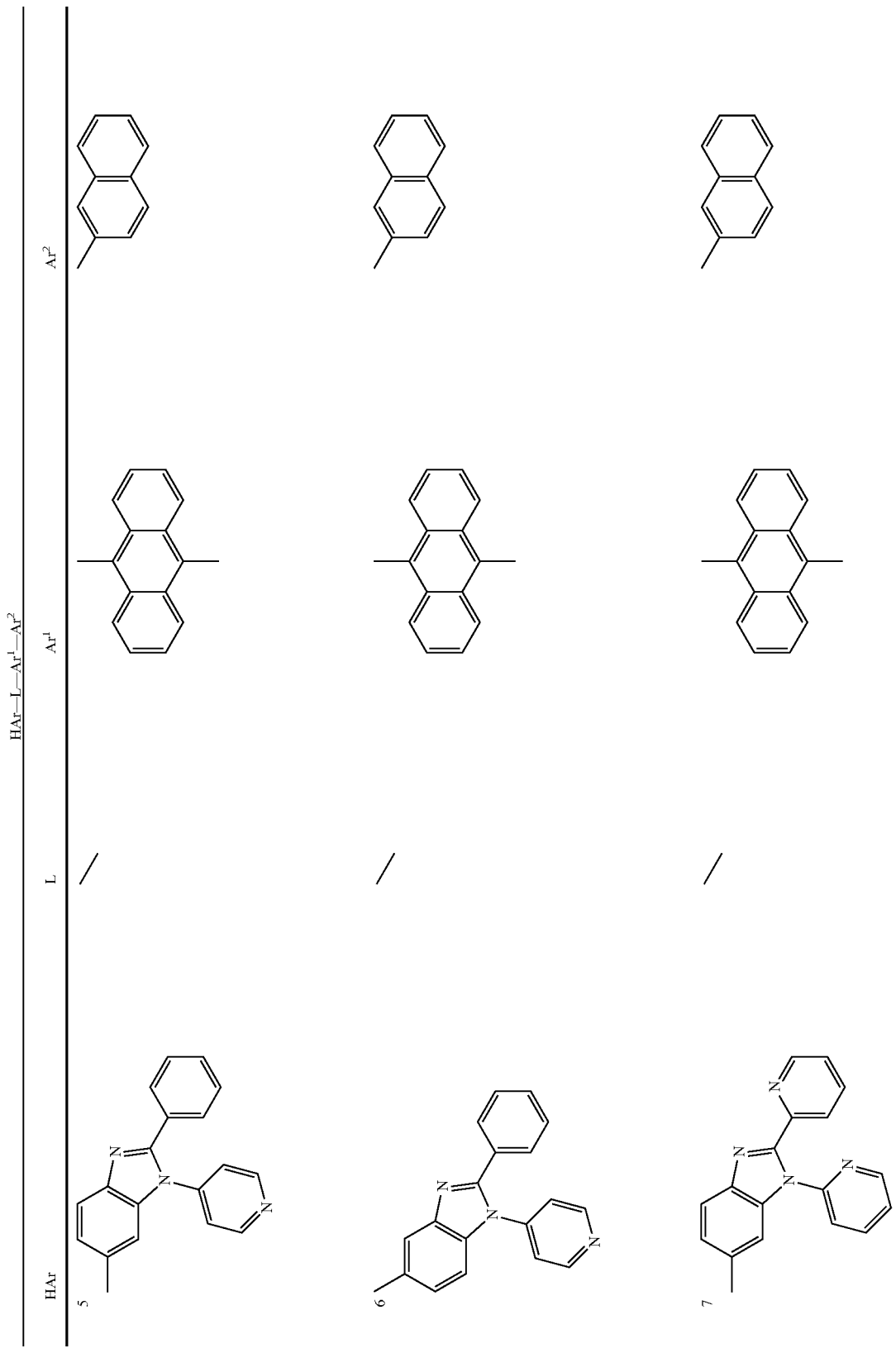

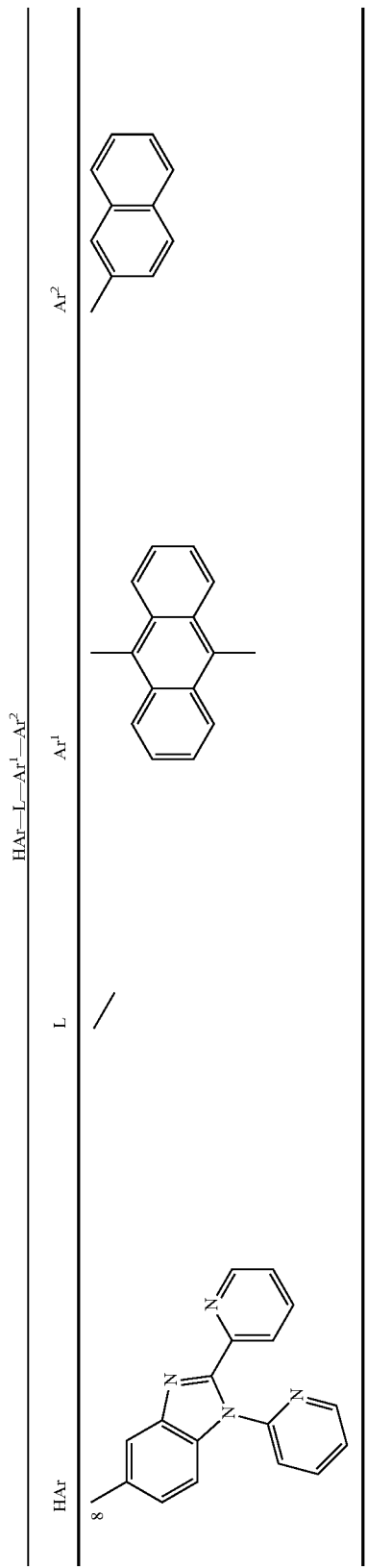

Among the above examples, examples (1-1), (1-5), (1-7), (2-1), (3-1), (4-2), (7-2), (7-7), (7-8), (7-9), (9-1) and (9-7) are particularly preferred.

Although thickness of the electron injecting layer or the electron transporting layer is not specifically limited, the thickness is preferably 1 to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability of the electron injecting layer.

As the insulator, it is preferable to use at least one metal compound selected from a group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film. When the electron injecting layer is formed of such semiconductor film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

When the electron injecting layer contains such an insulator or such a semiconductor, a thickness thereof is preferably in a range of approximately 0.1 to 15 nm. The electron injecting layer according to the aspect of the invention may preferably contain the above-described reductive dopant.

The hole injecting layer or the hole transporting layer (including the hole injecting/transporting layer) may contain an aromatic amine compound such as an aromatic amine derivative represented by the following (I).

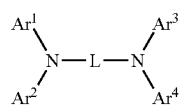
(I)

In the above (I), $Ar^1$ to $Ar^4$ each represent a substituted or unsubstituted aryl group having 6 to 50 carbon atoms for forming a ring or a substituted or unsubstituted heteroaryl group having 5 to 50 atoms for forming a ring.

Examples of the substituted or unsubstituted aryl group having 6 to 50 ring carbon atoms are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group and the like.

Examples of the substituted or unsubstituted heteroaryl group having 5 to 50 ring atoms are a 1-pyroryl group, 2-pyroryl group, 3-pyroryl group, pyrazinyl group, 2-pyridiny group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like. Among the above, a phenyl group, a naphthyl group, biphenyl group, anthranil group, phenanthryl group, pyrenyl group, chrysenyl group, fluoranthenyl group, fluorenyl group and the like are preferable.

L represents a link group. Specifically, L represents a substituted or unsubstituted arylene group having 6 to 50 carbon atoms forming a ring, a substituted or unsubstituted heteroarylene group having 5 to 50 atoms forming a ring, a divalent group formed by singly bonding, ether-bonding or thioether-bonding two or more arylene groups, a divalent group formed by bonding two or more arylene groups by alkylene group having 1 to 20 carbon atoms, alkenylene group having 2 to 20 carbon atoms or amino group, a divalent group formed by singly bonding, ether-bonding or thioether-bonding two or more heteroarylene groups, or a divalent group formed by bonding two or more heteroarylene groups by alkylene group having 1 to 20 carbon atoms, alkenylene group having 2 to 20 carbon atoms or amino group. Examples of the arylene group having 6 to 50 ring carbon atoms are a 1,4-phenylene group, 1,2-phenylene group, 1,3-phenylene group, 1,4-naphthylene group, 2,6-naphthylene group, 1,5-naphthylene group, 9,10-anthranylene group, 9,10-phenanthrenylene group, 3,6-phenanthrenylene group, 1,6-pyrenylene group, 2,7-pyrenylene group, 6,12-chrysenylene group, 4-4'-biphenylene group, 3,3'-biphenylene group, 2,2'-biphenylene group, 2,7-fluorenylene group and the like. Examples of the arylene group having 5 to 50 ring atoms are a 2,5-thiophenylene group, 2,5-silolylene group, 2,5-oxadiazolylene and the like. Among the above, a 1,4-phenylene group, 1,2-phenylene group, 1,3-phenylene group, 1,4-naphthylene group, 9,10-anthranylene group, 6,12-chrysenylene group, 4-4'-biphenylene group, 3,3'-biphenylene group, 2,2'-biphenylene group, and 2,7-fluorenylene group are preferable.

When L represents a link group formed of 2 or more arylene groups or 2 or more heteroarylene groups, adjacent arylene groups or adjacent heteroarylene groups may be bonded together via a divalent group to form a new ring. Examples of the divalent group for forming the ring are a tetramethylene group, a pentamethylene group, a hexamethylene group, a diphenylmethane-2,2'-diyl group, a diphenylethane-3,3'-diyl group, a diphenylpropane-4,4'-diyl group and the like.

Examples of a substituent for each of $Ar^1$ to $Ar^4$ and L are an amino group, a halogen atom, a cyano group, a nitro group and a hydroxy group each of which is substituted by a substituted or unsubstituted aryl group having 6 to 50 carbon atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms forming a ring, a substituted or unsubstituted heteroaryloxy group having 6 to 50 carbon atoms forming a ring, a substituted or unsubstituted arylthio group having 6 to 50 atoms forming a ring, a substituted or unsubstituted heteroarylthio group having 5 to 50 atoms forming a ring, a substituted or unsubstituted alkoxycarbonyl group having 2 to 50 carbon atoms, a substituted or unsubstituted aryl group having 6 to 50 carbon atoms forming a ring, or a substituted or unsubstituted heteroaryl group having 5 to 50 atoms forming a ring.

Examples of the substituted or unsubstituted aryl group having 6 to 50 ring carbon atoms are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group and the like.

Examples of the substituted or unsubstituted heteroaryl group having 5 to 50 ring atoms are a 1-pyroryl group, 2-pyroryl group, 3-pyroryl group, pyrazinyl group, 2-pyridiny group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

Examples of the substituted or unsubstituted alkyl group having 1 to 50 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted cycloalkyl group having 3 to 50 carbon atoms are a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group and the like.

The substituted or unsubstituted alkoxy group having 1 to 50 carbon atoms is a group represented by —OY. Examples of Y are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted aralkyl group having 7 to 50 carbon atoms are a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like.

The substituted or unsubstituted aryloxy group having 6 to 50 ring carbon atoms is represented by —OY'. Examples of Y' are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group and the like.

The substituted or unsubstituted heteroaryloxy group having 5 to 50 ring atoms is represented by —OZ'. Examples of Z' are a 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The substituted or unsubstituted arylthio group having 6 to 50 ring carbon atoms is represented by —SY'. Examples of Y' are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

The substituted or unsubstituted heteroarylthio group is represented by —SZ". Examples of Z" are a 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8- phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The substituted or unsubstituted alkoxycarbonyl group having 2 to 50 carbon atoms is a group represented by —COOZ. Examples of Z are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

The amino group substituted by the substituted or unsubstituted aryl group having 6 to 50 ring carbon atoms or the substituted or unsubstituted heteroaryl group having 5 to 50 ring atoms is represented by —NPQ. Examples of P and Q are a phenyl group, 1-naphthyl group, 2-naphtyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.
Examples of the compound represented by the above (I) are shown below. However, the compound is not limited thereto.
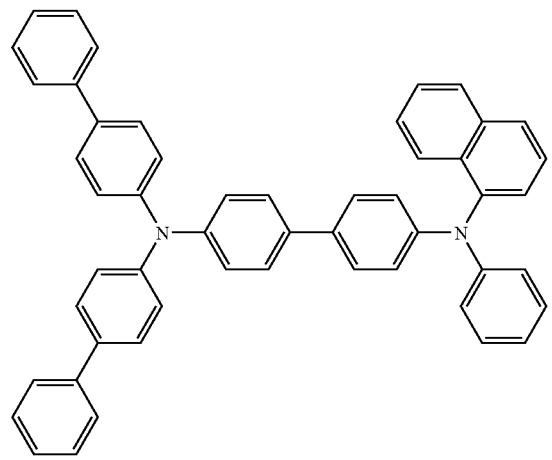
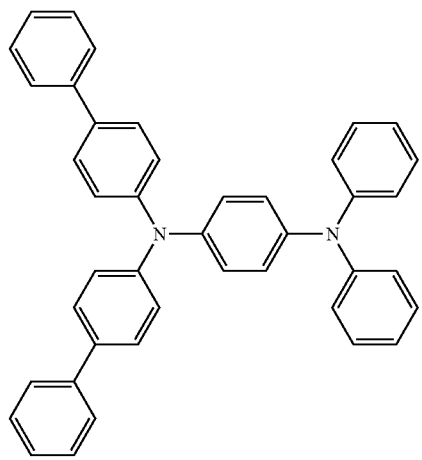
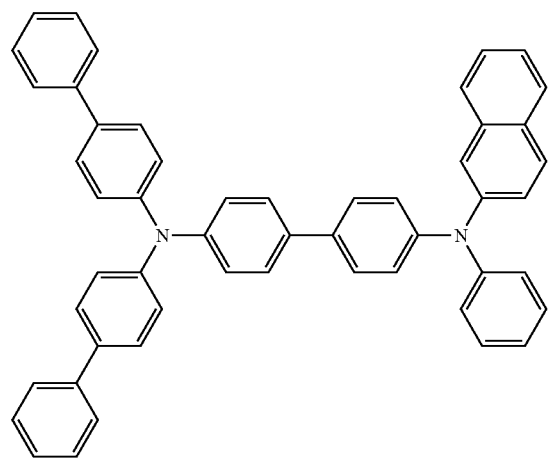
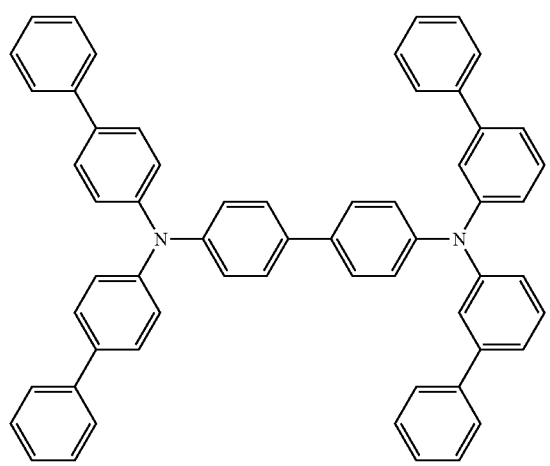
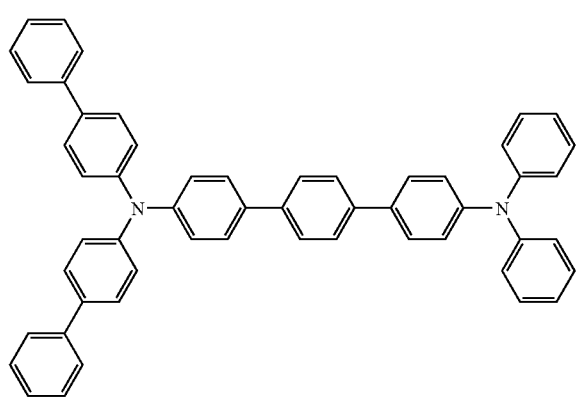
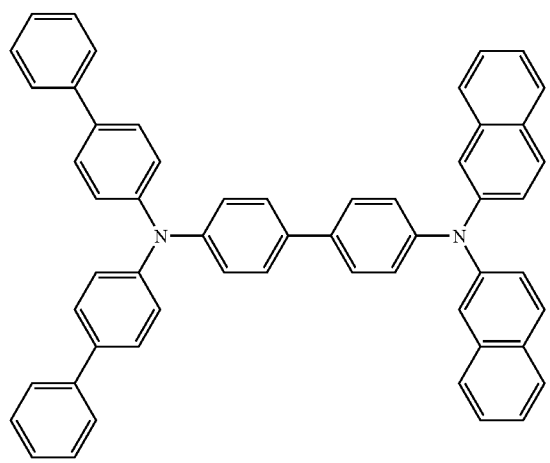

171
-continued
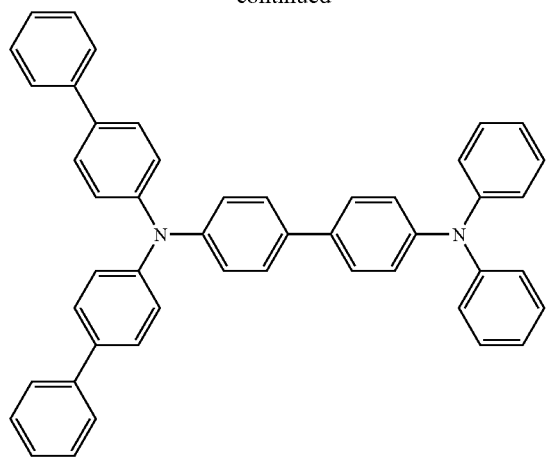
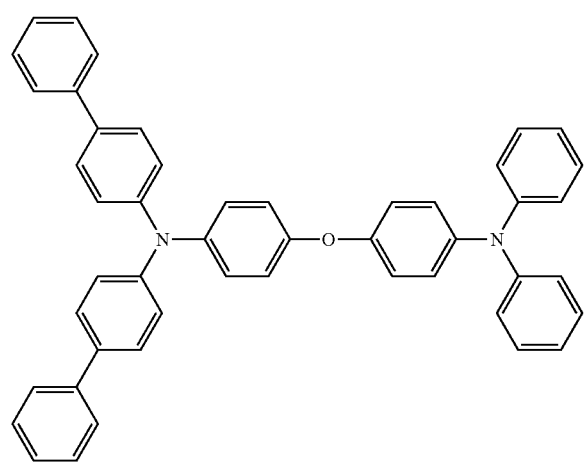
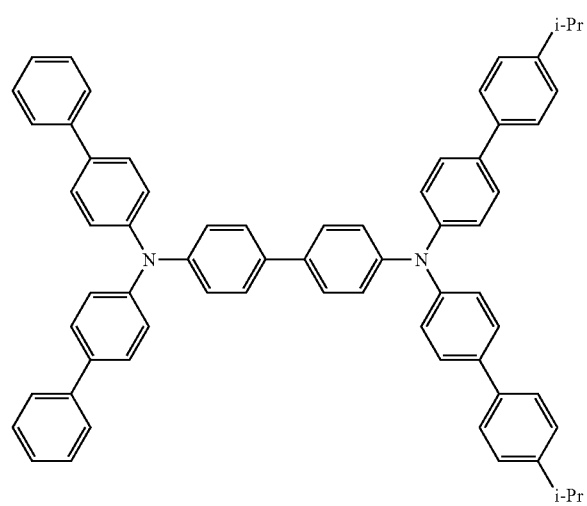
172
-continued
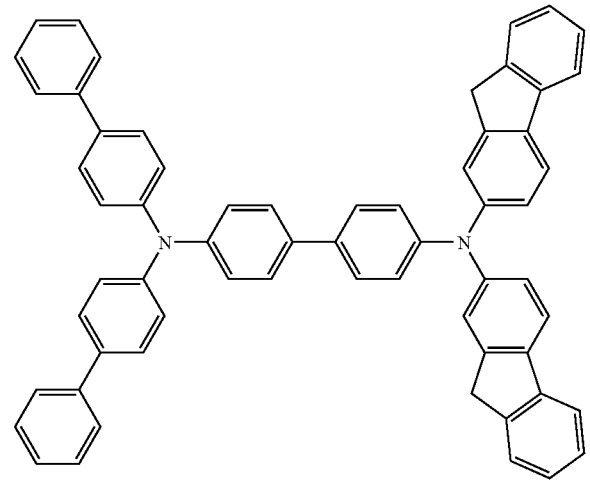
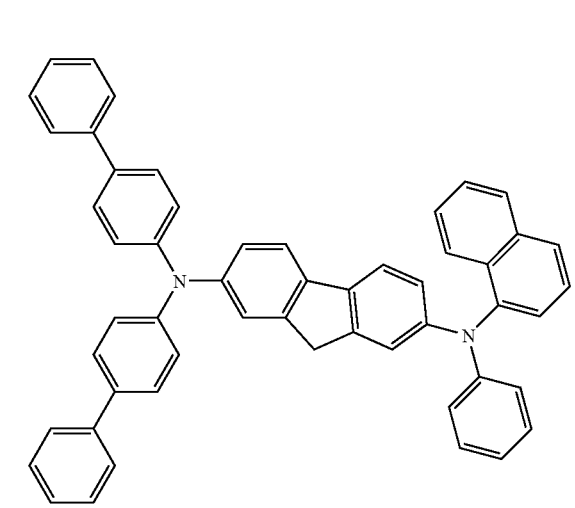

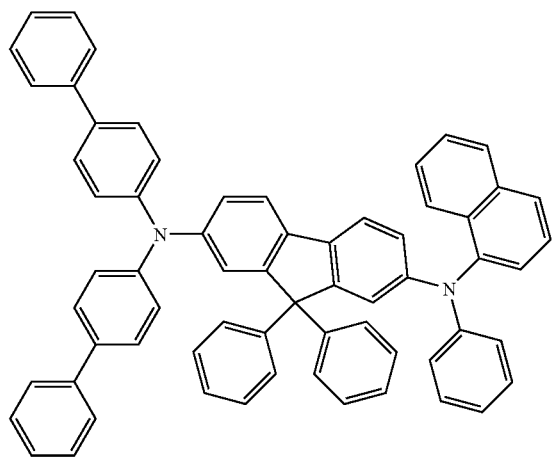
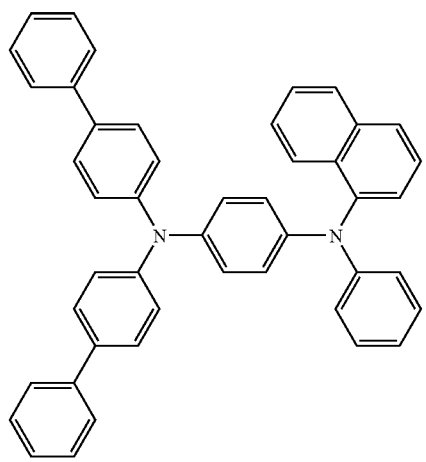
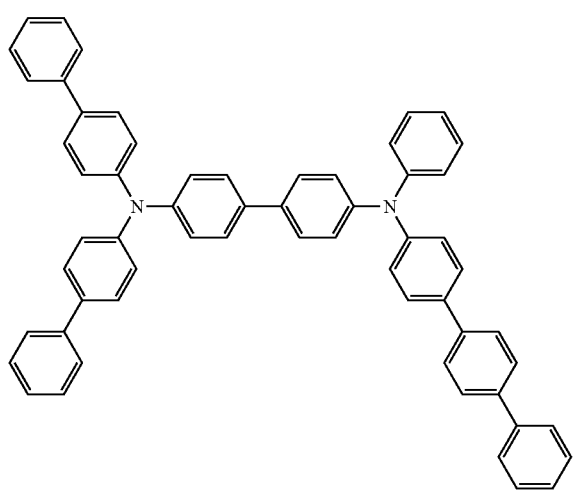
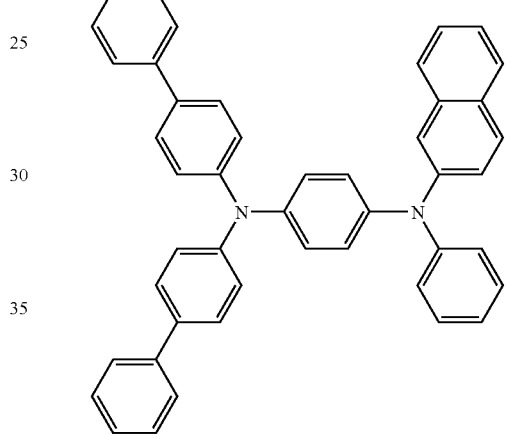
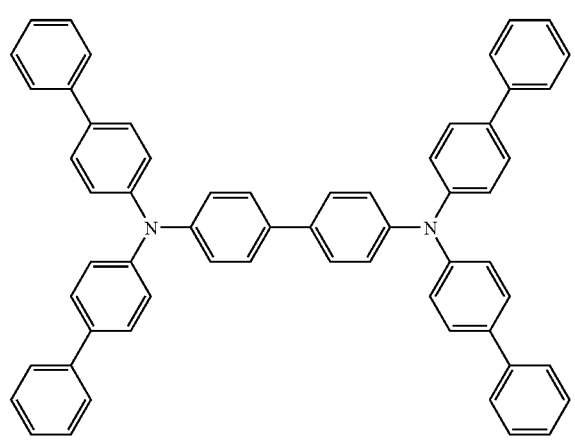
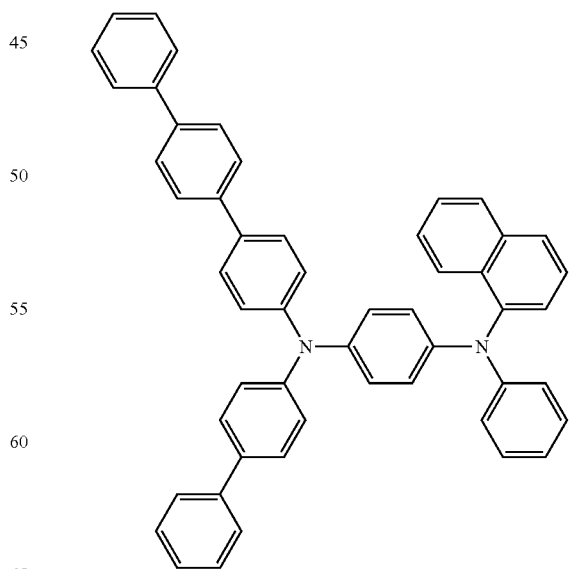

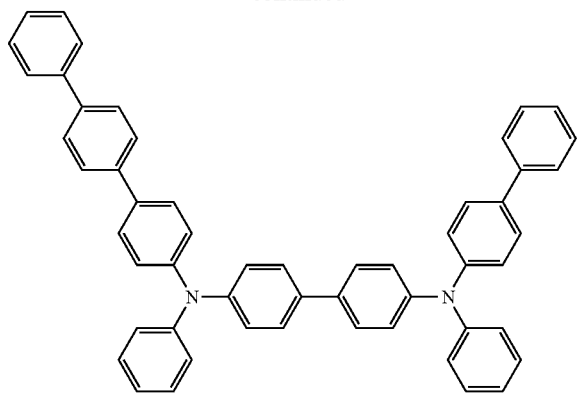
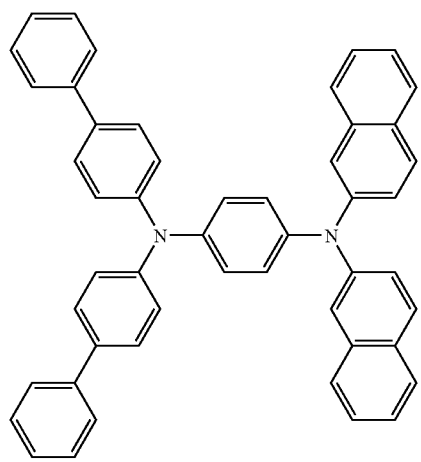
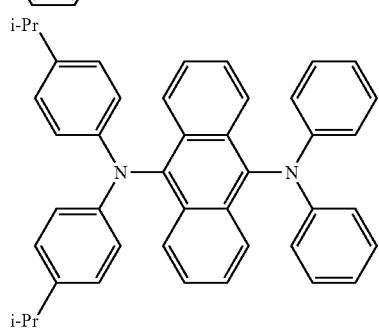
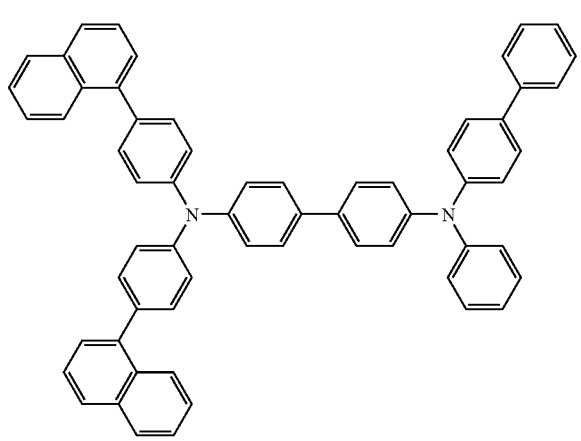
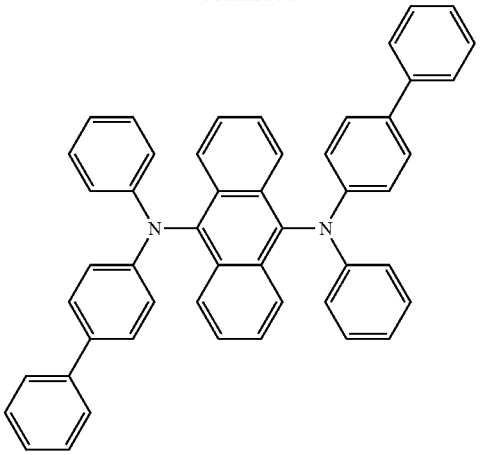

Aromatic amine represented by the following (II) can also be preferably used for forming the hole injecting layer or the hole transporting layer.

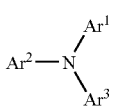

(II)

In the above (II), $Ar^1$ to $Ar^3$ each represent the same as those represented by $Ar^1$ to $Ar^4$ of the above (I). Examples of the compound represented by the above (II) are shown below. However, the compound is not limited thereto.

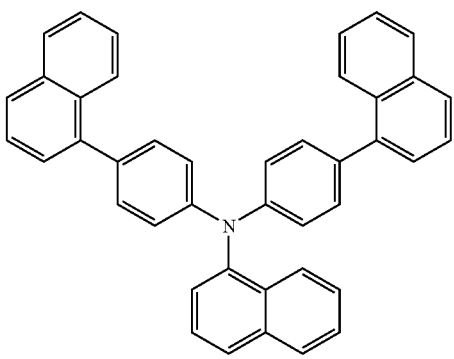
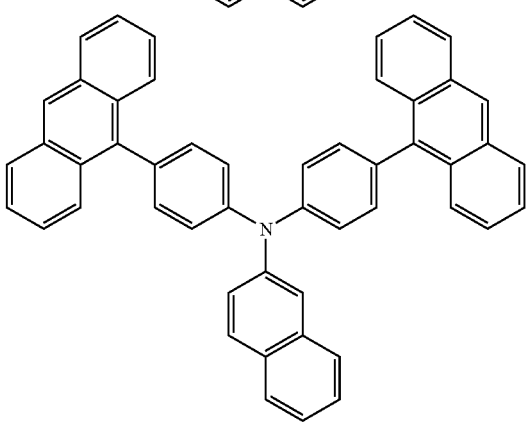

177
-continued
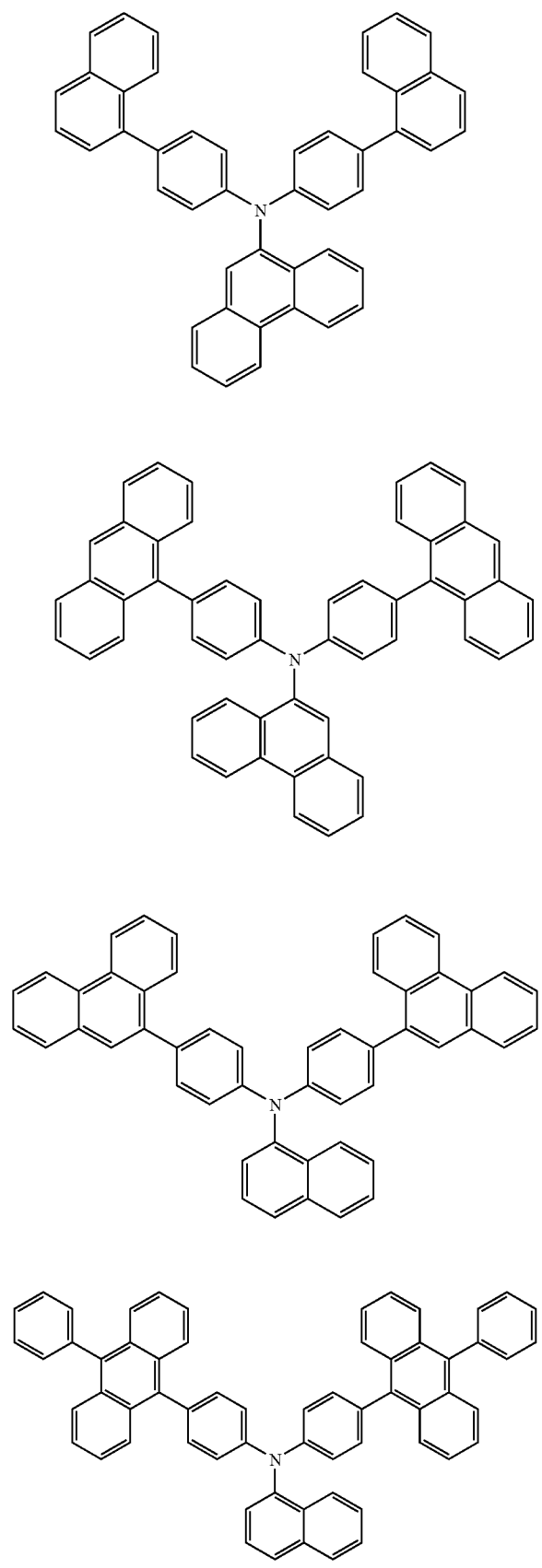
178
-continued
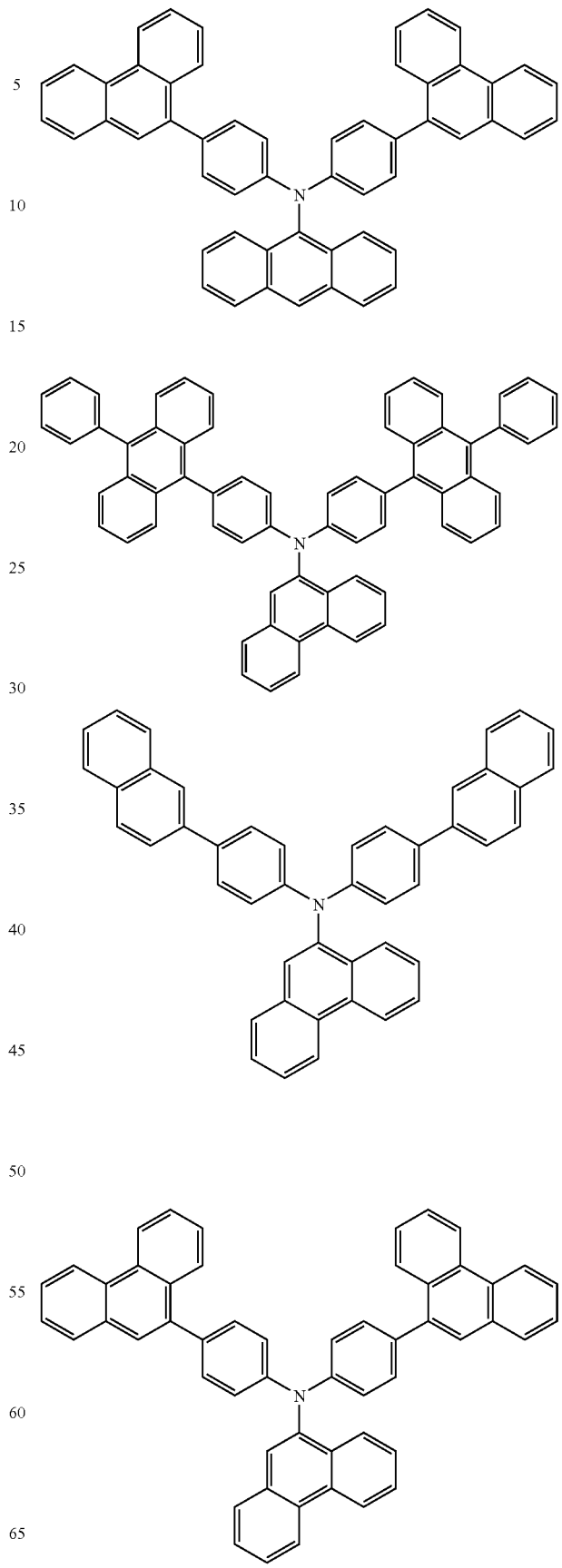

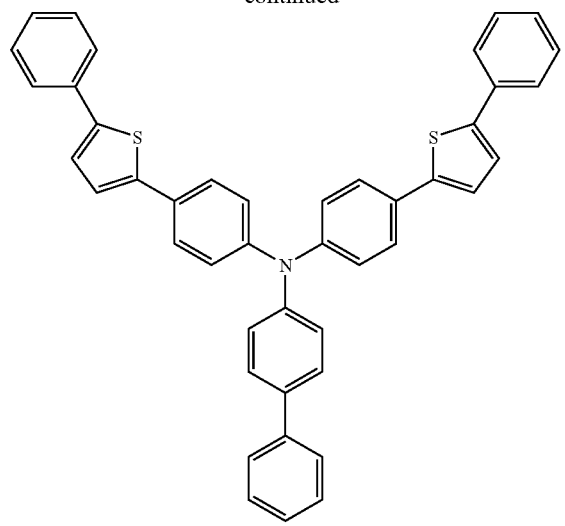
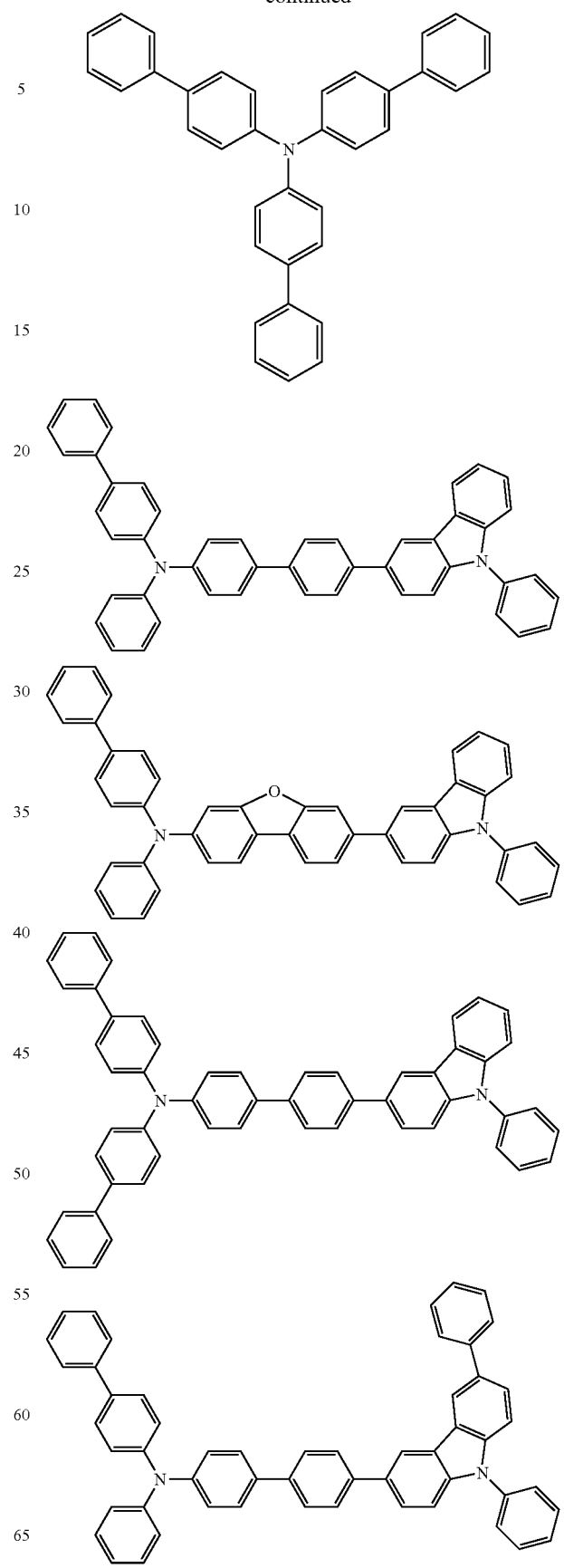

181
-continued

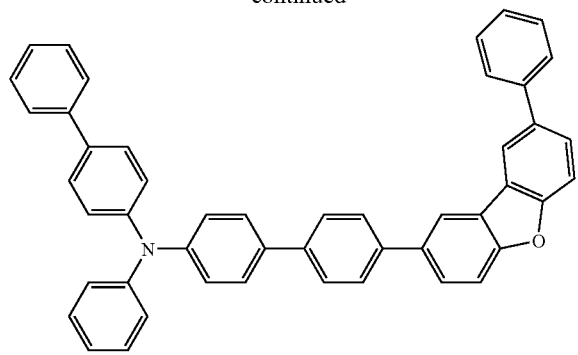

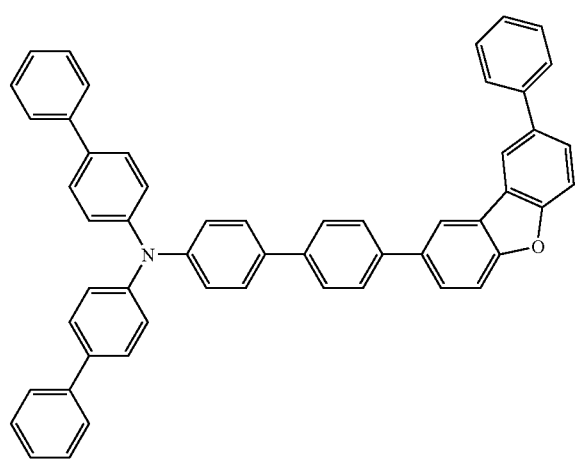

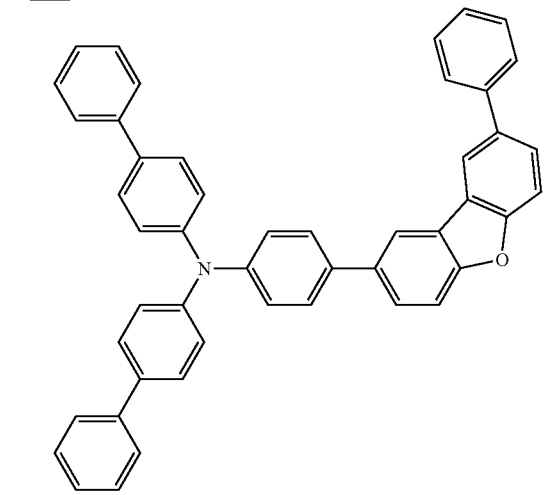

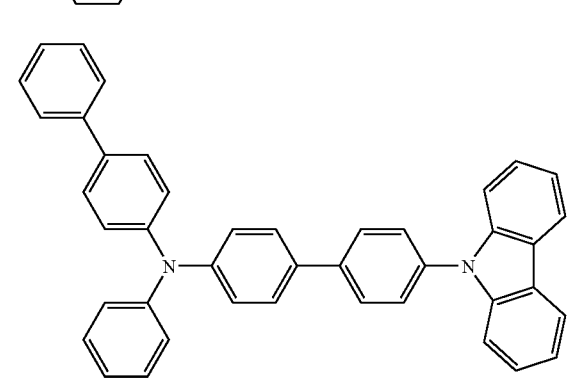

182
-continued

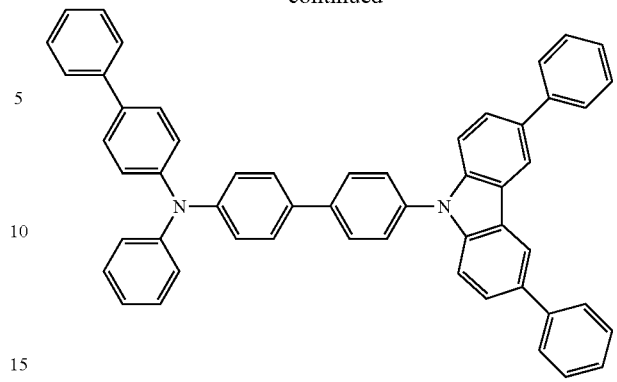

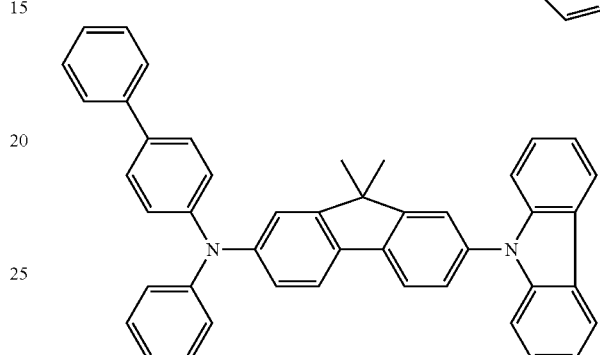

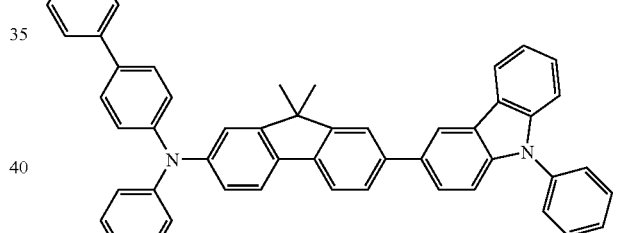

It should be noted that the invention is not limited to the above description but may include any modification as long as such modification is compatible with the invention.

For instance, the following is a preferable example of such modification made to the invention.

According to the aspect of the invention, the emitting layer may also preferably contain an assistance substance for assisting injection of charges.

When the emitting layer is formed of a host material that exhibits a wide energy gap, a difference in ionization potential (Ip) between the host material and the hole injecting/transporting layer etc. becomes so large that the holes can hardly be injected into the emitting layer and that a driving voltage required for providing sufficient luminance may be raised.

In the above instance, introducing a hole-injectable or hole-transportable assistance substance for assisting injection of charges in the emitting layer can contribute to facilitation of the injection of the holes into the emitting layer and to reduction of the driving voltage.

As the assistance substance for assisting the injection of charges, for instance, a general hole injecting material, a general hole transporting material or the like can be used.

Examples of the material are a triazole derivative (see, for instance, the specification of U.S. Pat. No. 3,112,197), an oxadiazole derivative (see, for instance, the specification of U.S. Pat. No. 3,189,447), an imidazole derivative (see, for instance, JP-B-37-16096), a polyarylalkane derivative (see, for instance, the specifications of U.S. Pat. No. 3,615,402, No. 3,820,989 and No. 3,542,544, JP-B-45-555, JP-B-51-10983, JP-A-51-93224, JP-A-55-17105, JP-A-56-4148, JP-A-55-108667, JP-A-55-156953, and JP-A-56-36656), a pyrazoline derivative and a pyrazolone derivative (see, for instance, the specifications of U.S. Pat. No. 3,180,729 and No. 4,278,746, JP-A-55-88064, JP-A-55-88065, JP-49-105537, JP-A-55-51086, JP-A-56-80051, JP-A-56-88141, JP-A-57-45545, JP-A-54-112637 and JP-A-55-74546), a phenylenediamine derivative (see, for instance, the specification of U.S. Pat. No. 3,615,404, JP-B-51-10105, JP-B-46-3712, JP-B-47-25336, JP-A-54-53435, JP-A-54-110536 and JP-A-54-119925), an arylamine derivative (see, for instance, the specifications of U.S. Pat. No. 3,567,450, No. 3,180,703, No. 3,240,597, No. 3,658,520, No. 4,232,103, No. 4,175,961 and No. 4,012,376, JP-B-49-35702, JP-B-39-27577, JP-A-55-144250, JP-A-56-119132 and JP-A-56-22437 and the specification of West Germany Patent No. 1,110,518), an amino-substituted chalcone derivative (see, for instance, the specification of U.S. Pat. No. 3,526,501), an oxazole derivative (disclosed in, for instance, the specification of U.S. Pat. No. 3,257,203), a styrylanthracene derivative (see, for instance, JP-A-56-46234), a fluorenone derivative (see, for instance, JP-A-54-110837), a hydrazone derivative (see, for instance, the specification of U.S. Pat. No. 3,717,462 and JP-A-54-59143, JP-A-55-52063, JP-A-55-52064, JP-A-55-46760, JP-A-55-85495, JP-A-57-11350, JP-A-57-148749 and JP-A-02-311591), a stilbene derivative (see, for instance, JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749 and JP-A-60-175052), a silazane derivative (see the specification of U.S. Pat. No. 4,950,950), a polysilane type (see JP-A-02-204996), an aniline-based copolymer (see JP-A-02-282263), and a conductive polymer oligomer (particularly, thiophene oligomer) disclosed in JP-A-01-211399.

The hole-injectable material, examples of which are as listed above, is preferably a porphyrin compound (disclosed in JP-A-63-295695 etc.), an aromatic tertiary amine compound or a styrylamine compound (see, for instance, the specification of U.S. Pat. No. 4,127,412, JP-A-53-27033, JP-A-54-58445, JP-A-54-149634, JP-A-54-64299, JP-A-55-79450, JP-A-55-144250, JP-A-56-119132, JP-A-61-295558, JP-A-61-98353 or JP-A-63-295695), particularly preferably an aromatic tertiary amine compound.

In addition, 4,4'-bis(N-(1-naphthyl)-N-phenylamino)biphenyl (hereinafter, abbreviated as NPD) having in the molecule two fused aromatic rings disclosed in U.S. Pat. No. 5,061,569, 4,4',4"-tris(N-(3-methyl phenyl)-N-phenylamino)triphenylamine (hereinafter, abbreviated as MTDATA) in which three triphenylamine units disclosed in JP-A-04-308688 are bonded in a starbust form and the like may also be used.

Further, a hexaazatriphenylene derivative disclosed in Japanese Patent No. 3614405 and No. 3571977 and U.S. Pat. No. 4,780,536 may also preferably be used as the hole-injectable material.

Alternatively, inorganic compounds such as p-type Si and p-type SiC can also be used as the hole-injectable material.

A method of forming each of the layers in the organic EL device according to the aspect of the invention is not particularly limited. A conventionally-known methods such as vacuum deposition or spin coating may be employed for forming the layers. The organic thin-film layer containing the compound represented by the formula (1), which is used in the organic EL device according to the aspect of the invention, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device is not particularly limited, the thickness is generally preferably in a range of several nanometers to 1 μm because an excessively-thinned film likely entails defects such as a pin hole while an excessively-thickened film requires high voltage to be applied and deteriorates efficiency.

EXAMPLES

Next, the invention will be described in further detail by exemplifying Example(s) and Comparative(s). However, the invention is not limited by the description of Example(s).

Synthesis Example 1 (Synthesis of Compound (A1))

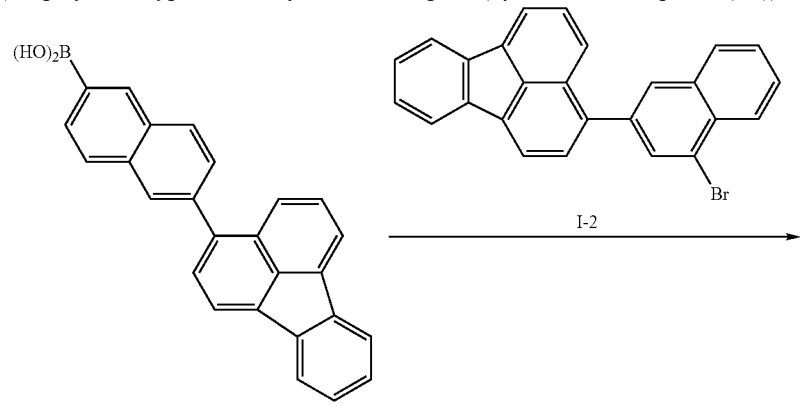

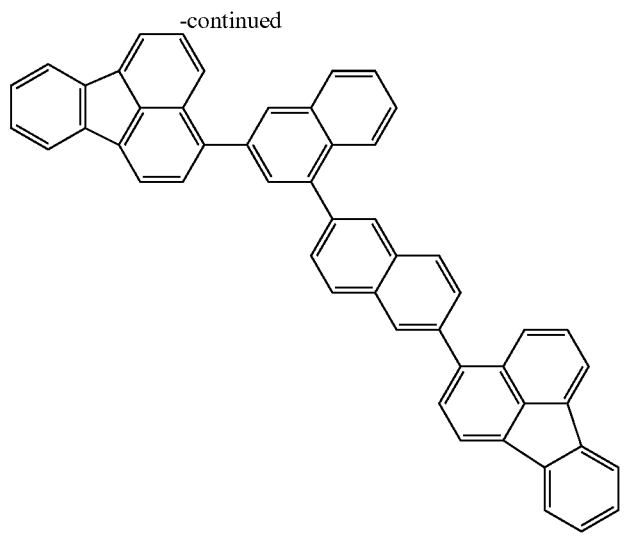

(A1)

Under an argon gas atmosphere, 7.33 g (18 mmol) of bromide I-2, 6.70 g (18 mmol) of boronic acid I-1, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized by toluene, such that 6.48 g of the compound (A1) was obtained at an yield of 55%.

FD mass analysis consequently showed that m/e was equal to 654 while a calculated molecular weight was 654.

Synthesis Example 2 (Synthesis of Compound (A3))

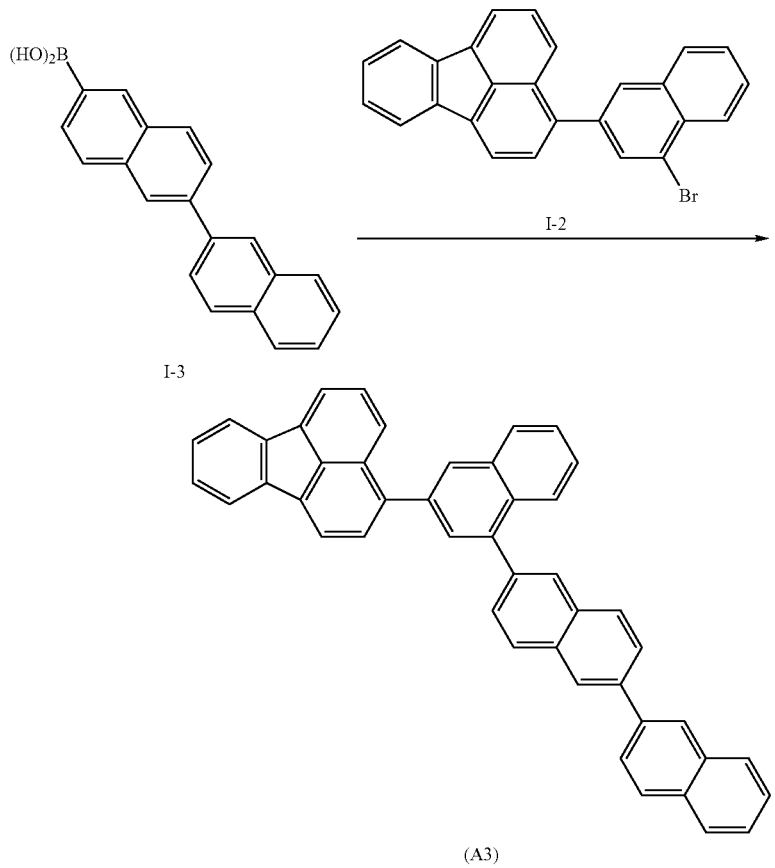

(A3)

Under an argon gas atmosphere, 7.33 g (18 mmol) of bromide I-2, 5.37 g (18 mmol) of boronic acid I-3, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized by toluene, such that 6.27 g of the compound (A3) was obtained at an yield of 60%.

FD mass analysis consequently showed that m/e was equal to 580 while a calculated molecular weight was 580.

Synthesis Example 3 (Synthesis of Compound (A7))

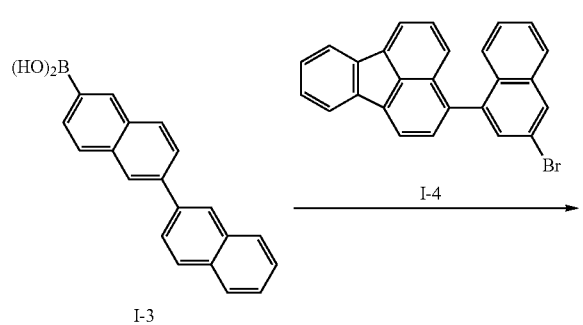

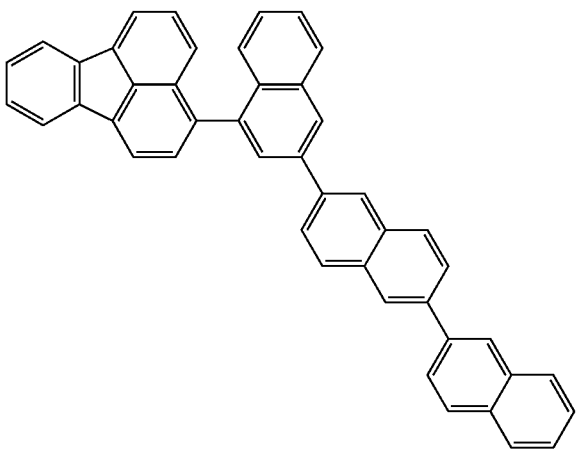

(A7)

Under an argon gas atmosphere, 7.33 g (18 mmol) of bromide I-4, 5.37 g (18 mmol) of boronic acid I-3, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 14 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized three times by toluene, such that 5.02 g of the compound (A7) was obtained at an yield of 48%.

FD mass analysis consequently showed that m/e was equal to 580 while a calculated molecular weight was 580.

Synthesis Example 4 (Synthesis of Compound (A9))

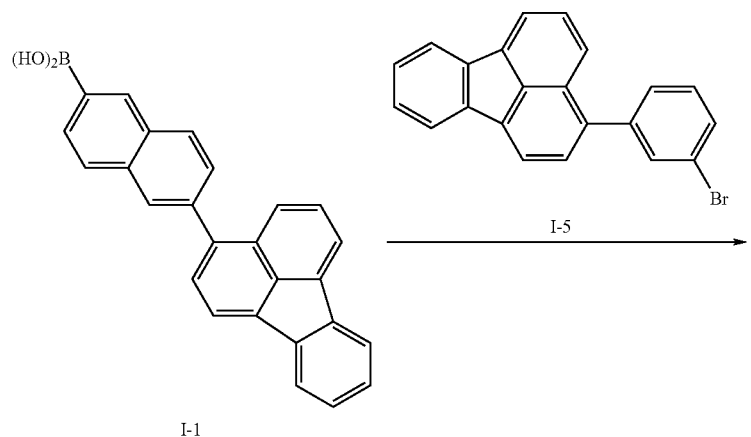

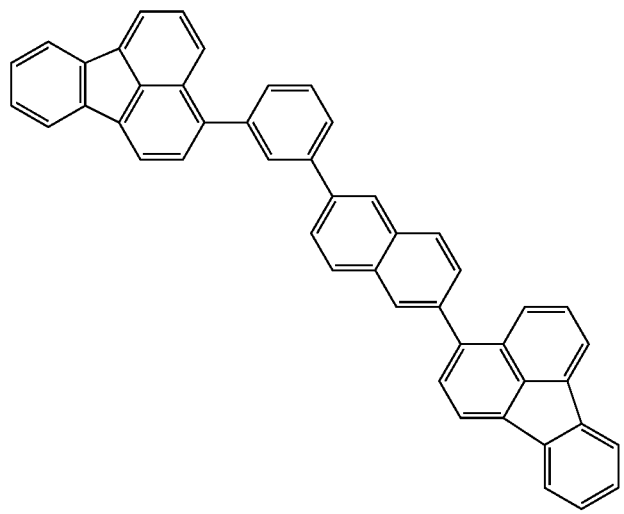

(A9)

Under an argon gas atmosphere, 5.36 g (15 mmol) of bromide I-5, 5.58 g (15 mmol) of boronic acid I-1, 350 mg (0.30 mmol) of tetrakis(triphenylphosphine)palladium(0), 60 mL of toluene, 50 mL of dimethoxyethane and 22 mL of 2M sodium carbonate solution were added together, and stirred for 10 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 3.72 g of the compound (A9) was obtained at an yield of 41%.

FD mass analysis consequently showed that m/e was equal to 604 while a calculated molecular weight was 604.

Synthesis Example 5 (Synthesis of Compound (A11))

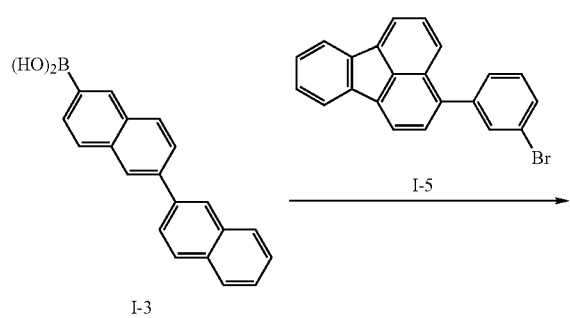

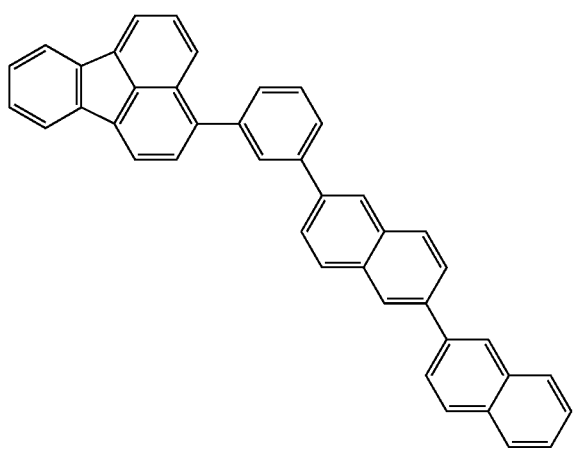

(A11)

Under an argon gas atmosphere, 5.36 g (15 mmol) of bromide I-5, 4.47 g (15 mmol) of boronic acid I-3, 350 mg (0.30 mmol) of tetrakis(triphenylphosphine)palladium(0), 60 mL of toluene, 50 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.70 g of the compound (A11) was obtained at an yield of 59%.

FD mass analysis consequently showed that m/e was equal to 530 while a calculated molecular weight was 530.

Synthesis Example 6 (Synthesis of Compound (A18))

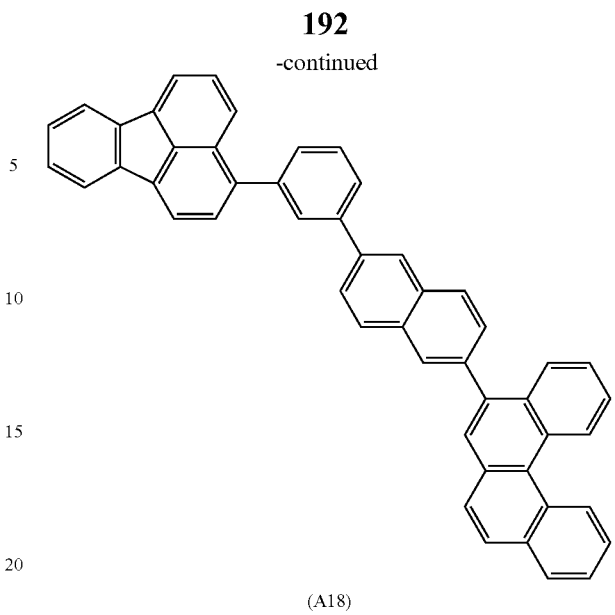

(A18)

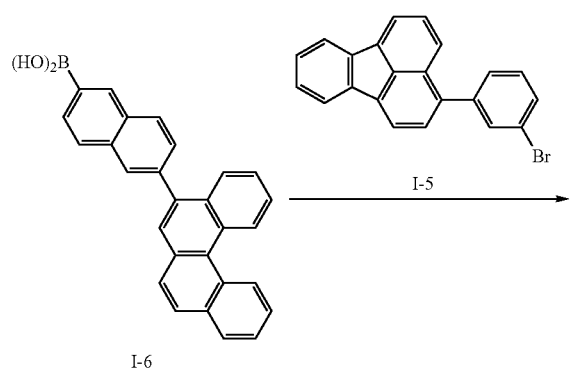

Under an argon gas atmosphere, 6.43 g (18 mmol) of bromide I-5, 7.17 g (18 mmol) of boronic acid I-6, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 11 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.31 g of the compound (A18) was obtained at an yield of 38%.

FD mass analysis consequently showed that m/e was equal to 630 while a calculated molecular weight was 630.

Synthesis Example 7 (Synthesis of Compound (A20))

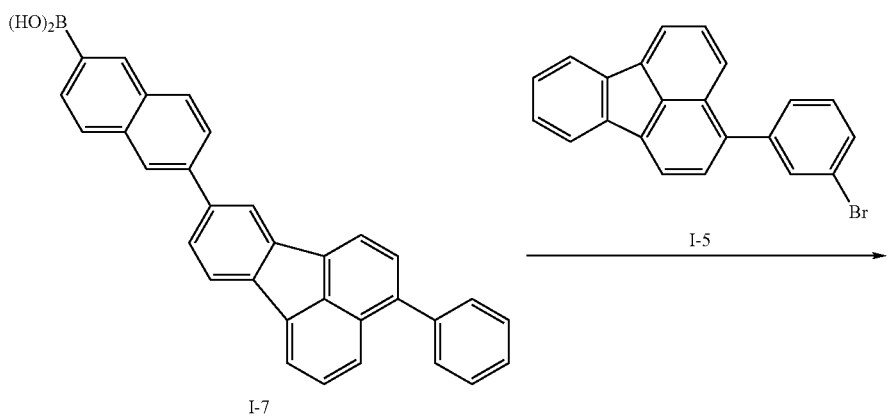

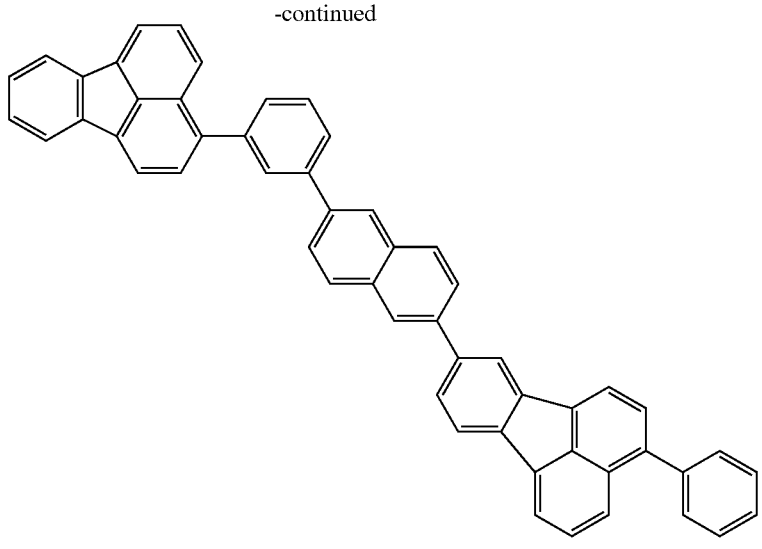

(A20)

Under an argon gas atmosphere, 6.43 g (18 mmol) of bromide I-5, 8.07 g (18 mmol) of boronic acid I-7, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.29 g of the compound (A20) was obtained at an yield of 35%.

FD mass analysis consequently showed that m/e was equal to 680 while a calculated molecular weight was 680.

Synthesis Example 8 (Synthesis of Compound (A30))

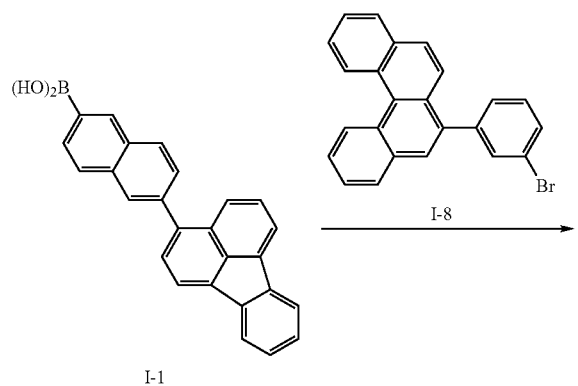

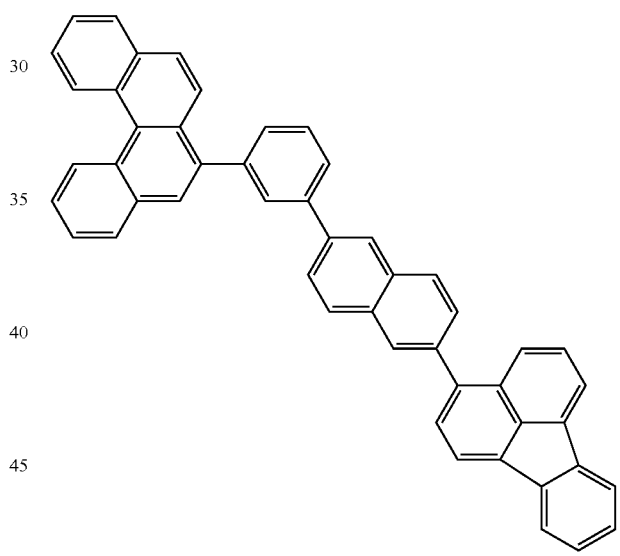

(A30)

Under an argon gas atmosphere, 6.90 g (18 mmol) of bromide I-8, 6.70 g (18 mmol) of boronic acid I-1, 420 mg (0.36 mmol) of tetrakis(triphenylphosphine)palladium(0), 80 mL of toluene, 80 mL of dimethoxyethane and 26 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized three times by toluene, such that 3.18 g of the compound (A30) was obtained at an yield of 28%.

FD mass analysis consequently showed that m/e was equal to 630 while a calculated molecular weight was 630.

Synthesis Example 9 (Synthesis of Compound (A32))

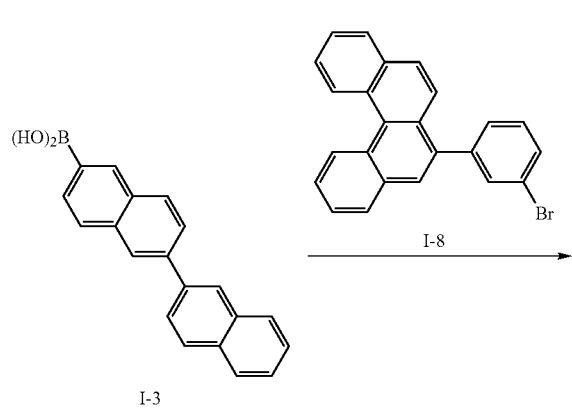

Synthesis Example 10 (Synthesis of Compound (A37))

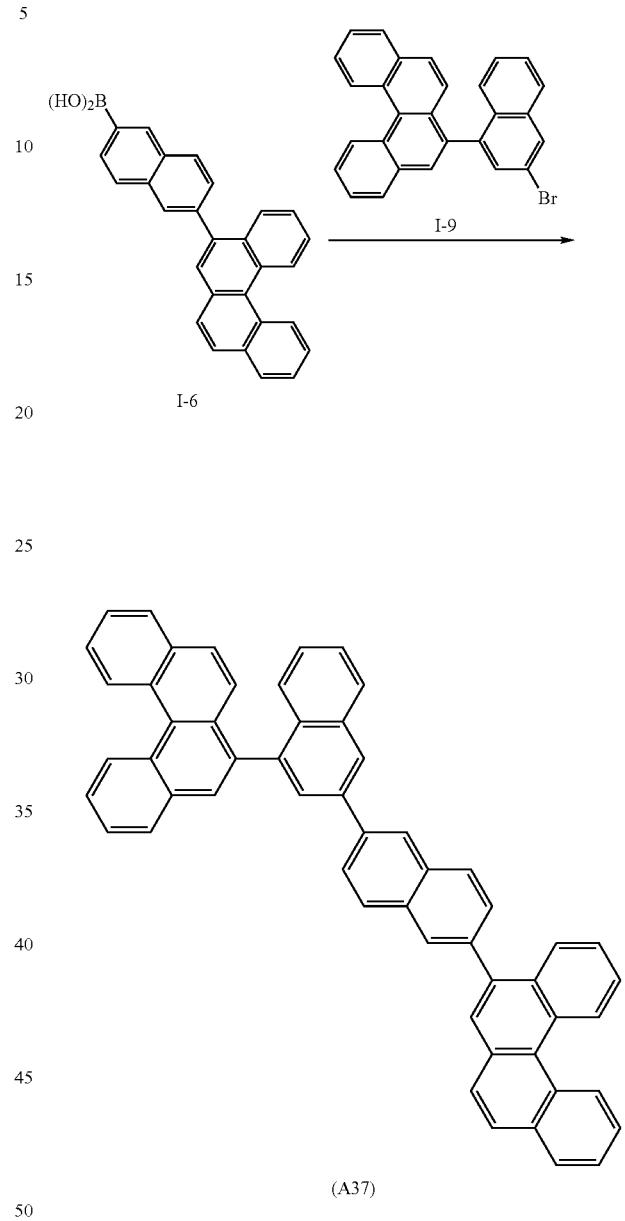

Under an argon gas atmosphere, 5.75 g (15 mmol) of bromide I-8, 4.47 g (15 mmol) of boronic acid I-3, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 13 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized three times by toluene, such that 3.26 g of the compound (A32) was obtained at an yield of 39%.

FD mass analysis consequently showed that m/e was equal to 556 while a calculated molecular weight was 556.

Under an argon gas atmosphere, 6.50 g (15 mmol) of bromide I-9, 5.97 g (15 mmol) of boronic acid I-6, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.77 g of the compound (A37) was obtained at an yield of 45%.

FD mass analysis consequently showed that m/e was equal to 706 while a calculated molecular weight was 706.

Synthesis Example 11 (Synthesis of Compound (A42))

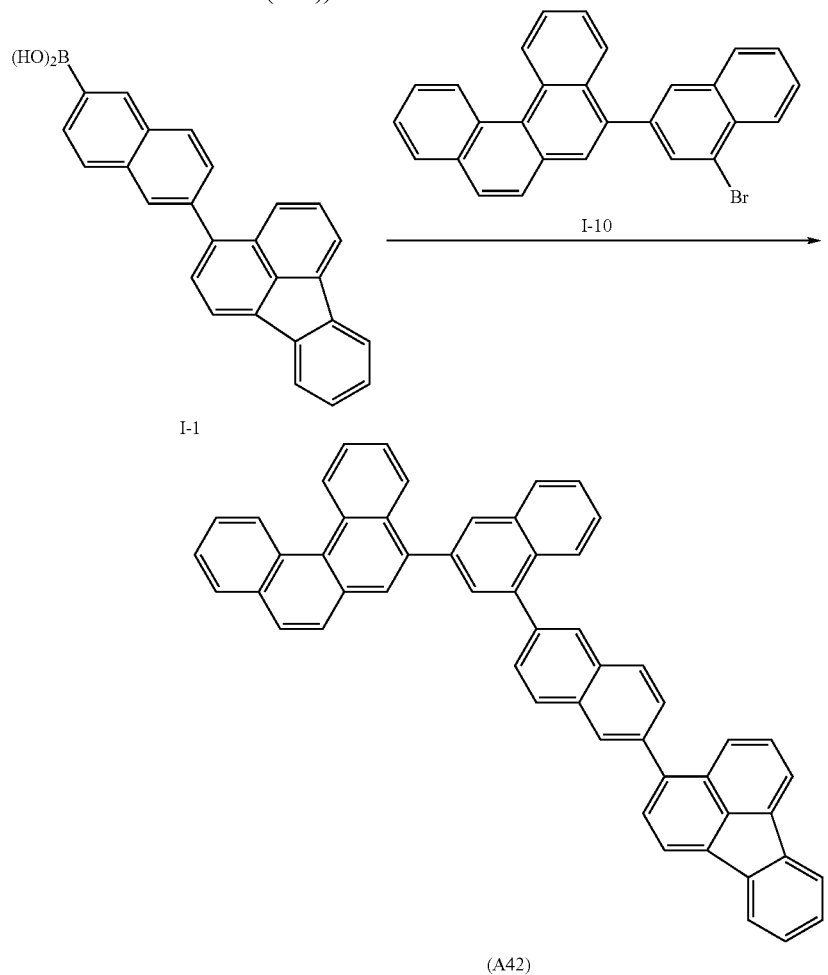

Under an argon gas atmosphere, 6.50 g (15 mmol) of bromide I-10, 5.58 g (15 mmol) of boronic acid I-1, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.49 g of the compound (A42) was obtained at an yield of 44%.

FD mass analysis consequently showed that m/e was equal to 680 while a calculated molecular weight was 680.

Synthesis Example 12 (Synthesis of Compound (A50))

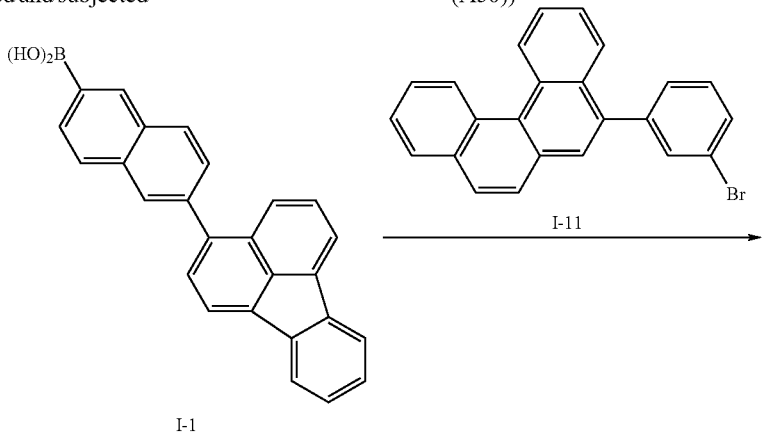

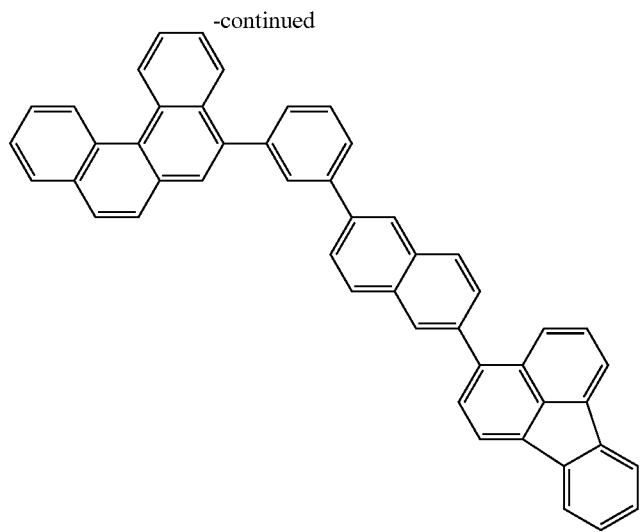

(A50)

Under an argon gas atmosphere, 5.75 g (15 mmol) of bromide I-11, 5.58 g (15 mmol) of boronic acid I-1, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 13 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.92 g of the compound (A50) was obtained at an yield of 52%.

FD mass analysis consequently showed that m/e was equal to 630 while a calculated molecular weight was 630.

Synthesis Example 13 (Synthesis of Compound (A52))

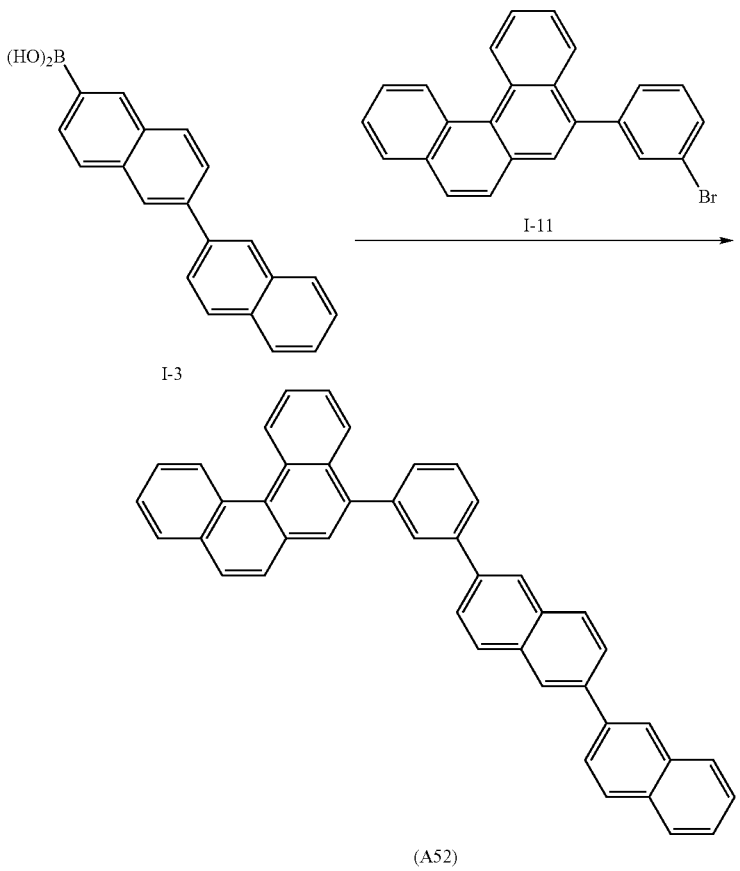

(A52)

Under an argon gas atmosphere, 5.75 g (15 mmol) of bromide I-11, 4.47 g (15 mmol) of boronic acid I-3, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 3.01 g of the compound (A52) was obtained at an yield of 36%.

FD mass analysis consequently showed that m/e was equal to 556 while a calculated molecular weight was 556.

Synthesis Example 14 (Synthesis of Compound (A59))

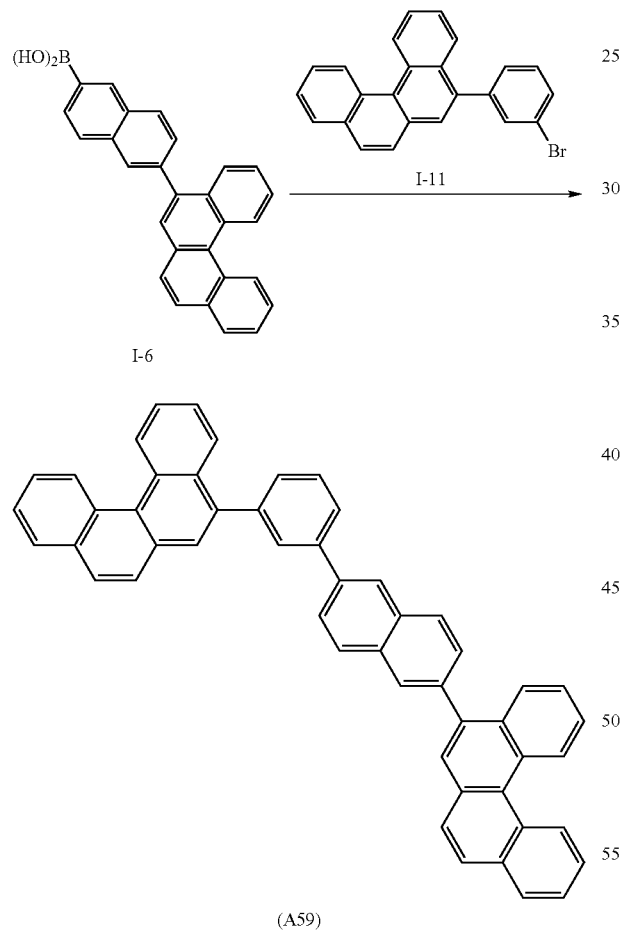

(A59)

Under an argon gas atmosphere, 5.75 g (15 mmol) of bromide I-11, 5.97 g (15 mmol) of boronic acid I-6, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized three times by toluene, such that 4.53 g of the compound (A59) was obtained at an yield of 46%.

FD mass analysis consequently showed that m/e was equal to 656 while a calculated molecular weight was 656.

Synthesis Example 15 (Synthesis of Compound (A62))

Under an argon gas atmosphere, 6.50 g (15 mmol) of bromide I-12, 4.47 g (15 mmol) of boronic acid I-3, 350 mg (0.30 mmol) of tetrakis(triphenylphosphine)palladium(0), 60 mL of toluene, 60 mL of dimethoxyethane and 22 mL of 2M sodium carbonate solution were added together, and stirred for 12 hours at 85 degrees C. Subsequently, the reaction mixture was cooled down to room temperature and added with water, and the aqueous phase was removed while the organic phase was condensed. Addition of nitrobenzene then followed, and the residue was thermally melted and subjected to filtration. Then, the residue was refined by silica-gel column chromatography and recrystallized twice by toluene, such that 4.87 g of the compound (A62) was obtained at an yield of 54%.

FD mass analysis consequently showed that m/e was equal to 556 while a calculated molecular weight was 556.

Example 1

(Manufacturing of Organic EL Device)

A glass substrate (size: 25 mm×75 mm×0.7 mm thick) having an ITO transparent electrode (manufactured by Asahi Glass Co., Ltd) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum deposition apparatus, so that 50-nm thick film of HT1 was initially formed on a surface of the glass substrate where the transparent electrode line was provided so as to cover the transparent electrode. The HT1 film serves as a hole injecting/transporting layer. Subsequently to the formation of the hole injecting/transporting layer, 40-nm thick film of the compound (A1) and film of Ir(piq)$_3$ as a phosphorescent dopant (phosphorescent material) were co-evaporated on the hole injecting/transporting layer by resistance heating so that Ir(piq)$_3$ was contained therein with a content of 10 mass %. The co-deposited film serves as an emitting layer (phosphorescent emitting layer). After the film of the emitting layer was formed, 40-nm thick film of ET1 was formed. The film of ET1 serves as an electron transporting layer. Then, 0.5-nm thick film of LiF was formed as an electron-injecting electrode (cathode) at a film-forming speed of 0.1 nm/min. Metal (A1) was vapor-deposited on the LiF film to form a 150-nm thick metal cathode, thereby providing the organic EL device.

Examples 2 to 15 and Comparatives 1 to 4

The organic EL devices according respectively to Examples 2 to 10 and Comparatives 1 to 4 were formed by the same method as Example 1 except that compounds shown in Table 1 were respectively used in place of the compound (A1).

[Evaluation on Emitting Performance of Organic EL Device]

The organic EL devices according to Examples 1 to 15 and Comparatives 1 to 4 each were driven by direct-current electricity to emit light, so that voltage, luminous efficiency and time elapsed until the initial luminance intensity of 3000 cd/m$^2$ was reduced to the half (i.e., time until half-life) at a current density of 10 mA/cm$^2$ were measured for each organic EL device.

The phosphorescence spectrum of each sample was measured by the following method. Specifically, each material was dissolved in an EPA solvent (diethylether:isopentane:ethanol=5:5:2 in volume ratio) with a concentration of 10 μmol/L, thereby forming a sample for phosphorescence measurement. Then, the sample for phosphorescence measurement was put into a quartz cell, cooled to 77 K and irradiated with exciting light (with use of FLUOROLOG II manufactured by SPEX Corporation). A tangent line was drawn to be tangent to a rising section adjacent to the short-wavelength side of the phosphorescence spectrum, and a wavelength (emission end) at an intersection of the tangent line and the abscissa axis was obtained. The obtained wavelength was converted into energy value so as to measure the triplet energy (Eg(T)) of the organic-EL-device material. The samples were all products purified by sublimation purification.

The results of the evaluation are shown in Table 1.

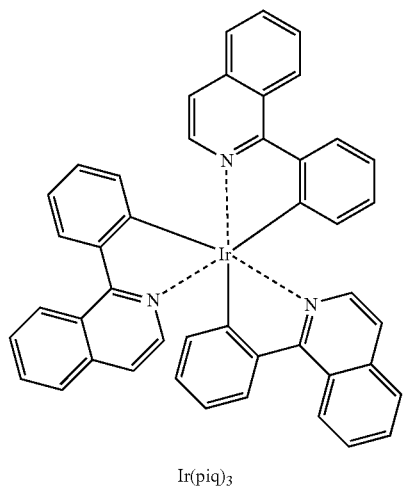

Ir(piq)$_3$

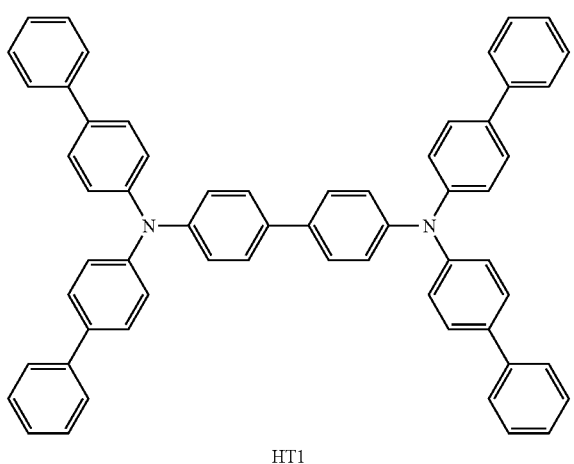

HT1

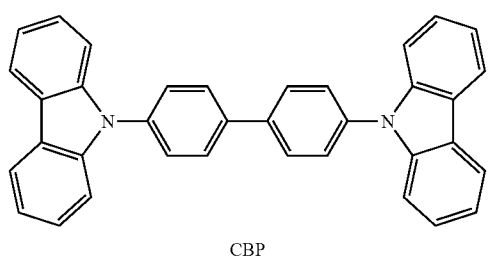

CBP

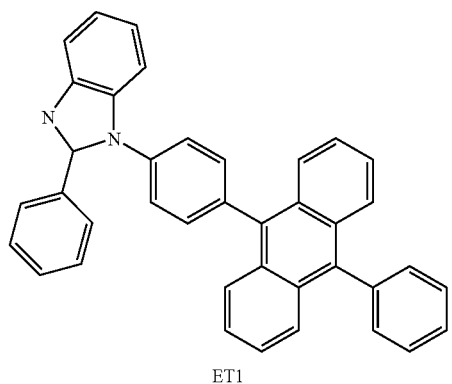

ET1

-continued

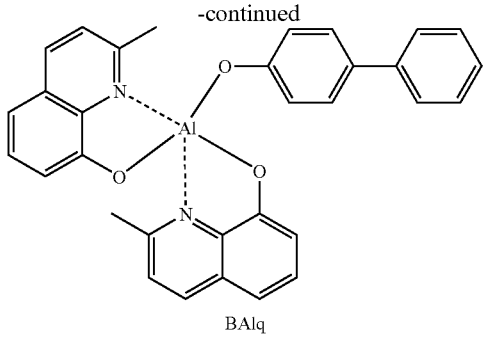
BAlq

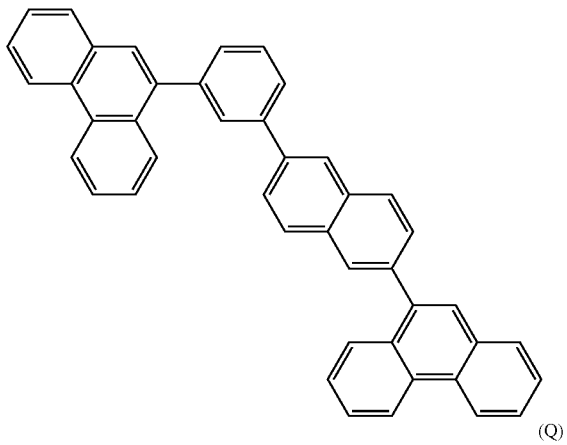
(P)

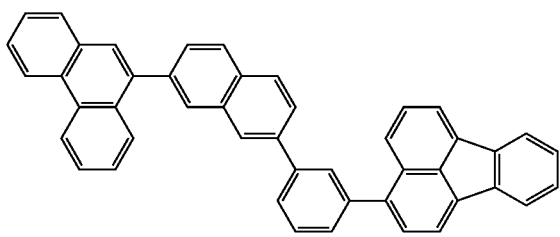
(Q)

TABLE 1

| Example | Compound | Eg (T) of Compound (eV) | Voltage (V) | Luminous Efficiency (cd/A) | Time until Half-Life (hours) |
|---|---|---|---|---|---|
| Example 1 | (A1) | 2.24 | 3.5 | 12.3 | 13000 |
| Example 2 | (A3) | 2.26 | 3.6 | 12.6 | 13900 |
| Example 3 | (A7) | 2.27 | 3.6 | 13.0 | 12800 |
| Example 4 | (A9) | 2.22 | 3.5 | 12.0 | 13300 |
| Example 5 | (A11) | 2.27 | 3.4 | 12.6 | 14000 |
| Example 6 | (A18) | 2.32 | 3.5 | 12.5 | 12800 |
| Example 7 | (A20) | 2.20 | 3.6 | 12.3 | 12500 |
| Example 8 | (A30) | 2.34 | 3.4 | 13.2 | 12700 |
| Example 9 | (A32) | 2.45 | 3.5 | 13.1 | 13300 |
| Example 10 | (A37) | 2.40 | 3.5 | 12.8 | 12500 |
| Example 11 | (A42) | 2.32 | 3.5 | 12.4 | 13000 |
| Example 12 | (A50) | 2.36 | 3.4 | 14.0 | 13700 |
| Example 13 | (A52) | 2.44 | 3.4 | 12.6 | 13500 |
| Example 14 | (A59) | 2.42 | 3.5 | 12.7 | 14100 |
| Example 15 | (A62) | 2.37 | 3.5 | 12.5 | 14700 |
| Comparative 1 | CBP | 2.81 | 5.7 | 6.3 | 1200 |
| Comparative 2 | BAlq | 2.28 | 5.3 | 7.0 | 2300 |
| Comparative 3 | (P) | 2.47 | 4.3 | 12.3 | 12500 |
| Comparative 4 | (Q) | 2.38 | 4.4 | 10.0 | 10500 |

As is clearly understandable from Table 1, with respect to luminous efficiency, the organic EL device according to each of Examples 1 to 15, which was formed of the organic-EL-device material according to the aspect of the invention, has been found to require low driving voltage, exhibit high external quantum efficiency and have considerably long lifetime.

In contrast, the organic EL device according to each of Comparatives 1 and 2 required relatively high driving voltage, exhibited low luminous efficiency and had short lifetime. The organic EL device according to each of Comparatives 3 and 4 exhibited an approximately equal level of luminous efficiency, but required driving voltage higher by 0.7 to 1.0 V than those required by the devices of Examples 1 to 15.

When applied as the host material of an organic EL device, the material according to the aspect of the invention enables the luminous efficiency to be enhanced because the triplet energy of the host material and the triplet energy of the dopant are well-balanced, and enables the device to have a longer lifetime than a device provided by a conventionally-known combination of materials because the organic-EL-device material contains no nitrogen-containing ring or nitrogen atom in its molecular skeleton and thus exhibits high tolerance of holes and electrons. In addition, by selecting the specific partial structure and the specific molecular linkage structure, the driving voltage of the organic EL device can be dramatically reduced, and the power consumption by the organic EL device can be dramatically improved.

The entire disclosure of Japanese Patent Application No. 2009-092523, filed Apr. 6, 2009, is expressly incorporated by reference herein.

What is claimed is:

1. An organic electroluminescence device, comprising:
   a cathode;
   an anode; and
   a single-layered or multilayered organic thin-film layer provided between the cathode and the anode, wherein
   at least one layer of the organic thin-film layer comprises:
   an organic-electroluminescence-device material represented by a general formula selected from following formulae (1), (2) and (3); and
   at least one phosphorescent material,

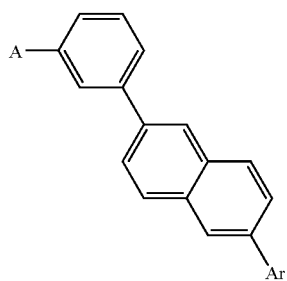
(1)

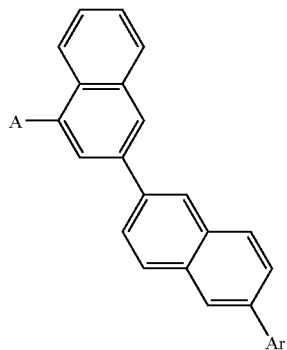
(2)

-continued

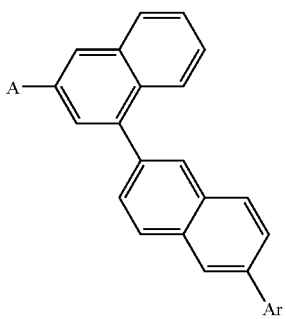
(3)

where: A represents a group selected from a 3-fluoranthenyl group, 5-benzo[c]phenanthrenyl group, 6-benzo[c]phenanthrenyl group and 10-benzo[g]chrysenyl group;
Ar represents a fused aromatic ring having 10 to 30 carbon atoms and having triplet energy of 2.10 eV or more; and
A or Ar is allowed to be substituted by a phenyl group or a naphthyl group.

2. The organic electroluminescence device according to claim 1, wherein the A represents a group selected from an unsubstituted 3-fluoranthenyl group, 5-benzo[c]phenanthrenyl group, 6-benzo[c]phenanthrenyl group and 10-benzo[g]chrysenyl group.

3. The organic electroluminescence device according to claim 1, wherein the Ar each independently represent a group selected from a naphthyl group, fluoranthenyl group, phenanthrenyl group, benzophenanthrenyl group and benzo[g]chrysenyl group.

4. The organic electroluminescence device according to claim 3, wherein the Ar represents a group selected from a 2-naphthyl group, 3-fluoranthenyl group, 8-fluoranthenyl group, 9-phenanthrenyl group, 5-benzo[c]phenanthrenyl group, 6-benzo[c]phenanthrenyl group and 10-benzo[g]chrysenyl group.

5. The organic electroluminescence device according to claim 1, wherein triplet energy of the organic-electroluminescence-device material represented by the formula (1), (2) or (3) is in a range of 2.0 eV to 2.5 eV.

6. The organic electroluminescence device according to claim 1, wherein
the at least one layer of the organic thin-film layer is an emitting layer, and
at least one layer of the emitting layer comprises: the organic-electroluminescence-device material represented by the formula (1), (2) or (3); and at least one phosphorescent material.

7. The organic electroluminescence device according to claim 6, wherein the phosphorescent material contains a metal complex, the metal complex comprising: a metal atom selected from Ir, Pt, Os, Au, Re and Ru; and a ligand.

8. The organic electroluminescence device according to claim 7, wherein the ligand has: a metal atom for forming a complex; and an ortho-metal bond.

9. The organic electroluminescence device according to claim 1, wherein a maximum wavelength of light emission of the at least one phosphorescent material contained in the emitting layer is in a range of 520 nm to 720 nm.

10. The organic electroluminescence device according to claim 1, wherein the organic thin-film layer comprises an electron transporting layer between the cathode and the emitting layer, the electron transporting layer comprising the organic-electroluminescence-device material.

11. The organic electroluminescence device according to claim 1, wherein
the organic thin-film layer comprises an electron transporting layer or an electron injecting layer between the cathode and the emitting layer, and
the electron transporting layer or the electron injecting layer comprises an aromatic ring having a nitrogen-containing six-membered or five-membered ring skeleton, or a fused aromatic cyclic compound having a nitrogen-containing six-membered or five-membered ring skeleton.

12. The organic electroluminescence device according to claim 1, wherein a reductive dopant is present at an interfacial region between the cathode and the organic thin-film layer.

13. An organic-electroluminescence-device material, represented by a following formula (1), (2) or (3),

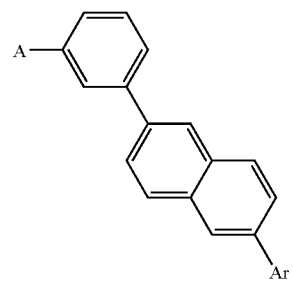
(1)

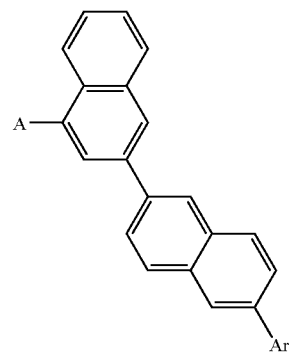
(2)

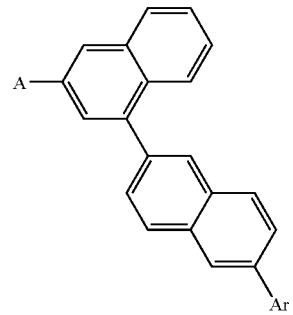
(3)

where: A represents a group selected from a 3-fluoranthenyl group, 5-benzo[c]phenanthrenyl group, 6-benzo[c]phenanthrenyl group and 10-benzo[g]chrysenyl group;
Ar represents a fused aromatic ring having 10 to 30 carbon atoms and having triplet energy of 2.10 eV or more; and
A or Ar is allowed to be substituted by a phenyl group or a naphthyl group.

14. The organic-electroluminescence-device material according to claim 13, wherein the A represents a group selected from an unsubstituted 3-fluoranthenyl group, 5-benzo[c]phenanthrenyl group, 6-benzo[c]phenanthrenyl group and 10-benzo[g]chrysenyl group.

15. The organic-electroluminescence-device material according to claim 13, wherein the Ar each independently represent a group selected from a naphthyl group, fluoranthenyl group, phenanthrenyl group, benzophenanthrenyl group and benzo[g]chrysenyl group.

16. The organic-electroluminescence-device material according to claim 15, wherein the Ar represents a group selected from a 2-naphthyl group, 3-fluoranthenyl group, 8-fluoranthenyl group, 9-phenanthrenyl group, 5-benzo[c]phenanthrenyl group, 6-benzo[c]phenanthrenyl group and 10-benzo[g]chrysenyl group.

* * * * *